(12) United States Patent
Hunt et al.

(10) Patent No.: US 8,436,028 B2
(45) Date of Patent: *May 7, 2013

(54) CETP INHIBITORS DERIVED FROM BENZOXAZOLE ARYLAMIDES

(75) Inventors: Julianne A. Hunt, Montclair, NJ (US); Rogelio L. Martinez, Monmuth Junction, NJ (US); Peter J. Sinclair, Scotch Plains, NJ (US); Ramzi F. Sweis, Franklin Park, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 324 days.

This patent is subject to a terminal disclaimer.

(21) Appl. No.: 12/664,715

(22) PCT Filed: Jun. 16, 2008

(86) PCT No.: PCT/US2008/007470
§ 371 (c)(1),
(2), (4) Date: Dec. 15, 2009

(87) PCT Pub. No.: WO2008/156717
PCT Pub. Date: Dec. 24, 2008

(65) Prior Publication Data
US 2010/0197630 A1 Aug. 5, 2010

Related U.S. Application Data

(60) Provisional application No. 60/936,570, filed on Jun. 20, 2007.

(51) Int. Cl.
A61K 31/423 (2006.01)
C07D 498/00 (2006.01)

(52) U.S. Cl.
USPC ......................... 514/375; 548/224

(58) Field of Classification Search ......................... None
See application file for complete search history.

(56) References Cited

U.S. PATENT DOCUMENTS

| 4,831,152 A | 5/1989 | Itoh et al. |
| 2005/0038095 A1* | 2/2005 | Farina et al. .................. 514/393 |
| 2006/0040999 A1 | 2/2006 | Ali et al. |

FOREIGN PATENT DOCUMENTS

| WO | WO 96/11917 | 4/1996 |
| WO | WO 00/45819 | 8/2000 |
| WO | WO01/00587 | 1/2001 |
| WO | WO 01/14354 A1 | 3/2001 |
| WO | WO 2007/070173 A2 | 6/2007 |
| WO | WO 2008/156715 A1 | 12/2008 |
| WO | WO 2008/156718 A1 | 12/2008 |

OTHER PUBLICATIONS

Inzerillo et al. "Osteoporosis and Diabetes Mellitus," Reviews in Endocrine & Metabolic Disorders, 2004: 5, pp. 261-268.*
Supplemental European Search Report (Munich) ; Performed Jun. 22, 2011.

* cited by examiner

*Primary Examiner* — Rebecca Anderson
*Assistant Examiner* — Alicia L Otton
(74) *Attorney, Agent, or Firm* — James L. McGinnis; Catherine D. Fitch

(57) ABSTRACT

Compounds having the structure of Formula I, including pharmaceutically acceptable salts of the compounds, are potent CETP inhibitors, and are useful for raising HDL-cholesterol, reducing LDL-cholesterol, and for treating or preventing atherosclerosis. In formula I, A-B is an arylamide moiety.

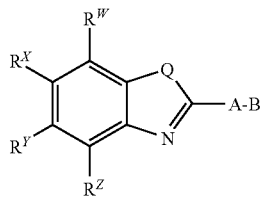

18 Claims, No Drawings

CETP INHIBITORS DERIVED FROM BENZOXAZOLE ARYLAMIDES

CROSS REFERENCE TO RELATED APPLICATIONS

This application is a U.S. National Phase application under 35 U.S.C. §371 of PCT Application No. PCT/US2008/007470, filed 16 Jun. 2008, which claims priority under 35 U.S.C. §119(e) from U.S. Application No. 60/936,570, filed 20 Jun. 2007.

FIELD OF THE INVENTION

This invention relates to a class of chemical compounds that inhibit cholesterol ester transfer protein (CETP) and therefore have utility in raising HDL-cholesterol, lowering LDL-cholesterol, and in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. Clinical trials of Pfizer's CETP inhibitor torcetrapib were recently terminated because of increased mortality in patients who were using the drug during outcomes studies. New compounds are needed so that one or more pharmaceutical compounds can be found that are safe and effective. The novel compounds described herein are very potent CETP inhibitors. They are amide derivatives of 2-arylbenzoxazoles and related compounds. A different family of CETP inhibitors based on 2-arylbenzoxazoles is disclosed in WO 2007/070173.

SUMMARY OF THE INVENTION

Compounds having Formula I, including pharmaceutically acceptable salts of the compounds, are CETP inhibitors, and have utility in raising HDL-cholesterol, lowering LDL-cholesterol, and in treating, preventing, and/or reducing the risk of developing atherosclerosis:

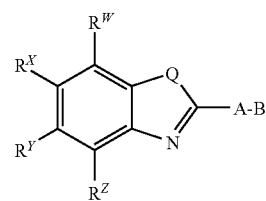

In the compounds of Formula I, including pharmaceuticaly acceptable salts thereof, Q is selected from the group consisting of O, S, and —N($R^2$)—;

A is a difunctional cyclic group selected from 1,4-phenylene, 2,5-pyridinylene, and 2,5-pyrimidinylene, wherein A is optionally substituted with 1-3 substituent groups $R^1$;

Each $R^1$ is independently selected from the group consisting of halogen, $C_1$-$C_3$alkyl, $C_2$-$C_3$alkenyl, $C_2$-$C_3$alkynyl, and —$OC_1$-$C_3$alkyl, wherein each alkyl, alkenyl, and alkynyl substituent is optionally substituted with 1-5 halogens;

Each $R^2$ is independently selected from the group consisting of H, $C_1$-$C_3$alkyl, $C_2$-$C_3$alkenyl, and $C_2$-$C_3$alkynyl, wherein each alkyl, alkenyl, and alkynyl substituent is optionally substituted with 1-5 halogens;

$R^W$ is selected from the group consisting of (a) $C_1$-$C_5$alkyl which is optionally substituted with 1-5 halogens, (b) $C_{2-5}$ alkenyl which is optionally substituted with 1-5 halogens; (c) —$OC_1$-$C_5$ alkyl which is optionally substituted with 1-5 halogens, (d) —$SC_1$-$C_5$ alkyl which is optionally substituted with 1-5 halogens, (e) —$OC_{2-5}$ alkenyl which is optionally substituted with 1-5 halogens, (f) $C_3$-$C_6$cycloalkyl, (g) phenyl, (h) a 5-6 membered saturated or partly unsaturated heterocyclic group having 1-3 heteroatoms independently selected from N, S and O, (i) a 5-7 membered heteroaromatic group having 1-3 heteroatoms independently selected from N, S, and O, (j) —C(=O)$OC_{1-3}$alkyl which is optionally substituted with 1-5 halogens, and (k) —C(=O)OH, wherein said $C_3$-$C_6$cycloalkyl, phenyl, 5-6 membered saturated or partly unsaturated heterocyclic group, and 5-7 membered heteroaromatic group are optionally substituted with 1-3 substituents independently selected from halogen, $CH_3$, $CF_3$, —$OCH_3$, and —$OCF_3$;

$R^Y$ is selected from the group consisting of halogen, $CH_3$, $CF_3$, —$OCH_3$, —$OCF_3$, —CN, phenyl, and a 6-membered heteroaroaromatic group having 1-2 N, wherein phenyl and the 6-membered heteroaroaromatic group are optionally substituted with 1-3 substituents independently selected from halogen, $CH_3$, $CF_3$, —$OCH_3$, and —$OCF_3$;

$R^X$ and $R^Z$ are each selected from the group consisting of H, halogen, $CH_3$, $CF_3$, —$OCH_3$, and —$OCF_3$;

B is selected from the group consisting of:
(a) —C(=O)N($R^3$)($CR^4R^5$)$_x$($CR^6R^7$)$_y$$D^2$, and
(b) —C(=O)N($R^3$)($CR^4R^5$)$D^5$;

$R^3$ is selected from the group consisting of H and $C_1$-$C_3$alkyl;

$R^4$ is selected from the group consisting of H, $C_1$-$C_3$alkyl, $CF_3$, —C(=O)OH, and —C(=O)$OC_1$-$C_3$alkyl;

$R^5$ is selected from the group consisting of H, $C_1$-$C_3$alkyl, and $CF_3$;

$R^6$ is selected from the group consisting of H, $C_1$-$C_3$alkyl, $CF_3$, —C(=O)OH, and —C(=O)$OC_1$-$C_3$alkyl;

$R^7$ is selected from the group consisting of H, $C_1$-$C_3$alkyl, $CF_3$, and phenyl, which is optionally substituted with 1-3 groups independently selected from halogen, $CH_3$, $CF_3$, —$OCH_3$, and —$OCF_3$;

x is 0 or 1;

y is 0, 1, or 2;

$D^2$ is a cyclic group selected from the group consisting of
(a) $C_3$-$C_8$Cycloalkyl which optionally comprises 1-2 double bonds and is optionally fused to a phenyl ring,
(b) Bicyclic $C_6$-$C_{12}$Cycloalkyl optionally comprising 1-2 double bonds,
(c) A 4-8 membered saturated or partly unsaturated heterocyclic ring comprising 1-3 ring members independently selected from —O— and —S—, optionally one carbonyl group, and optionally 1-2 double bonds, said heterocyclic ring being connected to the remainder of the structure represented by Formula I through a carbon atom of the heterocyclic ring, wherein said heterocyclic ring is optionally fused to a phenyl ring or to a $C_5$-$C_7$Cycloalkyl,
(d) A spirocyclic group having two rings joined by a spirocyclic linkage through a carbon atom wherein each ring is a 5-7-membered ring, wherein $D^2$ optionally comprises in either ring of the spirocyclic group (i) optionally 1-2 ring members independently selected from —O— and —S—, (ii) optionally one carbonyl group, and (iii) optionally 1-2 double bonds, wherein either ring of the spirocyclic group $D^2$ is optionally fused to a phenyl ring or to a $C_5$-$C_7$Cycloalkyl,
(e) An aromatic ring selected from phenyl and naphthyl, and
(f) A 5-7 membered heteroaromatic ring having 1-3 heteroatoms independently selected from N, S, and O, and optionally having one —C(=O)— group as a ring member, said heteroaromatic ring being connected to the right side of the structure represented by Formula I through a carbon atom of the heteroaromatic ring, wherein said heteroaromatic ring is optionally fused to a phenyl ring;

Wherein said cyclic groups $D^2$ defined in (a)-(f), including optional fused rings, are optionally substituted with 1-5 substitutents independently selected from halogen, —CN, —$NO_2$, —OH, —N($R^3$)$_2$, $C_1$-$C_7$alkyl, $C_2$-$C_7$alkenyl, $CF_3$, —$OC_1$-$C_5$alkyl, —$C_1$-$C_5$alkylene-$OC_1$-$C_5$alkyl, —$OCF_3$, —C(=O)$C_1$-$C_5$alkyl, —C(=O)$OC_1$-$C_5$alkyl, —C(=O)OH, and —$NR^3$C(=O)$C_1$-$C_5$alkyl, and are optionally substituted with one substituent selected from the group consisting of 4,4,5,5-tetramethyl-1,3,2-dioxaborolan-2-yl (see Ex 8) and a cyclic group $D^4$, wherein $C_1$-$C_7$alkyl, $C_2$-$C_7$alkenyl, and $OC_1$-$C_5$alkyl in all uses are optionally substituted with 1-9 halogens, wherein $D^4$ is connected directly to $D^2$ or is connected to $D^2$ through a linking group $L^4$, Wherein $D^4$ is selected from the group consisting of (a) phenyl, (b) naphthyl, (c) $C_3$-$C_8$cycloalkyl optionally having 1-2 double bonds, (d) a saturated or partially unsaturated monocyclic or bicyclic 4-10 membered heterocycle having 1-3 heteroatoms independently selected from N, O, and S and optionally one —C(=O)— group, said heterocycle optionally having 1-2 double bonds, and (e) a monocyclic or bicyclic 5-12 membered heteroaromatic group having 1-3 heteroatoms independently selected from N, S, and O and optionally having one —C(=O)— group, and $L^4$ is selected from the group consisting of —C(=O)—, S, —S(O)$_2$—, O, —N($R^3$)C(=O)—, —$CH_2$N($R^3$)C(=O)—, —$CH_2$C(=O)N($R^3$)—, —N($R^3$)S(O)$_2$—, —$CH_2$N($R^3$)S(O)$_2$—, —$CH_2$S(O)$_2$N($R^3$)—, —$C_2$-$C_5$alkenylene-, and —$C_1$-$C_5$alkylene-which optionally comprises one heteroatom or a difunctional group selected from O, S, —S(O)$_2$—, —$NR^3$—, —N($R^3$)C(=O)—, and —N($R^3$)S(O)$_2$— between 2 adjacent carbons of the —$C_1$-$C_5$alkylene-group, wherein $D^4$ is optionally substituted with 1-3 substituents independently selected from halogen, —CN, —$NO_2$, —N($R^3$)$_2$—, —OH, $C_1$-$C_7$alkyl, $C_2$-$C_7$alkenyl, $CF_3$, —$OC_1$-$C_5$ allyl, —$C_1$-$C_5$ alkylene-$OC_1$-$C_5$alkyl, and —$OCF_3$, and is optionally substituted with one cyclic group $D^6$ bonded directly to $D^4$ or connected to $D^4$ through a linking group $L^6$, wherein $D^6$ has the same selections as $D^4$, and $L^6$ has the same selections as $L^4$, and $D^6$ is optionally substituted with 1-3 substituents independently selected from halogen, —CN, —$NO_2$, —N($R^3$)$_2$—, —OH, $C_1$-$C_7$alkyl, $C_2$-$C_7$alkenyl, $CF_3$, —$OC_1$-$C_5$alkyl, —$C_1$-$C_5$alkylene-$OC_1$-$C_5$alkyl, and —$OCF_3$, wherein the $C_1$-$C_7$alkyl, $C_2$-$C_7$alkenyl, and —$OC_1$-$C_5$alkyl groups in all uses in substituents on $D^4$ and $D^6$ are optionally substituted with 1-5 halogens; and $D^5$ is selected from the group consisting of —$OC_1$-$C_7$alkyl, —$CH_2$S(O)$_2$$C_1$-$C_7$alkyl, $C_2$-$C_{15}$ alkyl, $C_2$-$C_{15}$alkenyl, $C_2$-$C_{15}$ alkynyl, —$NR^3C_1$-$C_7$alkyl, —$NR^3$C(=O)$OC_1$-$C_7$alkyl, and —OC(=O)$OC_1$-$C_7$alkyl, wherein the $C_1$-$C_{15}$alkyl, $C_2$-$C_{15}$alkenyl, $C_2$-$C_{15}$alkynyl, and $C_1$-$C_7$alkyl groups of $D^5$ are optionally substituted with 1-9 halogens and are optionally substituted with one group selected from —N($R^3$)$_2$, —N($R^3$)C(=O)$OC_1$-$C_7$alkyl, —N($R^3$)C(=O)

$C_1$-$C_7$alkyl, and —OH, wherein the $C_1$-$C_7$alkyl groups of the —N($R^3$)C(=O)O$C_1$-$C_7$alkyl and —N($R^3$)C(=O)$C_1$-$C_7$alkyl substituents on $D^5$ are optionally substituted with 1-9 halogens.

In the compounds of formula I and in compounds described subsequently, alkyl, alkenyl and alkynyl groups can be linear or branched, unless otherwise stated.

DETAILED DESCRIPTION OF THE INVENTION

In embodiments of the invention,
Q is O.

In embodiments of the invention, A is a difunctional cyclic group selected from 1,4-phenylene, 2,5-pyridinylene, and 2,5-pyrimidinylene, wherein A is optionally substituted with 1-3 substituent groups $R^1$.

In embodiments of the invention, each $R^1$ is independently selected from the group consisting of halogen, $CH_3$, $CF_3$, —$OCH_3$, and —$OCF_3$.

In embodiments of the invention, $R^W$ is selected from the group consisting of (a) $C_1$-$C_5$alkyl which is optionally substituted with 1-5 F, (b) $C_{2-3}$ alkenyl which is optionally substituted with 1-3 F, (c) —$OC_1$-$C_3$ alkyl which is optionally substituted with 1-3 F, (d) —$SC_1$-$C_3$ alkyl which is optionally substituted with 1-3 F, (e) —$OC_{2-3}$ alkenyl which is optionally substituted with 1-3 F, (f) $C_3$-$C_6$cycloalkyl, (g) phenyl, (h) pyridyl, (i) —C(=O)O$C_{1-3}$alkyl which is optionally substituted with 1-3 F, and (k) —C(=O)OH, wherein said $C_3$-$C_6$cycloalkyl, phenyl, and pyridinyl substituents are optionally substituted with 1-3 substituents independently selected from halogen, $CH_3$, $CF_3$, —$OCH_3$, and —$OCF_3$.

In embodiments of the invention, $R^Y$ is selected from the group consisting of halogen, $CH_3$, $CF_3$, —$OCH_3$, —$OCF_3$, and —CN.

In embodiments of the invention, $R^X$ and $R^Z$ are each selected from the group consisting of H, halogen, $CH_3$, $CF_3$, —$OCH_3$, and —$OCF_3$.

The compound of the invention is also described by Formula Ia, or a pharmaceutically acceptable salt thereof:

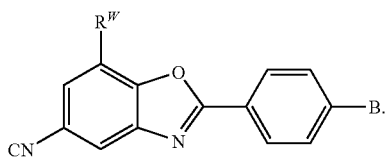

Ia

In embodiments of the compounds of Formula I and Ia, $R^W$ is selected from the group consisting of $C_1$-$C_4$alkyl which is optionally substituted with 1-3 F, $C_{2-3}$ alkenyl, —$OCH_3$, —$OCF_3$, —$SCH_3$, —$SCF_3$, cyclopropyl, —C(=O)O$C_{1-3}$alkyl, and phenyl which is optionally substituted with 1-3 substituents independently selected from halogen, $CH_3$, $CF_3$, —$OCH_3$, and —$OCF_3$.

In embodiments of the compounds of Formula I and Ia, $R^3$ is selected from the group consisting of H and $CH_3$; and $R^4$ is selected from the group consisting of H, —C(=O)OH, and —C(=O)O$C_1$-$C_3$alkyl.

In embodiments of the compounds of Formula I and Ia, $R^5$ is selected from the group consisting of H and $CH_3$; and $R^6$ and $R^7$ are H.

In embodiments of the compounds of formula I and Ia, $R^W$ is —CH($CH_3$)$_2$.

In embodiments of the compounds of formula I and Ia, $D^2$ is a cyclic group selected from phenyl, indolyl, imidazolyl, cyclopropyl, $C_4$-$C_7$ cycloalkyl which is optionally fused to a phenyl, $C_5$-$C_6$ cycloalkenyl, and a 6-7-membered cyclic monoether or diether fused to a phenyl, wherein $D^2$ is optionally substituted with 1-3 substituents independently selected from halogen, $C_1$-$C_3$ alkyl, $CF_3$, —$OCH_3$, —$OCF_3$, —$CO_2H$, —$CO_2CH_3$, —$NO_2$, —OH, and $C_1$-$C_2$alkylene-O—$C_1$-$C_4$alkyl optionally substituted with 1-9 F, and is optionally substituted with one substituent selected from 4,4,5,5-tetramethyl-1,3,2-dioxaborolan-2-yl and $D^4$, wherein $D^4$ is connected directly to $D^2$ or is connected to $D^2$ through a linking group $L^4$.

In embodiments of the compounds of formula I and Ia, $D^4$ is a cyclic group selected from phenyl, $C_5$-$C_6$ cycloalkyl, $C_5$-$C_6$ cycloalkenyl, pyrrolidinyl, piperidinyl, piperazinyl, thiazolyl, pyrazolyl, furanyl, pyridyl, indolyl, benzothiophenyl, benzofuranyl, and naphthyl, wherein $D^4$ is optionally substituted with 1-3 substituents independently selected from $C_1$-$C_5$ alkyl, $CF_3$, $C_2$-$C_6$ alkenyl, —$OC_1$-$C_4$alkyl, —$OCF_3$, halogen, —$CO_2H$, —$CO_2C_1$-$C_5$alkyl, —CN, and OH, and is optionally substituted with one group $D^6$, which is optionally connected directly to $D^4$ or is connected to $D^4$ through a linking group $L^6$.

In embodiments of the compounds of formula I and Ia, $D^6$ is selected from the group consisting of phenyl, $C_3$-$C_6$ cycloalkyl, pyridyl, morpholinyl, pyrrolidinyl, furanyl, 2-oxazolidinonyl and 2-azetidinonyl, wherein $D^6$ is optionally substituted with 1-2 substituents independently selected from $C_1$-$C_3$alkyl, $CF_3$, —$OC_1$-$C_3$alkyl, —$OCF_3$, Cl, and F.

In embodiments of the compounds of formula I and Ia, $L^4$ is selected from the group consisting of $CH_2$—, —O—, —C(=O)—, —$CH_2CH_2NHCH_2$—, —$CH_2C$(=O)NH— and $C_2$-$C_3$ alkenylene.

In embodiments of the compounds of formula I and Ia, $L^6$ is selected from —S(O)$_2$— and $C_2$-$C_3$ alkenylene.

In embodiments of the compounds of formula I and Ia, $D^5$ is selected from the group consisting of $C_2$-$C_3$ alkynyl and $C_1$-$C_{12}$ alkyl, wherein $C_1$-$C_{12}$alkyl is optionally substituted with 1-3F.

DEFINITIONS

"Ac" is acetyl, which is $CH_3C$(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated (e.g., cycloalkyl may be defined as having one or more double bonds). The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"EDC" is 1-ethyl-3-(3-dimethylaminopropyl)carbodiimide.

"Heterocyclyl," "heterocycle," and "heterocyclic" means a fully or partially saturated or aromatic 5-6 membered ring containing 1-4 heteroatoms independently selected from N, S and O, unless otherwise stated.

"Benzoheterocycle" represents a phenyl ring fused to a 5-6-membered heterocyclic ring having 1-2 heteroatoms, each of which is O, N, or S, where the heterocyclic ring may be saturated or unsaturated. Examples include indole, benzofuran, 2,3-dihydrobenzofuran and quinoline.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"Weinreb amine" is N,O-dimethylhydroxylamine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to include all such stereoisomeric forms of the compounds of Formula I and all mixtures of stereoisomers. When structures are shown without a stereochemical representation, all stereochemical structures are included individually and collectively, such as enantiomers, diastereomers (where diastereomers are possible), and mixtures of the enantiomers and/or diastereomers, including racemic mixtures. When a stereochemical structure of a compound is provided, any reference to stereoisomers of the compound includes other enantiomers, diastereomers (when possible), and mixtures of these, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are particularly effective in raising HDL-C and/or increasing the ratio of HDL-C to LDL-C. The compounds are also effective in lowering LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other thereapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD-4522.

Finally compounds of this invention can be used with compounds that are useful for treating other diseases, such as diabetes, hypertension and obesity, as well as other anti-atherosclerostic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and 133 adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) a minorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining $IC_{50}$'s to identify compounds that are CETP inhibitors was performed based on a modification of the method described by Epps et al. employing BODIPY®-CE as the cholesteryl lipid donor and BODIPY®-TG as the triglyceride lipid donor. See Epps et al. (1995) *Method for measuring the activities of cholesteryl ester transfer protein (lipid transfer protein)*, Chem. Phys. Lipids. 77, 51-63.

Particles used in the assay were created from the following materials by probe sonication essentially as described by Epps et al. Synthetic cholesteryl ester (CE) donor HDL particles contained DOPC (Dioleoyl Phosphatidyl Choline), BODIPY®-CE (Molecular Probes C-3927), triolein (a triglyceride), dabcyl dicetylamide, (a non-diffusable quencher molecule to reduce background fluorescence) and apoHDL. Synthetic triglyceride (TG) donor HDL particles contained DOPC, BODIPY®-TG, and apoHDL. BODIPY®-TG was synthesized at room temperature from diolein and the BODIPY containing fatty acid analog 4,4-difluoro-5-(2-thienyl)-4-bora-3a,4a-diaza-s-indacene-3-dodecanoic acid (Molecular Probes) in methylene chloride in the presence of dicyclohexyl carbodiimide. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), 3% human serum, and half the final concentration of acceptor particles was prepared, and 100 µL of the assay cocktail was added to each well of the plate. Test compounds in DMSO were added in a volume of 3 pt. The plate was mixed on a plate shaker and then incubated at 25° C. for 1 hour. A second assay cocktail containing donor particles, the remaining acceptor particles and 1×CETP buffer was prepared. 47 µL of the second assay cocktail was added to the reaction wells to start the assay. Assays were performed in a final volume of 150 µL. CE transfer reactions were performed as follows: final concentrations of materials were: 2.5 ng/µL CE donor particles, 7.5 ng/µL acceptor particles (each expressed by protein content), 1×CETP buffer, 14-30 nM recombinant human CETP (expressed in CHO cells and partially purified), and up to 2% DMSO when testing compounds; reactions were followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well. TG transfer reactions were performed as described above with the exception that 2.5 ng/uL TG donor particles were used. TG transfer was measured at an excitation wavelength of 538 nm while reading emission at 568 nm every 45 sec for 45 min at 37° C. with a cutoff filter at 550 nm.

Data were evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate 1050.

EXAMPLES

The following schemes and examples are provided so that the invention will be more fully appreciated and understood. Starting materials are made using known procedures or as shown below.

The examples should not be construed as limiting the invention in any way. The scope of the invention is defined by the appended claims. Compounds of this invention have an $IC_{50}$ value as measured for the CE transfer reaction as described above of less than or equal to 14 µM. $IC_{50}$ values are in the range of 17 nM to 14 µM. Most of the compounds have an $IC_{50}$ value of 17 nM to 200 nM, and the preferred compounds generally have $IC_{50}$ values of 17 nM to 100 nM. The following compounds, or stereoisomers of the compounds, have $IC_{50}$ values in the range of 12 nM-41 nM: 44, 45, 47, 48, 53, 64, 65, 76, 81, and 82.

INTERMEDIATE 1

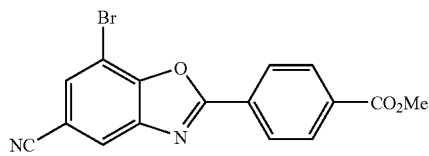

Methyl 4-(7-bromo-5-cyano-1,3-benzoxazol-2-yl)benzoate

Step A. 3-Bromo-4-hydroxy-5-nitrobenzonitrile

To a 5-L, 3-neck round-bottom flask fitted with a thermocouple, stirring paddle, and nitrogen line were added 3,5-dibromo-4-hydroxybenzonitrile (95 g) and glacial acetic acid (3.3 L). Sodium nitrite (120 g) was then added in small portions. The mixture was heated to 50° C. and stirred overnight at this temperature. The mixture was then allowed to cool and poured into a large extractor containing water (10 L). Ethyl acetate (10 L) was added and the layers were separated. The aqueous layer was extracted with ethyl acetate (4 L) and the combined organic layers were washed with water and brine, and then dried over magnesium sulfate and concentrated in vacuo to provide 96.9 g of the desired product. Mass spectrum (ESI) 243.0 (M+).

Step B. 3-Amino-5-bromo-4-hydroxybenzonitrile

To a 22-L, 3-neck round-bottom flask fitted with a stirring paddle, a Claisen adapter fitted with a thermocouple and a condenser blanketed with nitrogen, and an addition funnel capped with a septum was added a mixture of 3-bromo-4-hydroxy-5-nitrobenzonitrile (96.9 g, Step A) in methanol (14 L). To this mixture was added iron (III) chloride (9.3 g) and activated charcoal (38 g, Darco 6-60, 100-mesh powder). The mixture was heated to reflux (65° C.) and stirred for 15 min at this temperature. Hydrazine (80 ml) was added to the refluxing mixture dropwise via addition funnel. Once the addition was complete, the mixture was stirred at reflux for 2 h. The mixture was then allowed to cool, filtered through Celite, washing with methanol, and concentrated to a red oil. A mixture of 300 ml of acetic acid and 700 ml of methanol was added and the mixture was concentrated again and then co-concentrated twice with 800 ml of toluene. The residue was purified by flash chromatography on an Isco Companion XL, 1.5 kg column, eluting with 3 column volumes of 30% EtOAc in hexanes, followed by a linear gradient of EtOAc in hexanes from 30 to 60% over 6 column volumes, followed by 2 column volumes of 60% EtOAc in hexanes to provide 40 g (55%) of the title compound. Mass spectrum (ESI) 214.9 (M+1).

Step C. Methyl 4-(7-bromo-5-cyano-1,3-benzoxazol-2-yl)benzoate

To a 3-L round-bottom flask fitted with a stir bar and a Claisen adapter fitted with a thermocouple and a condenser blanketed with nitrogen was added terephthalic acid monomethyl ester chloride (37.3 g) and a solution of 3-amino-5-bromo-4-hydroxybenzonitrile (40 g, Step B) in dioxane (675 ml). The mixture was heated to reflux and stirred at this temperature overnight. The mixture was then cooled to room temperature and the dioxane was removed in vacuo. The flask was fitted with a Dean-Stark trap and p-toluenesulfonic acid monohydrate (35.8 g) and toluene (2.5 L) were added. The mixture was heated to reflux and stirred at this temperature overnight. The mixture was then allowed to cool, transferred to a new 5-L flask, and concentrated to a brown solid. The crude product was triturated with methanol to provide 55.5 g (83%) of the title compound. $^1$H NMR (500 MHz, DMSO-d$_6$): δ 8.50 (s, 1H), 8.34 (d, J=8.0 Hz, 2H), 8.29 (s, 1H), 8.19 (d, J=8.0 Hz, 2H), 3.91 (s, 3H).

INTERMEDIATE 2

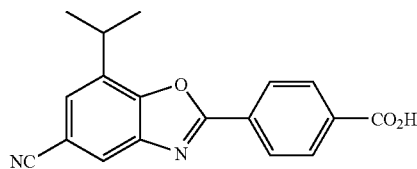

4-(5-Cyano-7-isopropyl-1,3-benzoxazol-2-yl)benzoic acid

Step A. Methyl 4-(5-cyano-7-isopropenyl-1,3-benzoxazol-2-yl)benzoate

To a 5-L, 3-neck round-bottom flask fitted with a stirring paddle, a condenser blanketed with nitrogen, and a thermocouple, was added 4-(7-bromo-5-cyano-1,3-benzoxazol-2-yl)benzoate (55.5 g, INTERMEDIATE 1) toluene (2 L), water (375 ml), ethanol (150 ml), 2M aqueous sodium carbonate (250 ml), and isopropenylboronic acid (83.4 g, INTERMEDIATE 3). The mixture was purged with nitrogen three times and then tetrakis(triphenylphosphine)palladium (0) (9.1 g) was added, and the mixture was purged three times with nitrogen. The mixture was heated to reflux (91° C.) and stirred at this temperature overnight. The mixture was then cooled to 20° C. and the product was filtered, washed with water, dried, and transferred to a 3-L round-bottom flask and rinsed with toluene (1 L). Residual solvent was removed in vacuo. Mass spectrum (ESI) 319.1 (M+1).

Step B. Methyl 4-(5-cyano-7-isopropyl-1,3-benzoxazol-2-yl)benzoate

To a 5-gallon reaction vessel was added methyl 4-(5-cyano-7-isopropenyl-1,3-benzoxazol-2-yl)benzoate (40.6 g, Step A), tetrahydrofuran (4 L), and 10% palladium on carbon (8 g). The reaction mixture was heated to 60° C. under 10 psi of hydrogen for 3 h, and then filtered through Celite, washing generously with dichloromethane. Concentration of the eluent in vacuo provided 40.5 g (99%) of the title compound. Mass spectrum (ESI) 321.1 (M+).

Step C. 4-(5-Cyano-7-isopropyl-1,3-benzoxazol-2-yl)benzoic acid

To a 5-L, round-bottom flask fitted with a stir bar and a Claisen adapter fitted with a thermocouple and a nitrogen line was added was added methyl 4-(5-cyano-7-isopropyl-1,3-benzoxazol-2-yl)benzoate (40.5 g, Step B) tetrahydrofuran (1.25 L), methanol (630 ml), water (315 ml), and lithium hydroxide monohydrate (10.7 g). The mixture was heated to 50° C. and stirred at this temperature for 1 h. The mixture was then cooled and concentrated to a thick slurry. 1N HCl (3.2 L) was added and an off-white solid formed. The mixture was stirred for 5 min and then filtered, washing with water (2×500 ml). The solid was transferred to a 2-L round-bottom flask, concentrated from toluene (1 L) and then dried in vacuo. Mass spectrum (ESI) 307.0 (M+1). $^1$H NMR (500 MHz, DMSO-d$_6$): δ 8.69 (d, J=7.5 Hz, 2H), 8.28 (s, 1H), 8.16 (d, J=8.0 Hz, 2H), 7.81 (s, 1H), 3.46 (septet, J=6.5 Hz, 1H), 1.40 (d, H=7.0 Hz, 6H).

INTERMEDIATE 3

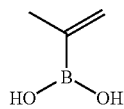

Isopropenylboronic acid

To a 12-L, 3-neck round-bottom flask fitted with a stirring paddle, an addition funnel capped with a septum, and a Claisen adapter fitted with a thermocouple and a nitrogen line was added trimethyl borate (405 ml) and tetrahydrofuran (2.4 L). To this solution was added isopropenylmagnesium bromide (2.4 L of a 0.5 M solution in tetrahydrofuran) via the addition funnel, keeping the temperature below 30° C. using an ice-water bath. Upon completion of the addition, the mixture was stirred for 3 h at room temperature. The reaction mixture was poured into a large extractor containing 1 N HCl (4 L). Ether (4 L) was added, the layers were separated, and the aqueous layer was extracted with ether (2 L). The combined organic layers were dried over magnesium sulfate and concentrated in vacuo, keeping the temperature below 30° C., to provide 197.3 g of the title compound. $^1$H NMR (500 MHz, CDCl$_3$): δ 6.13 (s, 1H); 5.84 (s, 1H); 5.63 (app. d, J=12.1 Hz, 2H); 4.38 (br. s, 1H); 1.87 (app. d, J=21.7 Hz, 6H).

Example 1

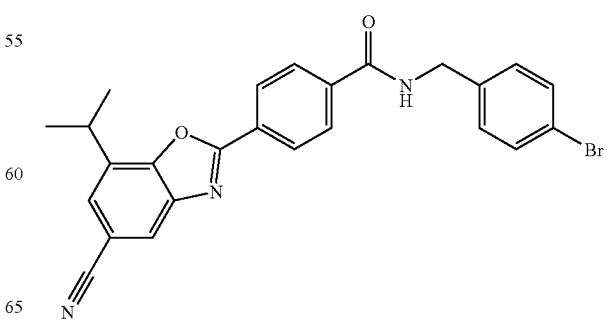

N-(4-Bromobenzyl)-4-(5-cyano-7-isopropyl-1,3-benzoxazol-2-yl)benzamide

To 35 ml of dichloromethane was added 4-(5-cyano-7-isopropyl-1,3-benzoxazol-2-yl)benzoic acid (306 mg, INTERMEDIATE 2). To this mixture was added 1.5 ml of a 2M solution of oxalyl chloride in dichloromethane followed by 80 μl of dimethylformamide. The mixture was stirred at room temperature for 0.5 hours. The mixture was then concentrated in vacuo with minimal or no heating (<30° C.), and dried under high-vacuum to remove traces of solvent. To this residue was then added 10 ml of dichloromethane, 186 mg of ({1-[4-(trifluoromethyl)pyrimidin-2-yl]piperidin-4-yl}methyl)amine, and 1.05 ml of diisopropylethylamine. The mixture was stirred for 15 min, and then transferred directly to a Biotage 65i column for purification via flash chromatography, eluting 1 column volume of 100% hexanes followed by a gradient of 0 to 100% ethyl acetate in hexanes over 10 column volume, followed by 100% ethyl acetate for 4 column volumes, to provide the title compound (389 mg, 82%). Mass spectrum (ESI) 475.9 (M+2). $^1$H NMR (500 MHz, CDCl$_3$): δ 8.34 (d, J=8.5 Hz, 2H), 7.97 (d, J=8.5 Hz, 2H), 7.94 (s, 1H), 7.51 (s, 1H), 7.50 (d, J=8.4 Hz, 2H), 7.28 (d, J=8.4 Hz, 2H), 6.49 (bs, 1H), 4.64 (d, J=5.9 Hz, 2H), 3.48 (sept, J=7.0 Hz, 1H), 1.46 (d, J=6.9 Hz, 6H).

Example 2

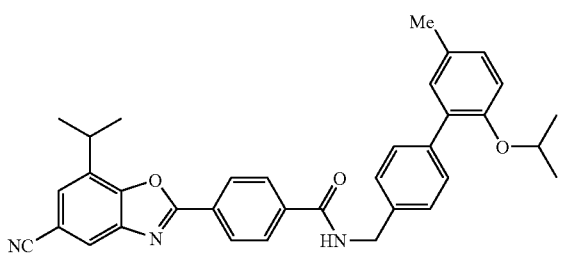

4-(5-cyano-7-isopropyl-1,3-benzoxazol-2-yl)-N-[(2'-isopropoxy-5'-methylbiphenyl-4-yl)methyl]benzamide Sodium carbonate (100 μl of a 2M aqueous solution), (2-isopropoxy-5-methylphenyl)boronic acid (19 mg), and N-(4-bromobenzyl)-4-(5-cyano-7-isopropyl-1,3-benzoxazol-2-yl)benzamide (24 mg, EXAMPLE 1) were dissolved in toluene (2.1 ml), water (0.6 ml) and ethanol (0.3 ml). To this solution was added tetrakis(triphenylphosphine)palladium (0) (9 mg). The mixture was heated to 150° C. for 25 min via microwave. Upon cooling, the mixture was concentrated in vacuo and then dissolved in dichloromethane (5 ml). The sample was transferred to a Biotage 40M column and purified via flash chromatography, eluting 1 column volume of 100% hexanes followed by a gradient of 0 to 100% ethyl acetate in hexanes over 10 column volume, followed by 100% ethyl acetate for 4 column volumes, to provide the title compound. Mass spectrum (ESI) 544.2 (M+1). $^1$H NMR (500 MHz, CDCl$_3$): δ 8.35 (d, J=8.4 Hz, 2H), 8.00 (d, J=8.2 Hz, 2H), 7.94 (s, 1H), 7.58 (d, J=8.0 Hz, 2H), 7.52 (d, J=8.0 Hz, 2H), 7.40 (d, J=8.0 Hz, 2H), 7.13 (s, 1H), 7.09 (d, J=8.2 Hz, 1H), 6.90 (d, J=8.4 Hz, 2H), 6.47 (t, J=4.6 Hz, 1H), 4.73 (d, J=5.5 Hz, 3H), 4.40 (sept, J=6.2 Hz, 1H), 3.48 (sept, J=7.1 Hz, 1H), 2.32 (s, 3H), 1.46 (d, J=6.9 Hz, 6H), 1.24 (d, J=5.9 Hz, 6H).

Example 3

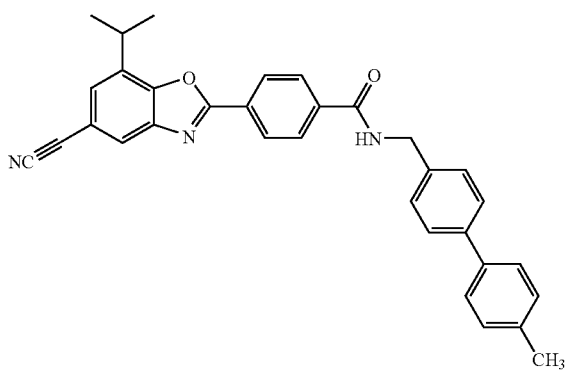

4-(5-Cyano-7-isopropyl-1,3-benzoxazol-2-yl)-N-[(4'-methylbiphenyl-4-yl)methyl]benzamide To a solution of N-(4-bromobenzyl)-4-(5-cyano-7-isopropyl-1,3-benzoxazol-2-yl)benzamide (30 mg, EXAMPLE 1) in toluene (1 ml), water (0.5 ml), and ethanol (0.25 ml) was added (4-methylphenyl)boronic acid (30 mg), 2M aqueous potassium carbonate (1 ml), and tetrakis(triphenylphosphine)palladium(0) (5 mg). The solution was sealed in a microwave tube and heated to 150° C. for 60 min in a microwave reactor. The mixture was then diluted with ethyl acetate (10 ml) and water (10 ml). The phases were separated and the aqueous phase was extracted with ethyl acetate (10 ml). The combined organic phases were washed with brine (10 ml), dried (sodium sulfate), and concentrated. The residue was purified by flash chromatography on a Biotage Horizon, 25M column, eluting with 1 column volume of 2% ethyl acetate in hexanes, followed by a linear gradient of ethyl acetate in hexanes from 2 to 100% over 10 column volumes to provide the title compound (10 mg, 33%). Mass spectrum (ESI) 486.1 (M+1). NMR (500 MHz, CDCl$_3$): δ 8.34 (s, 1H), 8.32 (s, 1H), 7.99 (s, 1H), 7.98 (s, 1H), 7.93 (d, J=1.5 Hz, 1H), 7.59 (s, 1H), 7.58 (s, 1H), 7.51 (s, 1H), 7.49 (s, 1H), 7.47 (s, 1H), 7.45 (s, 1H), 7.43 (s, 1H), 7.24 (s, 1H), 6.58-6.56 (app t, J=10.5, 1H), 4.72 (d, J=5.5 Hz, 2H), 3.44-3.50 (m, 1H), 2.40 (s, 3H), 1.45 (d, J=6.5 Hz, 6H).

Example 4

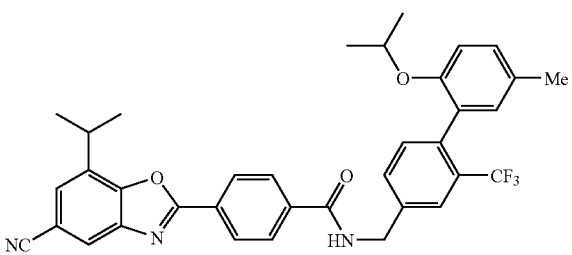

4-(5-cyano-7-isopropyl-1,3-benzoxazol-2-yl)-N-{[2'-isopropoxy-5'-methyl-2-(trifluoromethyl)biphenyl-4-yl]methyl}benzamide The title compound was prepared from N-[4-chloro-3-(trifluoromethyl)benzyl]-4-(5-cyano-7-isopropyl-1,3-benzoxazol-2-yl)benzamide (EXAMPLE 7) following the procedure described in EXAMPLE 2. Mass spectrum (ESI) 612.2 (M+1). NMR (500 MHz, CDCl₃): δ 8.35 (d, J=8.3 Hz, 2H), 8.01 (d, J=8.2 Hz, 2H), 7.94 (s, 1H), 7.58 (m, 4H), 7.18 (m, 2H), 6.97 (d, J=8.1 Hz, 1H), 6.48 (t, J=5.0 Hz, 1H), 4.91 (d, J=5.2 Hz, 3H), 4.51 (sept, J=6.1 Hz, 1H), 3.48 (sept, J=7.1 Hz, 1H), 2.38 (s, 3H), 1.46 (d, J=7.0, 6H), 1.29 (d, J=6.0, 6H).

Example 5

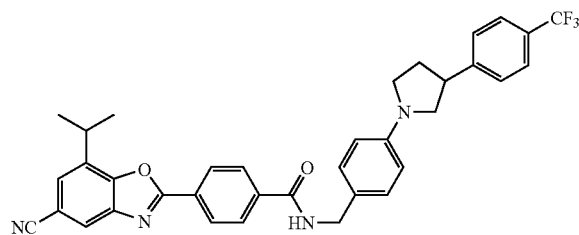

4-(5-cyano-7-isopropyl-1,3-benzoxazol-2-yl)-N-(4-{3-[4-(trifluoromethyl)phenyl]pyrrolidin-1-yl}benzyl)benzamide Sodium tert-butoxide (10 mg), N-(4-bromobenzyl)-4-(5-cyano-7-isopropyl-1,3-benzoxazol-2-yl)benzamide (24 mg, EXAMPLE 1), and 3-[4-(trifluoromethyl)phenyl]pyrrolidine (31 mg) were dissolved in toluene (5.0 mL). To this mixture was added bispalladiumtribenzylidene acetone (10 mg) and 1,1'-binaphthalene-2,2'-diylbis(diphenylphosphine) (12 mg). The mixture was heated to 150° C. for 25 min in a microwave reactor. Upon cooling, the mixture was then concentrated in vacuo, taken up in dichloromethane, and purified via flash chromatography on a Biotage Horizon, 40 M column, eluting with 1 column volume of 100% hexanes, followed by a linear gradient of ethyl acetate in hexanes from 0 to 100% over 10 column volumes, followed by 4 column volumes of 100% ethyl acetate to provide the title compound (16 mg, 53%). Mass spectrum (ESI) 609.1 (M+1). ¹H NMR (500 MHz, CDCl₃): δ 8.31 (d, J=8.5 Hz, 2H), 7.95 (d, J=8.5 Hz, 2H), 7.94 (s, 1H), 7.59 (d, J=8.0 Hz, 2H), 7.51 (s, 1H), 7.39 (d, J=8.0 Hz, 2H), 7.29 (d, J=8.4 Hz, 2H), 6.60 (d, J=8.4 Hz, 2H), 6.33 (t, J=4.0 Hz, 1H), 4.59 (d, J=5.3 Hz, 2H), 3.75 (t, J=8.4 Hz, 1H), 3.57 (m, 5H), 2.47 (m, 1H), 2.15 (m, 1H), 1.46 (d, J=6.9, 6H).

Example 6

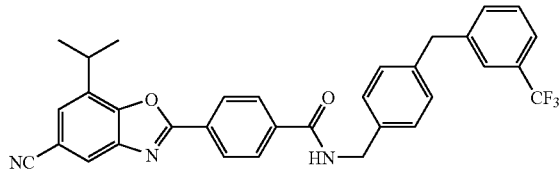

4-(5-cyano-7-isopropyl-1,3-benzoxazol-2-yl)-N-{4-[3-(trifluoromethyl)benzyl]benzyl}benzamide The title compound was prepared from 4-(5-cyano-7-isopropyl-1,3-benzoxazol-2-yl)-N-[4-(4,4,5,5-tetramethyl-1,3,2-dioxaborolan-2-yl)benzyl]benzamide (26 mg, EXAMPLE 8) and 1-(bromomethyl)-3-(trifluoromethyl)benzene (24 mg) following the procedure described in EXAMPLE 3 (26 mg, 93%) Mass spectrum (ESI) 554.2 (M+1). ¹H NMR (500 MHz, CDCl₃): δ 8.33 (d, J=8.2 Hz, 2H), 7.97 (d, J=8.3 Hz, 2H), 7.94 (s, 1H), 7.51 (s, 1H), 7.41 (m, 4H), 7.33 (d, J=8.0 Hz, 2H), 7.20 (d, J=7.8 Hz, 2H), 6.42 (bs, 1H), 4.67 (d, J=5.5 Hz, 2H), 4.04 (s, 2H), 3.38 (sept, J=6.9 Hz, 1H), 1.46 (d, J=6.8, 6H).

Following the procedures described in EXAMPLES 1-6, the compounds listed in Table 1 were prepared. The symbol "X₁" on each substituent group shows the point of attachment of the substituent group to the structure at the top of the table.

TABLE 1

| EXAMPLE | R | MS (M + 1) |
|---|---|---|
| 7 | ![Cl, CF3 benzyl group with X1] | 498.1 |
| 8 | ![pinacol boronate benzyl group with X1] | 522.2 |
| 9 | ![2-chlorobiphenyl methyl group with X1] | 506.1 |

TABLE 1-continued
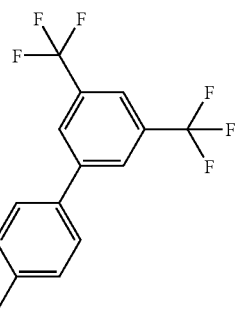
| EXAMPLE | R | MS (M + 1) |
|---|---|---|
| 10 | 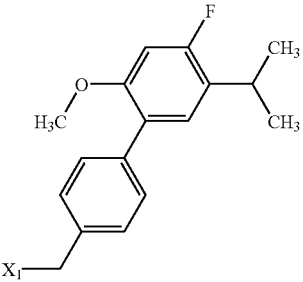 | 608.1 |
| 11 | 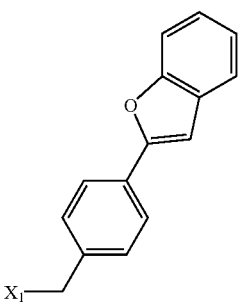 | 562.3 |
| 12 | 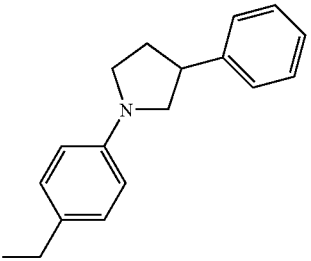 | 512.1 |
| 13 | 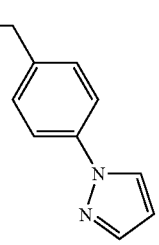 | 541.3 |
TABLE 1-continued
| EXAMPLE | R | MS (M + 1) |
|---|---|---|
| 14 | 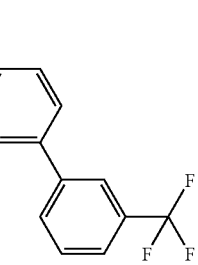 | 462.1 |
| 15 | | 556.2 |
| 16 | | 500.2 |
| 17 | | 540.1 |

TABLE 1-continued
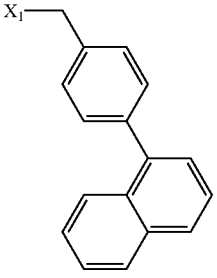
| EXAMPLE | R | MS (M + 1) |
|---|---|---|
| 18 | 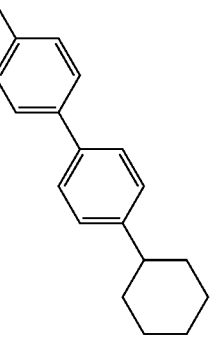 | 522.2 |
| 19 | 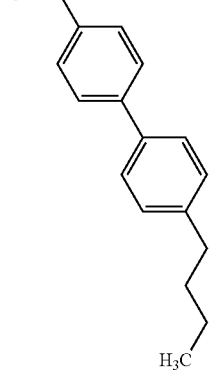 | 554.1 |
| 20 | 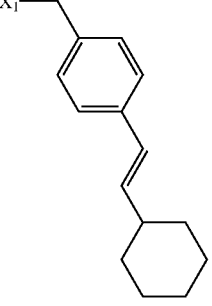 | 528.2 |
| 21 | 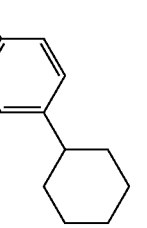 | 504.2 |
| 22 | 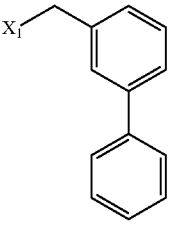 | 478.2 |
| 23 | 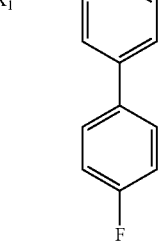 | 472.1 |
| 24 | 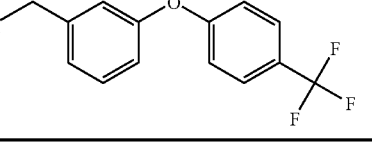 | 490.1 |
| 25 | | 556.0 |
Example 26
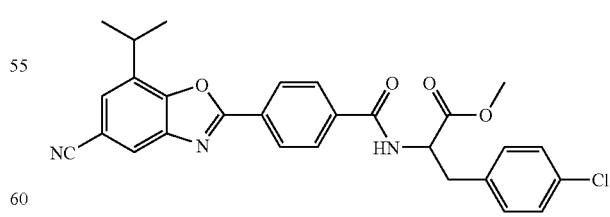
Methyl-3-(4-chlorophenyl)-2-{[4-(5-cyano-7-isopropyl-1,3-benzoxazol-2-yl)benzoyl]amino}propanoate
At room temperature, a 2-dram vial, equipped with a magnetic stirrer was charged with 4-(5-cyano-7-isopropyl-1,3- benzoxazol-2-yl)benzoic acid (153 mg, 0.5 mmol, INTERMEDIATE 2), DL-4-chlorophenylalanine methyl ester hydrochloride (125 mg, 0.5 mmol), bromotrispyrrolidinophosphonium hexafluorophosphate (233 mg, 0.5 mmol) and 5 ml of dimethylformamide. To this was added diisopropylethylamine (524 µl, 3 mmol) dropwise, during which addition the reaction turned a reddish-orange. After a few minutes the reaction mixture faded to a pale yellow clear solution. The reaction mixture was allowed to stir at room temperature for 3 d. The residue was purified by chromatography using a Biotage SP1, 40M silica cartridge, eluting with a linear gradient of hexanes in ethyl acetate from 20% to 100% over 15 column volumes to provide the title compound as a white solid (150 mg). Mass spectrum (ESI) 502.2 (M+1). $^1$H NMR (600 MHz, CDCl$_3$): δ 8.31 (d, J=8.2 Hz, 2H), 7.93 (d, J=1.2 Hz, 1H), 7.89 (d, J=8.4 Hz, 2H), 7.5 (s, 1H), 7.26 (d, J=8.2 Hz, 2H), 7.1 (d, J=8.3 Hz, 2H), 6.66 (d, J=7.3 Hz, 1H), 3.79 (s, 1H), 3.46 (m, 1H), 3.3 (dd, J=5.9, 5.9 Hz, 1H), 3.21 (dd, J=5.2, 5.0 Hz, 1H), 1.44 (J=6.9 Hz, 6H).

Following the procedures described in EXAMPLE 26, the compounds listed in Table 2 were prepared:

TABLE 2

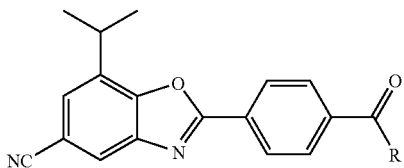

| EXAMPLE | R | MS (M + 1) |
|---|---|---|
| 27 | (methyl tryptophan ester) | 507.2 |
| 28 | (methyl N-benzylhistidine ester) | 548.3 |
| 29 | (methyl valine ester, NH) | 420.7 (rac) |
| 30 | (methyl valine ester, NH, S) | 420.2 (S) |
| 31 | (methyl α-aminoisobutyrate) | 406.7 |
| 32 | (methyl propargylglycine ester) | 516.7 |
| 33 | (methyl 1-aminocyclopropanecarboxylate) | 404.1 |

Example 34

2-{[4-(5-cyano-7-isopropyl-1,3-benzoxazol-2-yl)benzoyl]amino}-3-methylbutanoic acid The title compound was prepared from methyl-2-{[4-(5-cyano-7-isopropyl-1,3-benzoxazol-2-yl)benzoyl]amino}-3-methylbutanoate (EXAMPLE 29) using procedure analogous to that described in INTERMEDIATE 2, Step C. Mass spectrum (ESI) 406.20 (M+1). $^1$H NMR (500 MHz, CDCl$_3$): δ 8.19 (d, J=8.4 Hz, 2H), 7.89 (d, J=8.4 Hz, 2H), 7.79 (d, J=1.4 Hz, 1H), 7.38 (s, 1H), 7.02 (d, J=8.4 Hz, 2H), 4.59 (m, 1H), 3.45 (m, 1H), 2.2 m, 1H), 1.32 (d, J=7.10 Hz, 6H), 0.91 (t, J=6.3 Hz, 6H).

Example 35

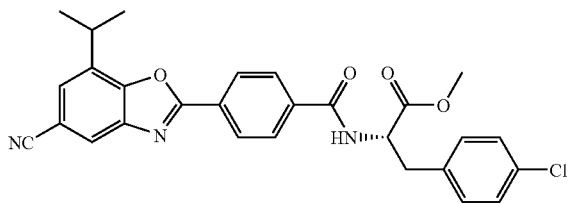

Methyl(2S)-3-(4-chlorophenyl)-2-{[4-(5-cyano-7-isopropyl-1,3-benzoxazol-2-yl)benzoyl]amino}propanoate Methyl (2S)-2-[(tert-butoxycarbonyl)amino]-3-(4-chlorophenyl)propanoate (INTERMEDIATE 4) was treated with 5 mL of TFA/water [95:5] for 2 h. The reaction mixture was poured onto crushed ice and basified with potassium carbonate. The product was extracted with dichloromethane and the combined organics were dried over magnesium sulfate, filtered and concentrated in vacuo to provide crude methyl (2S)-2-[(tert-butoxycarbonyl)amino]-3-(4-chlorophenyl)propanoate. This compound and 4-(5-cyano-7-isopropyl-1,3-benzoxazol-2-yl)benzoic acid (INTERMEDIATE 2) were coupled following the procedure described in EXAMPLE 1 to provide the title compound. Mass spectrum (ESI) 502.2 (M+1). $^1$H NMR (600 MHz, CDCl$_3$): δ 8.31 (d, J=8.4 Hz, 2H), 7.92 (d, J=1.4 Hz, 1H), 7.88 (d, J=8.4 Hz, 2H), 7.5 (s, 1H), 7.25 (d, J=8.3 Hz, 2H), 7.06 (d, J=8.4 Hz, 2H), 6.68 (d, J=7.3 Hz, 1H), 5.07 (m, 1H), 3.45 (m, H), 3.3 (dd, J=5.9, 5.9 Hz, 1H), 3.21 (dd, J=5.2, 5.2 Hz, 1H), 1.44 (d, J=7.0 Hz, 6H).

INTERMEDIATE 4

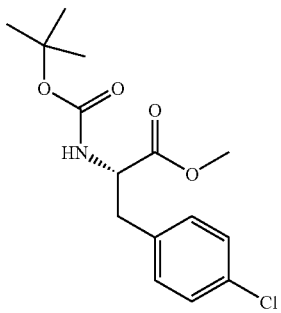

Methyl(2S)-2-[(tert-butoxycarbonyl)amino]-3-(4-chlorophenyl)propanoate

To a 250 mL round bottom flask was added N-Boc-4-chloro-L-phenylalanine (0.971 g, 3.24 mmol), potassium carbonate (0.448 g, 3.24 mmol), a stir bar and 30 ml of acetone. To this was added dimethyl sulfate (0.613 ml, 6.48 mmol) and the reaction was allowed to proceed at ambient temperature for 36 h. The reaction was quenched with water (15 ml), and the product was extracted with ethyl acetate (4×100 ml). The organics were pooled, washed with brine, and dried over sodium sulfate. The organics were filtered and concentrated in vacuo to provide a pale yellow residue. The residue was purified by column chromatography on a Biotage SP1, 40M Biotage silica cartridge, eluting with a linear gradient of hexanes-ethyl acetate to provide the title compound as a pale yellow foam (950 mg). Mass spectrum (ESI) 214.1 (M-Boc). $^1$H NMR (600 MHz, CDCl$_3$): δ 7.24 (d, J=8.3 Hz, 2H), 7.06 (d, J=8.1 Hz, 1H), 4.96 (d, J=7 Hz, 1H), 4.56 (d, J=6 Hz, 1H), 3.71 (s, 3H), 3.08 (dd, J=5.7, 5.7 Hz, 2H), 3.01 (dd, J=5.9, 6.0 Hz, 1H), 1.42 (s, 9H).

Example 36

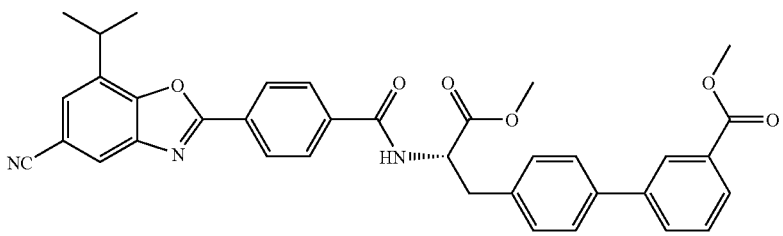

4'-((2S)-2-{[4-(5-cyano-7-isopropyl-1,3-benzoxazol-2-yl)benzoyl]amino}-3-methoxy-3-oxopropyl)biphenyl-3-carboxylate A microwave vial equipped with a stir bar was charged with methyl (2S)-3-(4-chlorophenyl)-2-{[4-(5-cyano-7-isopropyl-1,3-benzoxazol-2-yl)benzoyl]amino}propanoate (EXAMPLE 35), (1),3-methoxycarbonylphenylboronic acid (32 mg, 0.179 mmol), potassium carbonate (25 mg, 0.179 mmol), 1,1-bis(di-t-butylphosphino)palladium dichloride (3.9 mg, 0.006 mmol), 400 µl of tetrahydrofuran, and 400 µl of water. The vial was crimped shut and microwaved at 100° C. for 12 min. The crude reaction mixture was diluted with 5 ml of ethyl acetate and applied to a pad of silica. The silica pad was washed with ethyl acetate (15 ml). The filtrate was concentrated and the residue was purified by flash chromatography on a Biotage SP1, 25S column, eluting with a linear gradient of hexanes-ethyl acetate from 0% to 100% over 20 column volumes to give the title compound as an off white solid (35 mg). Mass spectrum (ESI) 502.2 (M+1). $^1$H NMR (600 MHz, CDCl$_3$): δ 8.31 (d, J=8.4 Hz, 2H), 8.25 (m, H), 7.99 (, J=7.7 Hz, 1H), 7.92 (d, J=1.9 Hz, 1H), 7.91 (d, J=8.4 Hz, 2H), 7.7 (d, J=1.7 Hz, 1H), 7.56 (d, J=8.2 Hz, 2H), 7.94 (m, 1H), 7.22 (d, J=8.2 Hz, 2H), 6.69 (d, J=7.4 Hz, 1H), 5.14 (m, 1H), 3.93 (s, 3H), 3.82 (s, 3H), 3.45 (m, 1H), 3.38 (dd, J=5.7, 5.9 Hz, 1H), 3.3 (dd, J=5.4, 5.2 Hz, 1H), 1.43 (d, J=7 Hz, 6H).

Following the procedure described in EXAMPLE 36, the compounds listed in Table 3 were prepared:

TABLE 3

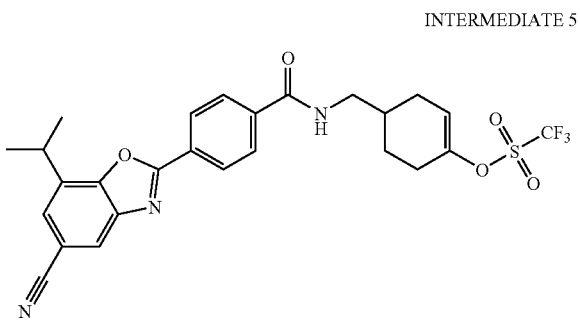 [SMILES: CC(C)c1cc(C#N)cc2nc(-c3ccc(C(=O)NCC4CC=C(OS(=O)(=O)C(F)(F)F)CC4)cc3)oc12]

| EXAMPLE | R | MS (M + 1) |
|---|---|---|
| 37 | 3-cyanophenyl | 569.2 |
| 38 | 3-trifluoromethylphenyl | 612.2 |
| 39 | 3,4-dimethylphenyl | 572.3 |
| 40 | 3,5-difluoro-4-methoxyphenyl | 610.2 |

INTERMEDIATE 5

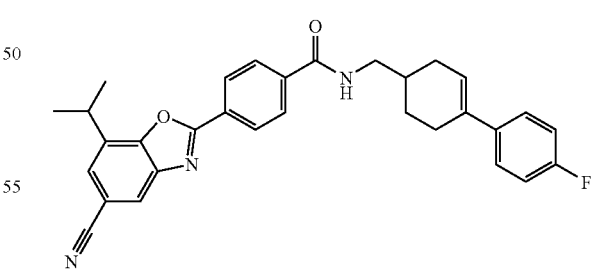

4-({[4-(5-Cyano-7-isopropyl-1,3-benzoxazol-2-yl)benzoyl]amino}methyl)cyclohex-1-en-1-yl trifluoromethanesulfonate

Step A. 4-(5-Cyano-7-isopropyl-1,3-benzoxazol-2-yl)-N-[(4-oxocyclohexyl)methyl]benzamide To a solution of tert-butyl [(4-oxocyclohexyl)methyl]carbamate (5.0 g, 22.00 mmol) in dichloromethane (100 ml) was added trifluoroacetic acid (10 ml). The mixture was stirred for 1 h at room temperature, and then concentrated and co-concentrated with toluene (5 ml). A suspension of 4-(5-cyano-7-isopropyl-1,3-benzoxazol-2-yl)benzoic acid (INTERMEDIATE 2, 6.13 g, 20 mmol), o-benzotriazol-1-yl-tetramethyluronium hexafluorophosphate (15.2 g, 40.1 mmol), 1-hydroxybenzotriazole (4.0 g, 29.6 mmol), and diisopropylethylamine (20 ml, 115 mmol) in dichloromethane (100 ml) was stirred for 5 min at room temperature, and then a solution of the deprotected amine in dichloromethane (100 ml) was added. The mixture was stirred overnight at 25° C. The mixture was filtered and then diluted with 300 ml of saturated sodium bicarbonate solution. The phases were separated and the aqueous phase was extracted with 2×100 ml of dichloromethane. The combined organics were washed with 100 ml of brine, dried (sodium sulfate), and concentrated. The residue was purified by flash chromatography on a Biotage Horizon, 65i column, eluting with 1 column volume of 100% dichloromethane followed by a gradient of 0 to 100% ethyl acetate in dichloromethane over 10 column volumes. The resulting product was repurified by flash chromatography on a Biotage Horizon, 65i column, eluting with 1 column volume of 100% hexanes followed by a gradient of 0 to 100% acetone in hexanes over 10 column volumes. The resulting product was crystallized from dichloromethane to provide the title compound (5.52 g, 13.29 mmol, 66.4% yield). Mass spectrum (ESI) 416.0 (M+1).

Step B. 4-({[4-(5-Cyano-7-isopropyl-1,3-benzoxazol-2-yl)benzoyl]amino}methyl)cyclohex-1-en-1-yl trifluoromethanesulfonate A solution (partially dissolved) of 4-(5-cyano-7-isopropyl-1,3-benzoxazol-2-yl)-N-[(4-oxocyclohexyl)methyl]benzamide (2.0 g, 4.81 mmol) in dichloromethane (75 ml) was cooled 0° C. 2,6-Lutidine (1.121 ml, 9.63 mmol) was added, and then trifluoromethanesulfonic anhydride (2.440 ml, 14.44 mmol) was added dropwise. The mixture was allowed to warm to room temperature while stirring overnight. The mixture was concentrated to an oil and purified by flash chromatography on a Biotage Horizon 65i column, eluting with 1 column volume of 100% dichloromethane followed by a gradient of 0 to 100% ethyl acetate in dichloromethane over 10 column volumes, to provide the title compound (2.03 g, 3.71 mmol, 77% yield). Mass spectrum (ESI) 548.0 (M+1). $^1$H NMR (500 MHz, CDCl$_3$): δ 8.34 (d, J=8.5 Hz, 2H); 7.95 (d, J=8.5 Hz, 2H), 7.94 (s, 1H); 7.52 (s, 1H), 6.32 (br s, 1H), 5.77 (br s, 1H), 3.42-3.54 (m, 3H), 2.34-2.51 (m, 3H), 1.86-2.08 (m, 3H), 1.52-1.64 (m, 1H), 1.46 (d, J=6.5 Hz, 6H).

Example 41

4-(5-Cyano-7-isopropyl-1,3-benzoxazol-2-yl)-N-{[4-(4-fluorophenyl)cyclohex-3-en-1-yl]methyl}benzamide To a mixture of 4-({[4-(5-cyano-7-isopropyl-1,3-benzoxazol-2-yl)benzoyl]amino}methyl)cyclohex-1-en-1-yl trifluoromethanesulfonate (50 mg, 0.091 mmol, INTERMEDIATE 5) and 4-fluorophenyl boronic acid (25 mg, 0.179 mmol)

in tetrahydrofuran (2 ml) and 1 M aqueous potassium carbonate (1 ml, 1.000 mmol) was added 1,1'-bis(di-t-butylphosphino)ferrocene palladium dichloride (1 mg, 5.64 µmol). The mixture was microwaved at 100° C. in a sealed tube for 10 min, cooled, and then resubmitted to the reaction conditions for 10 min, at which point LC/MS analysis showed no starting material. The organic phase of the reaction mixture was added directly to a 25 samplet and purified by flash chromatography on a Biotage Horizon, 25M column, eluting with 1 column volume of 100% dichloromethane followed by a gradient of 0 to 100% ethyl acetate in dichloromethane over 10 column volumes, to provide the title compound (37.5 mg, 0.076 mmol, 83% yield). Mass spectrum (ESI) 494.1 (M+1). $^1$H NMR (500 MHz, CDCl$_3$): δ 8.32 (d, J=8.5 Hz, 2H); 7.96 (d, J=8.0 Hz, 2H), 7.93 (d, J=1.5 Hz, 1H); 7.51 (s, 1H), 7.32 (ddd, J=2.0, 5.5, 8.5 Hz, 2H), 6.99 (t, J=9.0 Hz, 2H), 6.39 (br t, J=5.5 Hz, 1H), 6.03 (s, 1H), 3.42-3.58 (m, 3H), 2.34-2.56 (m, 3H), 1.96-2.08 (m, 3H), 1.46 (d, J=7.0 Hz, 6H), 1.44-1.62 (m, 2H).

Example 42

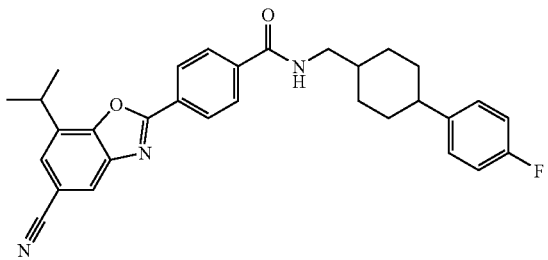 [SMILES: CC(C)c1cc(C#N)cc2nc(-c3ccc(C(=O)NCC4CCC(c5ccc(F)cc5)CC4)cc3)oc12]

cis and trans 4-(5-Cyano-7-isopropyl-1,3-benzoxazol-2-yl)-N-{[4-(4-fluorophenyl)cyclohexyl]methyl}benzamide To a solution of 4-(5-cyano-7-isopropyl-1,3-benzoxazol-2-yl)-N-{[4-(4-fluorophenyl)cyclohex-3-en-1-yl]methyl}benzamide (30 mg, 0.061 mmol, EXAMPLE 41) in methanol (1 ml) and tetrahydrofuran (1 ml) was added 10% palladium on carbon (10 mg, 0.094 mmol). The mixture was flushed with nitrogen, then flushed with hydrogen and stirred for 6 h under a hydrogen balloon, at which point LC/MS analysis showed no starting material. The mixture was added directly to a 1000-micron plate and then eluted with 1:1 ethyl acetate-hexanes to provide the desired products trans-4-(5-cyano-7-isopropyl-1,3-benzoxazol-2-yl)-N-{[4-(4-fluorophenyl)cyclohexyl]methyl}benzamide (11.9 mg, 0.024 mmol, 39.5% yield) and cis-4-(5-cyano-7-isopropyl-1,3-benzoxazol-2-yl)-N-{[4-(4-fluorophenyl)cyclohexyl]methyl}benzamide (14.0 mg, 0.028 mmol, 46.5% yield).

trans-4-(5-Cyano-7-isopropyl-1,3-benzoxazol-2-yl)-N-{[4-(4-fluorophenyl)cyclohexyl]methyl}benzamide: Mass spectrum (ESI) 496.0 (M+1). $^1$H NMR (500 MHz, CDCl$_3$): δ 8.33 (d, J=8.5 Hz, 2H); 7.96 (d, J=8.5 Hz, 2H), 7.93 (d, J=1.5 Hz, 1H); 7.51 (s, 1H), 7.15 (dd, J=5.5, 8.5 Hz, 2H), 6.97 (t, J=8.5 Hz, 2H), 6.35 (br t, J=5.5 Hz, 1H), 3.48 (septet, J=6.5 Hz, 1H), 3.42 (t, J=6.5 Hz, 2H), 2.50 (m, 1H), 1.96 (m, 4H), 1.66-1.80 (m, 2H), 1.46 (d, J=7 Hz, 6H), 1.40-1.52 (m, 2H), 1.23 (m, 3H).

cis-4-(5-Cyano-7-isopropyl-1,3-benzoxazol-2-yl)-N-{[4-(4-fluorophenyl)cyclohexyl]methyl}benzamide: Mass spectrum (ESI) 496.0 (M+1). $^1$H NMR (500 MHz, CDCl$_3$): δ 8.33 (d, J=8.5 Hz, 2H); 7.95 (d, J=8.0 Hz, 2H), 7.93 (d, J=1.5 Hz, 1H); 7.51 (s, 1H), 7.21 (dd, J=5.5, 9.0 Hz, 2H), 6.98 (t, J=9.0 Hz, 2H), 6.35 (br t, J=5.5 Hz, 1H), 3.61 (dd, J=6.0, 7.5 Hz, 2H), 3.48 (septet, J=6.5 Hz, 1H), 2.62 (m, 1H), 2.05 (m, 1H), 1.66-1.84 (m, 8H), 1.46 (d, J=7.0 Hz, 6H).

INTERMEDIATE 6

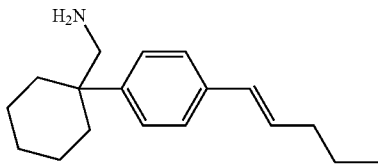

1-(1-{4-[(1E)-Pent-1-en-1-yl]phenyl}cyclohexyl)methanamine

To a mixture of 1-(4-chlorophenyl)-1-cyclohexanecarbonitrile (100 mg, 0.455 mmol) and 1-pentenylboronic acid (104 mg, 0.910 mmol) in tetrahydrofuran (2 ml) and 1 M potassium carbonate (1.5 ml, 1.500 mmol) was added 1,1'-bis(di t-butylphosphino)ferrocene palladium dichloride (10 mg, 0.056 mmol). The mixture was microwaved at 100° C. in a sealed tube for 20 min, at which point LC/MS analysis showed a new peak. The reaction mixture was diluted with 10 mL of EtOAc and 10 mL of saturated aqueous NaHCO$_3$. The phases were separated and the aqueous phase was extracted with 10 mL of EtOAc. The combined organics were washed with 10 mL of brine, dried (Na$_2$SO$_4$), and concentrated. The residue was purified by flash chromatography on a Biotage Horizon, 25M column, eluting with 1 CV of 100% hexanes followed by a gradient of 0 to 100% EtOAc in hexanes over 10 CV to provide the desired product 1-{4-[(1E)-pent-1-en-1-yl]phenyl}cyclohexanecarbonitrile (83 mg, 0.328 mmol, 72.0% yield). To a 0° C. solution of 1-{4-[(1E)-pent-1-en-1-yl]phenyl}cyclohexanecarbonitrile (75 mg, 0.296 mmol) in tetrahydrofuran (2 ml) was added 1.0 M lithium aluminum hydride in ether (1 ml, 1.000 mmol). The mixture was allowed to warm to room temperature and stirred at this temperature overnight, at which point LC/MS analysis showed complete disappearance of the starting nitrile. The mixture was recooled to 0° C. and quenched by dropwise addition of 30 µl of water, 30 µl of 15% NaOH, and 80 µl of water. The mixture was stirred for 30 min at room temperature, and then filtered, washing the solids liberally with ether. The filtrate was concentrated to provide the title compound (78 mg, 0.303 mmol, 102% yield). Mass spectrum (ESI) 258.0 (M+1).

INTERMEDIATE 7

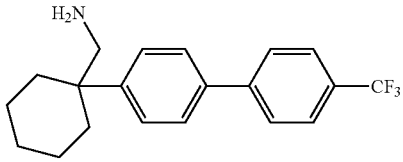

1-{1-[4'-(Trifluoromethyl)biphenyl-4-yl]cyclohexyl}methanamine

The title compound was synthesized following from 1-(4-chlorophenyl)-1-cyclohexanecarbonitrile and trifluoromethylphenyl boronic acid following the procedure described for INTERMEDIATE 6. Mass spectrum (ESI) 334.1 (M+1).

INTERMEDIATE 8

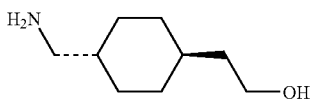

2-[trans-4-(Aminomethyl)cyclohexyl]ethanol

To a solution of trans-4-(2-ethoxy-2-oxoethyl)cyclohexanecarboxylic acid (750 mg, 3.50 mmol) in dichloromethane (5 ml) were added oxalyl chloride (5.25 ml, 10.50 mmol) and a drop (ca. 10 µl) of dimethylformamide. After stirring 1 h at room temperature, LC/MS analysis of an aliquot quenched into methanol showed the desired methyl ester. The mixture was concentrated and then dissolved in tetrahydrofuran (5 ml). Concentrated ammonium hydroxide (5 ml, 36.0 mmol) was added and the mixture was stirred overnight at room temperature, and then concentrated to a small volume, poured into 50 ml of 1 M sodium hydroxide, and diluted with 50 ml of ethyl acetate. The phases separated and the aqueous was extracted with 2×25 ml of ethyl acetate, and then the combined organics were washed with 25 ml of brine, dried (sodium sulfate), and concentrated to provide 985 mg (99%) of the desired amide. To a 0° C. solution of the residue in tetrahydrofuran (5 ml) was added lithium aluminum hydride (17.50 ml, 17.50 mmol) dropwise. The mixture was allowed to warm to room temperature and stirred at this temperature over the weekend, at which point LC/MS analysis showed complete disappearance of the starting amide. The mixture was recooled to 0° C. and quenched by dropwise addition of 600 µl of water, 600 µl of 15% sodium hydroxide, and 1 ml of water. The mixture was stirred for 1 h at room temperature, and then filtered, washing the solids liberally with ether. The filtrate was concentrated to provide the title compound (418 mg, 2.66 mmol, 76% yield). Mass spectrum (ESI) 157.9 (M+1).

Example 43

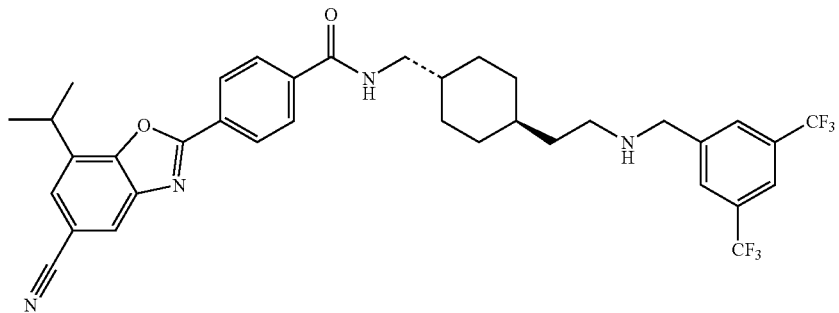

N-{[trans-4-(2-{[3,5-Bis(trifluoromethyl)benzyl]amino}ethyl)cyclohexyl]methyl}-4-(5-cyano-7-isopropyl-1,3-benzoxazol-2-yl)benzamide Step A. 4-(5-Cyano-7-isopropyl-1,3-benzoxazol-2-yl)-N-{[trans-4-(2-hydroxyethyl)cyclohexyl]methyl}benzamide The title compound was prepared from 4-(5-cyano-7-isopropyl-1,3-benzoxazol-2-yl)benzoic acid (INTERMEDIATE 2), and 2-[trans-4-(aminomethyl)cyclohexyl]ethanol (INTERMEDIATE 8) as described in EXAMPLE 1. Mass spectrum (ESI) 446.1 (M+1).

Step B. 4-(5-Cyano-7-isopropyl-1,3-benzoxazol-2-yl)-N-{[trans-4-(2-oxoethyl)cyclohexyl]methyl}benzamide To a solution of 4-(5-cyano-7-isopropyl-1,3-benzoxazol-2-yl)-N-{[trans-4-(2-hydroxyethyl)cyclohexyl]methyl}benzamide (50 mg, 0.112 mmol) in dichloromethane (2 ml) was added Dess-Martin periodinane (60 mg, 0.141 mmol). The mixture was stirred for 2 h at 25° C., at which point LC/MS analysis showed no starting material. The mixture was purified by flash chromatography on a Biotage Horizon, 25M column, eluting with 1 column volume of 100% dichloromethane followed by a gradient of 0 to 100% ethyl acetate in dichloromethane over 10 column volumes to provide the title compound (48 mg, 0.108 mmol, 96% yield). Mass spectrum (ESI) 444.0 (M+1).

Step C. N-{[trans-4-(2-{[3,5-Bis(trifluoromethyl)benzyl]amino}ethyl)cyclohexyl]methyl}-4-(5-cyano-7-isopropyl-1,3-benzoxazol-2-yl)benzamide To a solution of 4-(5-cyano-7-isopropyl-1,3-benzoxazol-2-yl)-N-{[trans-4-(2-oxoethyl)cyclohexyl]methyl}benzamide (25 mg, 0.056 mmol) in methanol (2 ml) were added 3,5-bis(trifluoromethyl)benzylamine (20 mg, 0.082 mmol) and sodium cyanoborohydride (10 mg, 0.159 mmol). The mixture was stirred overnight at room temperature, at which point LC/MS analysis showed a new peak at the desired molecular weight. The reaction mixture was then diluted with 10 ml of saturated sodium bicarbonate solution and 10 ml of ethyl acetate. The phases were separated and the aqueous phase was extracted with 2×10 ml of ethyl acetate. The combined organics were washed with 10 ml of brine, dried (sodium sulfate), and concentrated. The residue was purified by flash chromatography on a Biotage Horizon, 25S column, eluting with 1 column volume of 100% dichloromethane followed by a gradient of 0 to 100% ethyl acetate in dichloromethane over 10 column volumes to provide the title compound (11.9 mg, 0.018 mmol, 31.5% yield). Mass spectrum (ESI) 671.5 (M+1). $^1$H NMR (500 MHz, CDCl$_3$): δ 8.33 (d, J=8.5 Hz, 2H); 7.96 (d, J=8.5 Hz, 2H), 7.93 (d, J=1.5 Hz, 1H); 7.83 (s, 2H), 7.75 (s, 1H), 7.51 (s, 1H), 6.35 (br t, J=5.5 Hz, 1H), 5.30 (s, 2H), 3.85 (s, 2H), 3.48 (septet, J=6.5 Hz, 1H), 3.35 (t, J=6.5 Hz, 2H), 2.65 (t, J=6.5 Hz, 2H), 1.80 (m, 4H), 1.60 (m, 1H), 1.46 (d, J=7.0 Hz, 6H), 1.40-1.52 (m, 1H), 0.90-1.15 (m, 4H).

Example 44

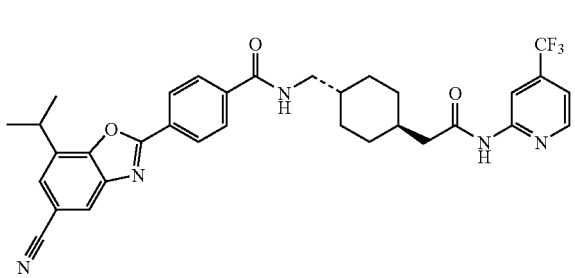

4-(5-Cyano-7-isopropyl-1,3-benzoxazol-2-yl)-N-{[trans-4-(2-oxo-2-{[4-(trifluoromethyl)pyridin-2-yl]amino}ethyl)cyclohexyl]methyl}benzamide

Step A. [trans-4-({[4-(5-Cyano-7-isopropyl-1,3-benzoxazol-2-yl)benzoyl]amino}methyl)cyclohexyl]acetic acid To a suspension (partially dissolved) of 4-(5-cyano-7-isopropyl-1,3-benzoxazol-2-yl)-N-{[trans-4-(2-oxoethyl)cyclohexyl]methyl}benzamide (50 mg, 0.113 mmol, EXAMPLE 43, Step B) in t-butanol (4 ml) was added 2-methyl-2-butene (0.060 ml, 0.570 mmol), and then a solution of sodium chlorite (25 mg, 0.276 mmol) and sodium dihydrogen phosphate (27 mg, 0.225 mmol) in water (1 ml). The mixture was stirred overnight at room temperature (the mixture remained a finely divided suspension), at which point LC/MS analysis showed no starting material. The mixture was diluted with 10 ml of water and 10 ml of ethyl acetate. The phases were separated and the aqueous phase was acidified to pH 4 and extracted with 2×10 ml of ethyl acetate. The combined organics were washed with 10 ml of brine, dried (sodium sulfate), and concentrated to provide the title compound (52 mg, 0.113 mmol, 100% yield). Mass spectrum (ESI) 459.8 (M+1).

Step B. 4-(5-Cyano-7-isopropyl-1,3-benzoxazol-2-yl)-N-{[trans-4-(2-oxo-2-{[4-(trifluoromethyl)pyridin-2-yl]amino}ethyl)cyclohexyl]methyl}benzamide The title compound was prepared from [trans-4-({[4-(5-cyano-7-isopropyl-1,3-benzoxazol-2-yl)benzoyl]amino}methyl)cyclohexyl]acetic acid and 2-amino-4-(trifluoromethyl)pyridine as described in EXAMPLE 1. Mass spectrum (ESI) 604.1 (M+1). $^1$H NMR (500 MHz, CD$_3$OD): δ 8.50 (d, J=5.0 Hz, 1H), 8.44 (s, 1H), 8.35 (d, J=8.0 Hz, 2H); 8.02 (d, J=8.5 Hz, 2H), 8.02 (d, J=1.5 Hz, 1H); 7.65 (s, 1H), 7.33 (d, J=5.0 Hz, 1H), 3.50 (septet, J=7.0 Hz, 1H), 3.26 (d, J=7.0 Hz, 2H), 2.35 (d, J=6.5 Hz, 2H), 185-1.70 (m, 5H), 1.65 (m, 1H), 1.47 (d, J=7.0 Hz, 6H), 1.08-1.18 (m, 4H).

Example 45

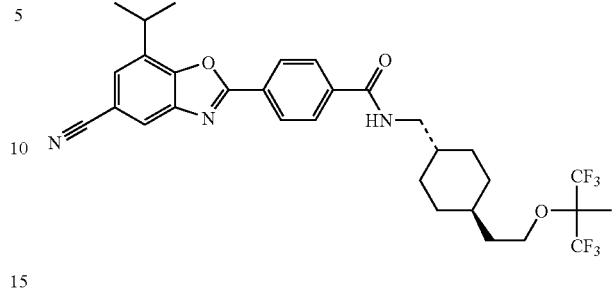

4-(5-Cyano-7-isopropyl-1,3-benzoxazol-2-yl)-N-[(trans-4-{2-[2,2,2-trifluoro-1-methyl-1-(trifluoromethyl)ethoxy]ethyl}cyclohexyl)methyl]benzamide To a solution of 4-(5-cyano-7-isopropyl-1,3-benzoxazol-2-yl)-N-{[trans-4-(2-hydroxyethyl)cyclohexyl]methyl}benzamide (50 mg, 0.112 mmol, EXAMPLE 43, Step A) and 1,1'-(azodicarbonyl)dipiperidine (57 mg, 0.226 mmol) in toluene (2 ml) was added tri-n-butylphosphine (0.06 ml, 0.241 mmol). After stirring for 10 min, hexafluoro-2-methylisopropanol (0.03 ml, 0.245 mmol) was added. Tetrahydrofuran (2 ml) was added to solubilize starting material, and the mixture was stirred overnight at room temperature. The mixture was concentrated and the residue was purified by flash chromatography on a Biotage Horizon, 25S column, eluting with 1 column volume of 100% dichloromethane followed by a gradient of 0 to 100% ethyl acetate in dichloromethane over 10 column volumes to provide the title compound (8.7 mg, 0.014 mmol, 12.72% yield). Mass spectrum (ESI) 610.2 (M+1). $^1$H NMR (500 MHz, CDCl$_3$): δ 8.33 (d, J=8.5 Hz, 2H); 7.94 (d, J=8.5 Hz, 2H), 7.94 (d, J=1.5 Hz, 1H); 7.51 (s, 1H), 6.27 (br s, 1H), 3.72 (t, J=6.5 Hz, 2H), 3.46 (septet, J=6.5 Hz, 1H), 3.36 (t, J=6.0 Hz, 2H), 1.83 (m, 4H), 1.50-1.65 (m, 5H), 1.46 (d, J=7.0 Hz, 6H), 1.40-1.50 (m, 2H), 0.85-1.22, (m, 6H).

INTERMEIDATE 9

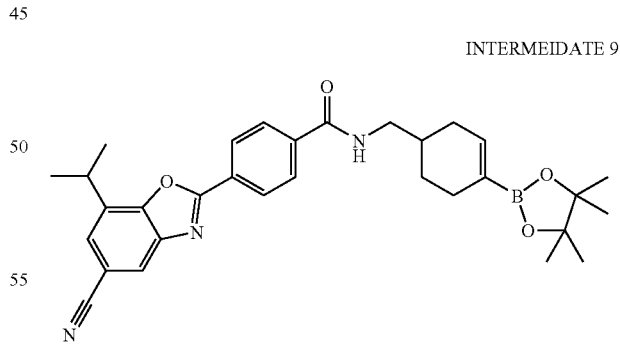

4-(5-Cyano-7-isopropyl-1,3-benzoxazol-2-yl)-N-{[4-(4,4,5,5-tetramethyl-1,3,2-dioxaborolan-2-yl)cyclohex-3-en-1-yl]methyl}benzamide To a mixture of 4-({[4-(5-cyano-7-isopropyl-1,3-benzoxazol-2-yl)benzoyl]amino}methyl)cyclohex-1-en-1-yl trifluoromethanesulfonate (425 mg, 0.776 mmol, INTERMEDI- ATE 5), bispinacolatodiboron (200 mg, 0.788 mmol), potassium acetate (230 mg, 2.344 mmol), 1,1'-bis(diphenylphosphino) ferrocene (22 mg, 0.040 mmol and dichloro [1,1'-bis (diphenylphosphino)ferrocene] palladium(II)-dichloromethane adduct (32 mg, 0.039 mmol) was added dioxane (4 ml). The mixture was microwaved at 140° C. in a sealed tube for 1 h, cooled, and then resubmitted to reaction conditions for 30 min, at which point no starting material remained. The reaction mixture was filtered and concentrated, and the residue was purified by flash chromatography on a Biotage Horizon, 40M column, eluting with 1 column volume of 100% dichloromethane followed by a gradient of 0 to 100% ethyl acetate in dichloromethane over 10 column volumes, to provide the title compound (145 mg, 0.276 mmol, 35.6% yield). Mass spectrum (ESI) 526.2 (M+1). $^1$H NMR (500 MHz, CDCl$_3$): δ 8.31 (d, J=8.5 Hz, 2H); 7.93 (d, J=8.5 Hz, 2H), 7.90 (d, J=1.5 Hz, 1H); 7.49 (s, 1H), 6.53 (br s, 1H), 6.44 (br t, J=5.5 Hz, 1H), 3.68 (s, 2H), 3.46 (septet, J=7.0 Hz, 1H), 3.42 (t, J=6.0 Hz, 2H), 2.28 (br d, J=16.5 Hz, 2H), 2.04-2.18 (m, 1H), 1.72-2.04 (m, 4H), 1.44 (d, J=7.0 Hz, 6H), 1.10-1.40 (m, 15H).

Example 46

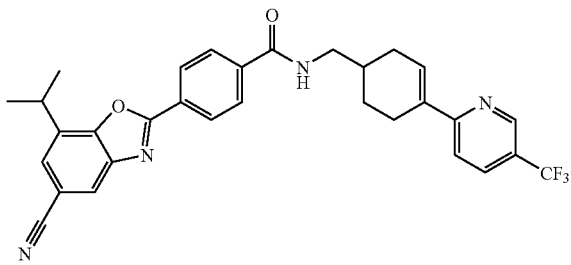 [SMILES: CC(C)c1cc(C#N)cc2nc(-c3ccc(C(=O)NCC4CC=C(c5ccc(C(F)(F)F)cn5)CC4)cc3)oc12]

4-(5-Cyano-7-isopropyl-1,3-benzoxazol-2-yl)-N-({4-[5-(trifluoromethyl)pyridin-2-yl]cyclohex-3-en-1-yl}methyl)benzamide To a mixture of 4-(5-cyano-7-isopropyl-1,3-benzoxazol-2-yl)-N-{[4-(4,4,5,5-tetramethyl-1,3,2-dioxaborolan-2-yl)cyclohex-3-en-1-yl]methyl}benzamide (70 mg, 0.133 mmol, INTERMEDIATE 9), 2-bromo-5-(trifluoromethyl)pyridine (45 mg, 0.199 mmol), and cesium carbonate (130 mg, 0.400 mmol) in tetrahydrofuran (6 ml) and water (0.6 ml) was added dichloro[1,1'-bis(diphenylphosphino)ferrocene]palladium (II)-dichloromethane adduct (7 mg, 8.57 mmol). The mixture was heated to reflux and stirred at this temperature overnight. The reaction mixture was cooled and added directly to a 25 samplet, and then purified by flash chromatography on a Biotage Horizon, 25S column, eluting with 1 column volume of 100% dichloromethane followed by a gradient of 0 to 100% ethyl acetate in dichloromethane over 10 column volumes, to provide the title compound (35 mg, 0.064 mmol, 48.2% yield). Mass spectrum (ESI) 545.1 (M+1). $^1$H NMR (500 MHz, CDCl$_3$): δ 8.80 (s, 1H), 8.34 (d, J=8.5 Hz, 2H); 7.97 (d, J=8.5 Hz, 2H), 7.94 (d, J=1.0 Hz, 1H); 7.85 (d, J=8.0 Hz, 1H), 7.52 (s, 1H), 7.48 (d, J=8.5 Hz, 1H), 6.83, (br s, 1H), 6.37 (br t, J=5.5 Hz, 1H), 3.54 (br t, J=4.5 Hz, 2H), 3.48 (septet, J=6.5 Hz, 1H), 2.75 (br d, J=16.5 Hz, 1H), 2.53 (br d, J=15.5 Hz, 2H), 2.04-2.16 (m, 3H), 1.50-1.68 (m, 3H), 1.46 (d, J=7.0 Hz, 6H), 1.25 (m, 2H).

Example 47

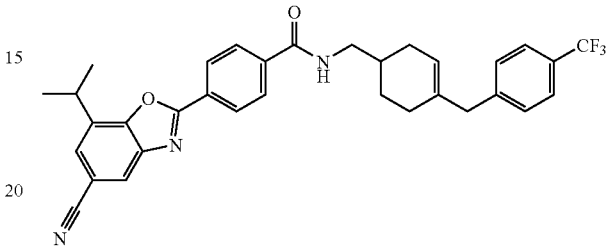

4-(5-Cyano-7-isopropyl-1,3-benzoxazol-2-yl)-N-({4-[4-(trifluoromethyl)benzyl]cyclohex-3-en-1-yl}methyl)benzamide To a mixture of 4-(5-cyano-7-isopropyl-1,3-benzoxazol-2-yl)-N-{[4-(4,4,5,5-tetramethyl-1,3,2-dioxaborolan-2-yl)cyclohex-3-en-1-yl]methyl}benzamide (70 mg, 0.133 mmol, INTERMEDIATE 9), 4-trifluoromethylbenzyl bromide (30 mg, 0.126 mmol), and 2M sodium carbonate (0.15 ml, 0.300 mmol) in toluene (2 ml), water (0.6 ml), and ethanol (0.25 ml) was added tetrakis(triphenylphosphine)palladium(0) (4 mg, 3.46 μmol). The mixture was microwaved at 100° C. in a sealed tube for 30 min, at which point LC/MS analysis showed a new peak at the product molecular weight. The organic phase of the reaction mixture was added directly to a 25 samplet and purified by flash chromatography on a Biotage Horizon, 25S column, eluting with 1 column volume of 100% dichloromethane followed by a gradient of 0 to 100% ethyl acetate in dichloromethane over 10 column volumes. This product was repurified by reverse-phase HPLC on a Kromasil C18 21×100 mm column, eluting at 15 ml/min with 90% water (0.1% TFA) to 95% acetonitrile (0.1% TFA) over 10 min, hold for 2 min, then back to 90% water over 0.5 min, hold for 0.5 min, to provide the title compound (9.4 mg, 0.017 mmol, 25.3% yield). Mass spectrum (ESI) 558.2 (M+1). $^1$H NMR (500 MHz, CDCl$_3$): δ 8.32 (d, J=8.5 Hz, 2H); 7.93 (d, J=8.5 Hz, 2H), 7.93 (d, J=1.5 Hz, 1H); 7.53 (d, J=8.0 Hz, 2H), 7.51 (s, 1H), 7.27 (d, J=8.5 Hz, 1H), 6.28 (br t, J=5.5 Hz, 1H), 5.48 (br s, 1H), 3.47 (septet, J=7.0 Hz, 1H), 3.44 (br t, J=6.0 Hz, 2H), 3.32 (s, 1H), 2.24 (m, 1H), 1.80-1.98 (m, 7H), 1.46 (d, J=7.0 Hz, 6H), 1.30-1.42 (m, 2H).

Following the procedures described in EXAMPLES 1, 41, 42, 46, and 47, the compounds listed in Table 4 were prepared. The symbol "X$_1$" on each substituent group shows the point of attachment of the substituent group to the structure at the top of the table.

TABLE 4

| EXAMPLE | R | MS (M + 1) |
|---|---|---|
| 48 | (cyclohexyl-phenyl) | 478.2 |
| 49 | (cyclohexyl-4'-trifluoromethylbiphenyl) | 622.2 |
| 50 | (cyclohexyl-4-(pent-1-enyl)phenyl) | 546.3 |
| 51 | (cyclohexyl-4-chlorophenyl) | 512.1 |
| 52 | (cyclohexyl-4-trifluoromethylphenyl) | 546.0 |
| 53 | (cyclohexyl-4-trifluoromethylphenyl) | 546.0 |

TABLE 4-continued

| EXAMPLE | R | MS (M + 1) |
|---|---|---|
| 54 | (cyclohexyl-3-trifluoromethylphenyl) | 546.1 |
| 55 | (cyclohexyl-3-trifluoromethylphenyl) | 546.1 |
| 56 | (cyclohexenyl-2-trifluoromethylphenyl) | 544.1 |
| 57 | (cyclohexenyl-4-trifluoromethylphenyl) | 544.1 |
| 58 | (cyclohexenyl-3-trifluoromethylphenyl) | 544.1 |
| 59 | (cyclohexyl-3-methylphenyl) | 492.2 |
| 60 | (cyclohexyl-3-methylphenyl) | 492.2 |

TABLE 4-continued

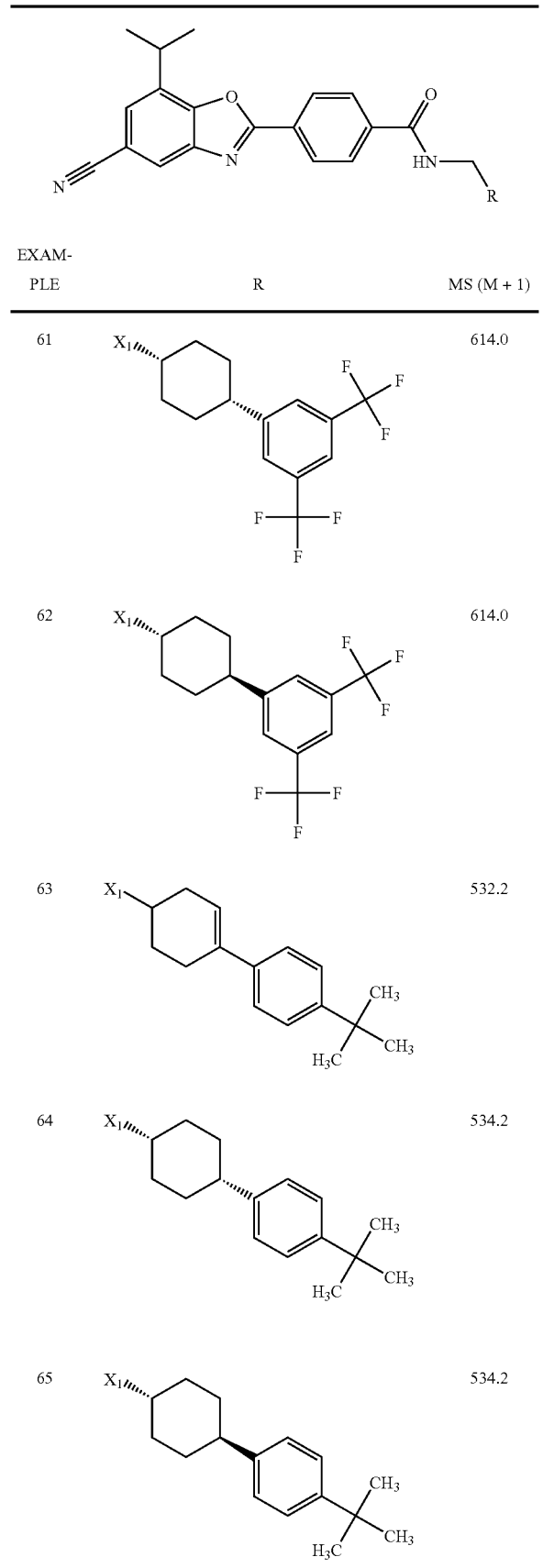

| EXAMPLE | R | MS (M + 1) |
|---|---|---|
| 61 | X₁—cyclohexyl—3,5-bis(trifluoromethyl)phenyl | 614.0 |
| 62 | X₁—cyclohexyl—3,5-bis(trifluoromethyl)phenyl | 614.0 |
| 63 | X₁—cyclohexenyl—4-tert-butylphenyl | 532.2 |
| 64 | X₁—cyclohexyl—4-tert-butylphenyl | 534.2 |
| 65 | X₁—cyclohexyl—4-tert-butylphenyl | 534.2 |

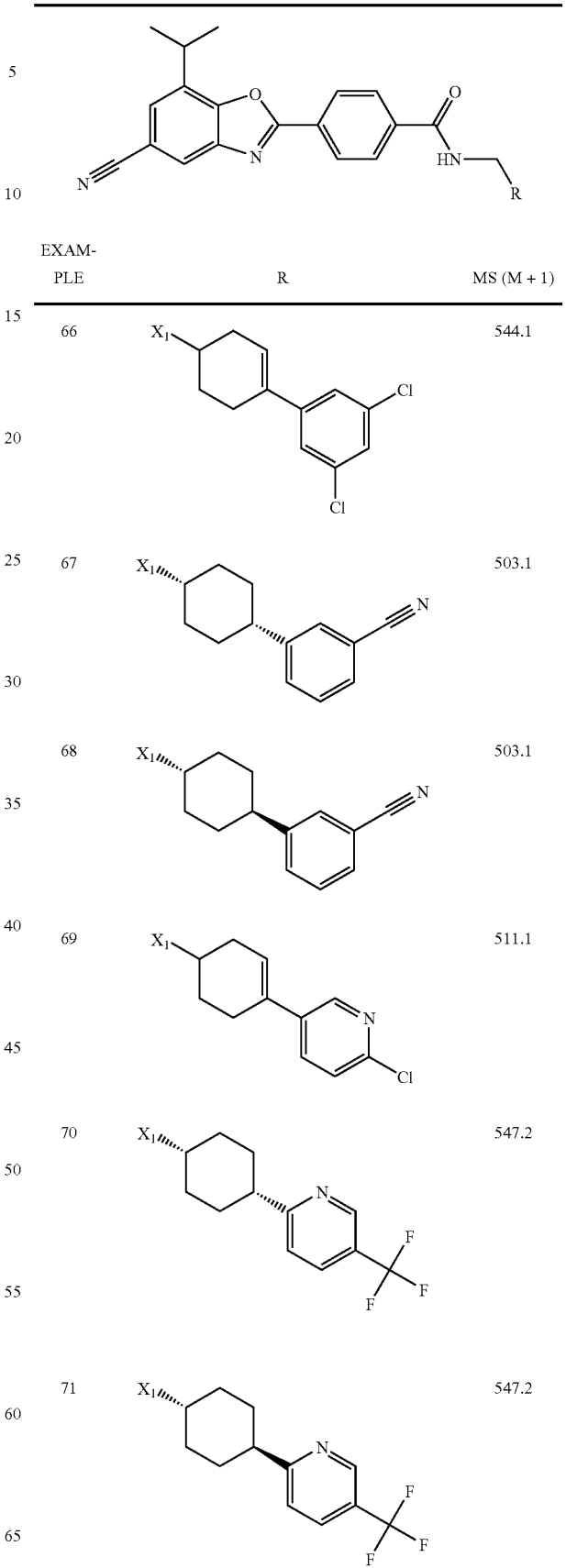

| EXAMPLE | R | MS (M + 1) |
|---|---|---|
| 66 | X₁—cyclohexenyl—3,5-dichlorophenyl | 544.1 |
| 67 | X₁—cyclohexyl—3-cyanophenyl | 503.1 |
| 68 | X₁—cyclohexyl—3-cyanophenyl | 503.1 |
| 69 | X₁—cyclohexenyl—6-chloropyridin-3-yl | 511.1 |
| 70 | X₁—cyclohexyl—5-(trifluoromethyl)pyridin-2-yl | 547.2 |
| 71 | X₁—cyclohexyl—5-(trifluoromethyl)pyridin-2-yl | 547.2 |

TABLE 4-continued

| EXAMPLE | R | MS (M + 1) |
|---|---|---|
| 72 | methyl 5-(cyclohex-1-en-1-yl)furan-2-carboxylate (X₁-cyclohexenyl-furan-CO₂CH₃) | 524.1 |
| 73 | methyl 5-(cyclohexyl)furan-2-carboxylate | 526.1 |
| 74 | methyl 5-(cyclohexyl)furan-2-carboxylate (other isomer) | 526.1 |
| 75 | 2-(cyclohex-1-en-1-yl)-1-methyl-1H-indole | 529.3 |
| 76 | tert-butyl 2-(cyclohex-1-en-1-yl)-5-methyl-1H-indole-1-carboxylate | 629.2 |
| 77 | 2-(cyclohex-1-en-1-yl)-1-(phenylsulfonyl)-1H-indole | 655.4 |
| 78 | 5-(cyclohex-1-en-1-yl)-4-methyl-2-(4-(trifluoromethyl)phenyl)thiazole | 641.3 |
| 79 | 2-(cyclohex-1-en-1-yl)-5-methylbenzo[b]thiophene | 546.2 |
| 80 | 6-(cyclohex-1-en-1-yl)-1H-indole | 515.3 |

TABLE 4-continued

[Structure: 7-isopropyl-5-cyano-1,3-benzoxazol-2-yl benzamide with HN-CH2-R substituent]

| EXAMPLE | R | MS (M + 1) |
|---|---|---|
| 81 | X₁—[trans-cyclohexyl]—[1-methylindol-2-yl] | 531.3 |
| 82 | X₁—[trans-cyclohexyl]—[benzofuran-2-yl] | 518.3 |
| 83 | X₁—[trans-cyclohexyl]—[benzofuran-2-yl] | 518.3 |
| 84 | X₁—[cyclohexenyl]—[cyclopentenyl] | 466.3 |
| 85 | X₁—[cyclohexenyl]—[4-methylcyclohexenyl] | 494.2 |

Example 86

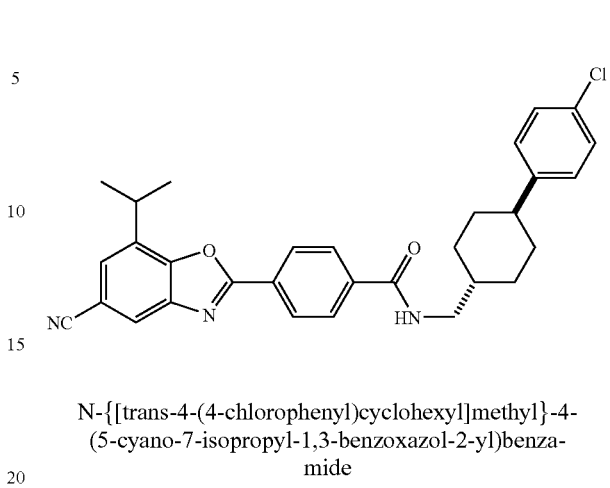

N-{[trans-4-(4-chlorophenyl)cyclohexyl]methyl}-4-(5-cyano-7-isopropyl-1,3-benzoxazol-2-yl)benzamide The title compound was prepared using the procedure described in EXAMPLE 1. Mass spectrum (ESI) 512.7 (M+2). $^1$H NMR (500 MHz, CDCl$_3$): δ 8.34 (d, J=8.2 Hz, 2H), 7.96 (d, J=8.5 Hz, 2H), 7.94 (s, 1H), 7.52 (s, 1H), 7.25 (d, J=8.2 Hz, 2H), 7.12 (d, J=8.3 Hz, 2H), 6.28 (t, J=5.5 Hz, 1H), 3.48 (sept, J=6.9 Hz, 1H), 3.42 (t, J=6.5 Hz, 2H), 2.50 (tt, J=11.9, 4.1 Hz, 1H), 1.97, (m, 4H), 1.73, (m, 1H), 1.50 (m, 2H) 1.46 (d, J=6.9 Hz, 6H), 1.22 (ddd, J=12.1, 12.0, 2.0 Hz, 2H).

Example 87

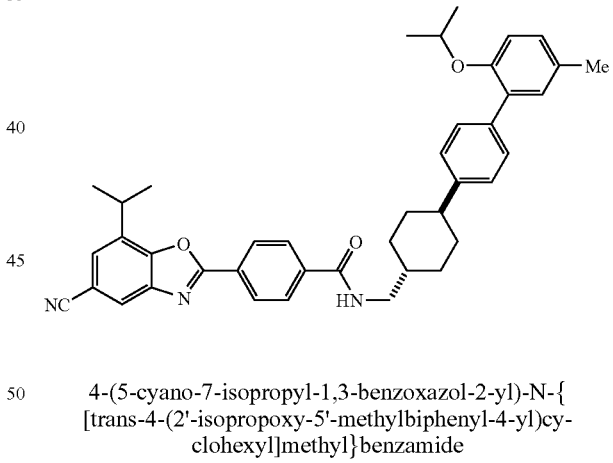

4-(5-cyano-7-isopropyl-1,3-benzoxazol-2-yl)-N-{[trans-4-(2'-isopropoxy-5'-methylbiphenyl-4-yl)cyclohexyl]methyl}benzamide A mixture of the N-{[trans-4-(4-chlorophenyl)cyclohexyl]methyl}-4-(5-cyano-7-isopropyl-1,3-benzoxazol-2-yl)benzamide (28 mg), 2-isopropyl-5-methylboronic acid (39 mg), potassium carbonate (28 mg), and palladium di-tert-butylphosphinoferrocene (5 mg) was placed in a 5-ml microwave vial. To this was added 1 ml of tetrahydrofuran and 1 ml of water. The vial was then microwaved at 150° C. for ca. 30 min. The reaction mixture was purified by flash chromatography on a Biotage Horizon, 40M column, eluting with 1 column volume of 100% hexanes, followed by a linear gradient of ethyl acetate in hexanes from 0 to 100% over 10 column volumes, followed by 4 column volumes of 100% ethyl acetate to provide the title compound (25 mg, 78%). Mass spectrum (ESI) 626.4 (M$^+$-1). $^1$H NMR (500 MHz, CDCl$_3$): δ 8.34 (d, J=8.2 Hz, 2H), 7.96 (d, J=8.5 Hz, 2H), 7.94 (s, 1H), 7.52 (s, 1H), 7.49 (d, J=8.0 Hz, 2H), 7.22 (d, J=8.3 Hz, 2H), 7.14 (s, 1H), 7.05 (d, J=7.6 Hz, 1H), 6.88 (d, J=8.3 Hz, 1H), 6.29 (t, J=5.0 Hz, 1H), 4.34 (sept, J=6.2 Hz, 1H), 3.48 (sept, J=6.9 Hz, 1H), 3.43 (t, J=6.2 Hz, 2H), 2.50 (tt, J=12.1, 4.0 Hz, 1H), 2.32 (s, 3H), 2.02, (m, 4H), 1.75, (m, 1H), 1.54 (m, 21-1) 1.46 (d, J=6.8 Hz, 6H), 1.23 (m, 2H), 1.22 (d, J=5.9 Hz, 6H).

Example 88

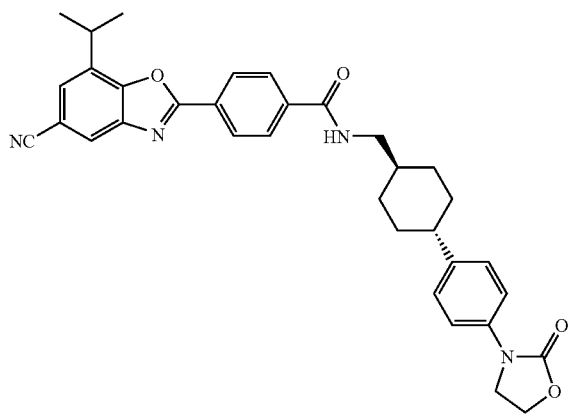

4-(5-cyano-7-isopropyl-1,3-benzoxazol-2-yl)-N-({trans-4-[4-(2-oxo-1,3-oxazolidin-3-yl)phenyl] cyclohexyl}methyl)benzamide Preparation of catalyst stock solution: To a dry microwave vial was added palladium acetate (67.3 mg, 0.1 mmol), 2-(di-tert-butylphosphino)biphenyl (60 mg, 0.2 mmol). The vial was crimped shut and then evacuated and back-filled with nitrogen three times. To the vial was added toluene or dimethylacetamide (10 ml). The mixture was allowed to mix for 30 min.

Method: A microwave vial (0.5-2 mL) was charged with N-{[trans-4-(4-chlorophenyl)cyclohexyl]methyl}-4-(5-cyano-7-isopropyl-1,3-benzoxazol-2-yl)benzamide (50 mg, 0.1 mmol, EXAMPLE 86), cesium carbonate (13.4 mg, 0.14 mmol), 2-oxazolidinone (10.4 mg, 0.12 mmol) and a stir bar. The vial was crimped shut and then evacuated and back-filled with nitrogen three times. To the vial was added 1 ml of the catalyst stock solution. The reaction mixture was microwaved at 150° C. for 30 min. The crude reaction mixture was applied to a pad of silica and washed with ethyl acetate (3×5 ml). The filtrate was concentrated in vacuo to provide a tan solid, which was purified by preparative HPLC, eluting with acetonitrile-water-0.1% TFA, to provide the title compound as a pale yellow solid (5.2 mg). Mass spectrum (ESI) 563.26 (M+1). $^1$H NMR (500 MHz, CDCl$_3$): δ8.31 (d, J=8.5 Hz, 2H), 7.94 (d, J=8.4 Hz, 2H), 7.92 (s, 1H), 7.49 (s, 1H), 7.43 (d, J=8.7 Hz, 2H), 7.19 (d, J=8.7 Hz, 2H), 6.34 (t, J=5.7 Hz, 1H), 4.45 (t, J=8 Hz, 2H), 4.02 (t, J=8.2 Hz, 2H), 3.47 (m, 1H), 3.40 (t, J=6.4 Hz, 2H), 2.49 (m, 1H), 1.95 (t, J=13.6 Hz, 4H), 1.7 (m, 1H), 1.583 (s br, 1H), 1.44 (d, J=6.9 Hz, 6H), 1.2 (m, 4H).

Example 89

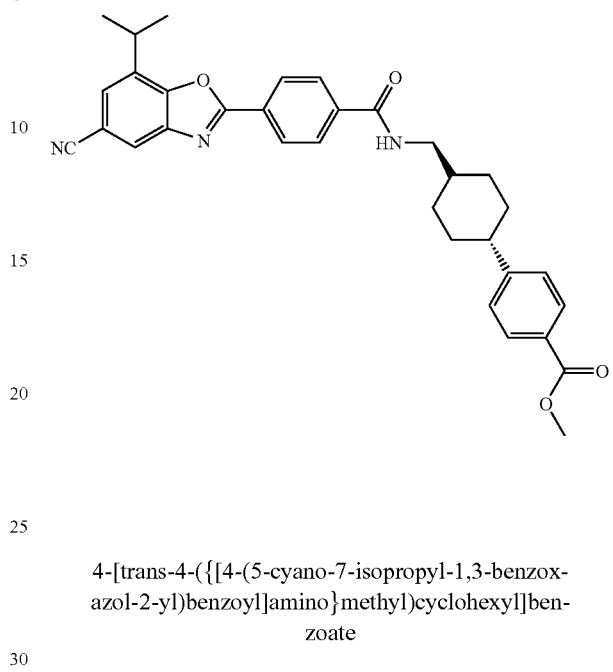

4-[trans-4-({[4-(5-cyano-7-isopropyl-1,3-benzoxazol-2-yl)benzoyl]amino}methyl)cyclohexyl]benzoate A 5-ml microwave vial was charged with 4-(4-chlorocyclohexyl)benzamide (118 mg, 0.5 mmol), nickel bromide (218 mg, 1.0 mmol), a stir bar, and dimethylformamide (600 μl). The mixture was heated to 170° C. for 5 min in a microwave reactor. The resulting mixture was dissolved in water (2 ml) and applied to a pad of silica. The silica pad was washed with ethyl acetate (2×10 ml), and the filtrate was concentrated to provide a white solid (118 mg) which was taken to the next step without further purification. Mass spectrum (ESI) 238.05 (M+1) and 283.94 (M+1) corresponded to a ca. 1:1 mixture of 4-(4-chlorocyclohexyl)benzamide and 4-(4-bromocyclohexyl)benzamide. This mixture was added to a round bottom flask, dissolved in THF (10 ml), and flushed with nitrogen for 5 min. A 2M solution of borane-THF (500 μl, 1 mmol) was added and the mixture was heated to reflux and stirred at this temperature for 6 h. The mixture was cooled and poured into a saturated aqueous solution of potassium carbonate (15 ml) and the product was extracted with ethyl acetate (3×10 ml). The organic layer was dried over sodium sulfate, filtered, and concentrated in vacuo to provide a mixture of 1-[4-(4-chlorocyclohexyl)phenyl]methanamine and 1-[4-(4-bromocyclohexyl)phenyl]methanamine (100 mg), which was used without further purification. This mixture was coupled with 4-(5-cyano-7-isopropyl-1,3-benzoxazol-2-yl)benzoic acid (INTERMEDIATE 2) following the procedure described in EXAMPLE 1, to provide a mixture of N-[4-(4-chlorocyclohexyl)benzyl]-4-(5-cyano-7-isopropyl-1,3-benzoxazol-2-yl) benzamide and N-[4-(4-bromocyclohexyl)benzyl]-4-(5-cyano-7-isopropyl-1,3-benzoxazol-2-yl)benzamide (100 mg). Mass spectrum (ESI) 512.08 (M+1) and 556.09 (M+1). A high pressure glass vessel was charged with this mixture, 1,3-bis(diphenylphosphino)propane (17 mg, 0.0414 mmol), palladium(II) acetate (24.2 mg, 0.036 mmol), triethylamine (185 μl, 1.33 mmol) and a solution of 5 ml of methanol and 5 ml of dimethylformamide. The carbonylation was carried out under 60 psi of carbon monoxide at 70° C. for 24 h. The crude reaction mixture was filtered through a pad of silica, and the silica pad was washed with ethyl acetate (3×10 ml). The organics were pooled and concentrated, and the title compound was isolated using reverse-phase chromatography, eluting with a gradient of 40% to 100% acetonitrile (0.1% TFA) in water (0.1% TFA) on a Waters Xterrra (30×100 mm) column to provide the title compound (1.5 mg). Mass spectrum (ESI) 536.24 (M+1). $^1$H NMR (600 MHz, CDCl$_3$): δ 8.32 (d, J=8. Hz, 2H), 7.94 (d, J=8.35 Hz, 4H), 7.92 (d, J=1.4. Hz, 1H), 7.5 (d, J=1.1 Hz, 1H), 7.25 (s, 2H), 6.33 (m, 1H), 3.89 (s, 3H), 3.46 (m, 1H), 3.41 (m, 2H), 2.56 (m, 1H), 1.97 (m, 4H), 1.72 (m, 1H), 1.51 (m, 1H), 1.44 (d, J=7, 6H), 1.23 (m, 4H).

Following the procedures described in EXAMPLES 86 and 88, the compounds listed in Table 5 were prepared:

TABLE 5

| EXAMPLE | R | MS (M + 1) |
|---|---|---|
| 90 | isopropenyl | 518.3 |
| 91 | phenyl | 554.2 |
| 92 | 3-pyridyl | 555.3 |
| 93 | 2-furyl | 544.3 |

TABLE 5-continued

| EXAMPLE | R | MS (M + 1) |
|---|---|---|
| 94 | isobutyl | 534.3 |
| 95 | 1-(4-fluorophenyl)vinyl | 598.3 |
| 96 | cyclopropylmethyl | 518.2 |
| 97 | morpholinomethyl | 563.3 |
| 98 | 2-oxoazetidinyl | 547.3 |
| 99 | pyrrolidinylmethyl | 547.3 |

Following the procedure described in EXAMPLE 1, the compounds listed in Table 6 were prepared. The symbol "X$_1$" on each substituent group shows the point of attachment of the substituent group to the structure at the top of the table.

TABLE 6
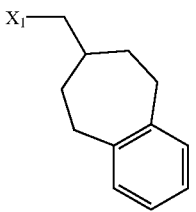
| EXAMPLE | R | MS (M + 1) |
|---|---|---|
| 100 | 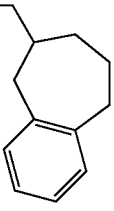 | 464.2 |
| 101 | 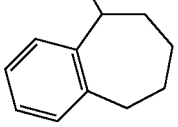 | 464.2 |
| 102 | 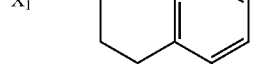 | 44.2 |
| 103 | 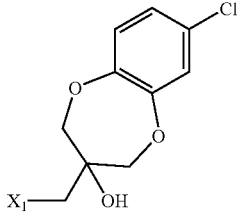 | 450.2 |
| 104 | 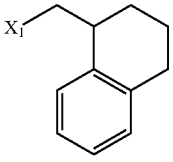 | 518.1 |
| 105 | 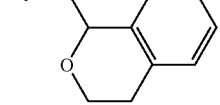 | 450.2 |
| 106 |  | 452.2 |

TABLE 6-continued
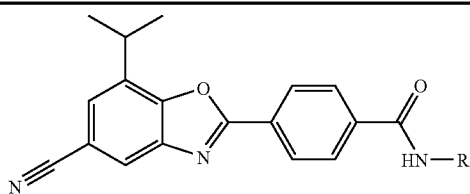
| EXAMPLE | R | MS (M + 1) |
|---|---|---|
| 107 | | 454.1 |
| 108 | | 468.2 |
| 109 | | 464.2 |
| 110 | ![](X₁-CH₂-1-(4-methylpiperazin-1-yl)cyclohexyl) | 500.3 |
| 111 | ![](X₁-CH₂-1-piperidinylcyclopentyl) | 417.3 |
| 112 | | 430.2 |
| 113 | (CH₂CH₂CH₂CH₃)) | 418.3 |
| 114 | ₁₁-CH₃) | 474.1 |

INTERMEDIATE 10

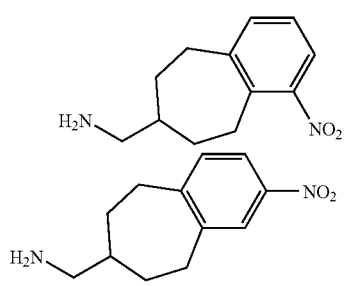

1-(1-Nitro-6,7,8,9-tetrahydro-5H-benzo[7]annulen-7-yl)methanamine and 1-(2-nitro-6,7,8,9-tetrahydro-5H-benzo[7]annulen-7-yl)methanamine

Step A. Benzyl(6,7,8,9-tetrahydro-5H-benzo[7]annulen-7-ylmethyl)carbamate

To a solution of 1-(6,7,8,9-tetrahydro-5H-benzo[7]annulen-7-yl)methanamine (100 mg, 0.472 mmol) in tetrahydrofuran (5 ml) was added benzyl chloridocarbonate (0.074 ml, 0.520 mmol) and diisopropylethylamine (0.181 ml, 1.039 mmol). The mixture was stirred overnight at 25° C., and then concentrated. The residue was purified by flash chromatography on a Biotage Horizon, 25S column, eluting with 1 column volume of 100% hexanes followed by a gradient of 0 to 100% EtOAc in hexanes over 10 column volumes to provide the title compound (133 mg, 0.430 mmol, 91% yield). Mass spectrum (ESI) 310.1 (M+1).

Step B. Benzyl [(1-nitro-6,7,8,9-tetrahydro-5H-benzo[7]annulen-7-yl)methyl]carbamate and benzyl [(2-nitro-6,7,8,9-tetrahydro-5H-benzo[7]annulen-7-yl)methyl]carbamate To a 0° C. solution of benzyl (6,7,8,9-tetrahydro-5H-benzo[7]annulen-7-ylmethyl)carbamate (100 mg, 0.323 mmol) in nitromethane (1 ml) was added a solution of nitric acid (50 µl, 0.783 mmol) in sulfuric acid (100 µl, 1.876 mmol). The mixture was stirred for 30 min at 0° C., at which point LC/MS analysis showed disappearance of starting material and appearance of a new product. The mixture was added dropwise to a rapidly stirring mixture of 10 ml of ice-water and 10 ml of diethyl ether. The phases were separated and the aqueous phase was extracted 2×10 ml of diethyl ether. The combined organics were washed with 10 ml each of water and brine, dried (sodium sulfate), and concentrated. The residue was purified by flash chromatography on a Biotage Horizon, 25S column, eluting with 1 column volume of 5% ethyl acetate in hexanes followed by a gradient of 5 to 100% ethyl acetate in hexanes over 10 column volumes to provide a ca. 1:1 mixture of the title compounds (90 mg total, 0.254 mmol, 79% yield). Mass spectrum of the mixture (ESI) 355.1 (M+1).

Step C. 1-(1-Nitro-6,7,8,9-tetrahydro-5H-benzo[7]annulen-7-yl)methanamine and 1-(2-nitro-6,7,8,9-tetrahydro-5H-benzo[7]annulen-7-yl)methanamine To a solution of a mixture of benzyl [(1-nitro-6,7,8,9-tetrahydro-5H-benzo[7]annulen-7-yl)methyl]carbamate and benzyl [(2-nitro-6,7,8,9-tetrahydro-5H-benzo[7]annulen-7-yl)methyl]carbamate (90 mg, 0.254 mmol) in methanol (2 ml) was added 40% (w/v) aqueous potassium hydroxide (400 mg, 2.85 mmol). The mixture was warmed to 75° C. to aid dissolution, and stirred at this temperature for 30 min, at which point LC/MS analysis showed disappearance of starting material and appearance of a new product. The mixture was cooled and diluted with 10 mL of water and 20 mL of EtOAc. The phases were separated and the aqueous phase was extracted with 2×10 mL of EtOAc. The combined organics were washed with 10 mL of brine, dried (Na$_2$SO$_4$), and concentrated to provide the title compound (49 mg, 0.222 mmol, 88% yield). Mass spectrum of the mixture (ESI) 221.1 (M+1).

Example 115

Ex 115(a)

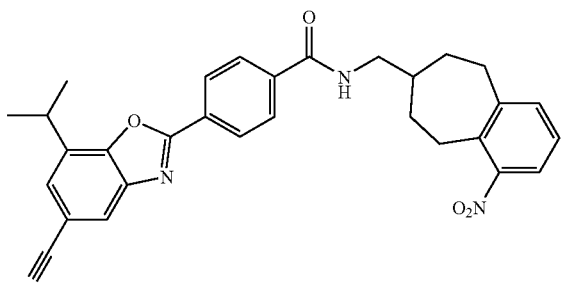

Ex115(b)

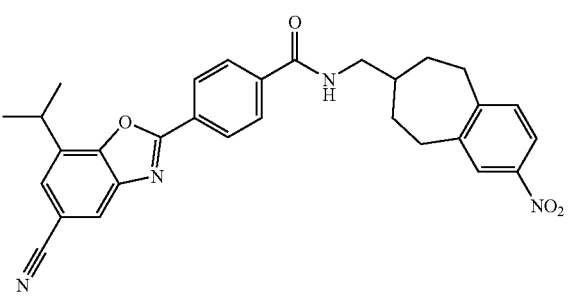

4-(5-Cyano-7-isopropyl-1,3-benzoxazol-2-yl)-N-[(1-nitro-6,7,8,9-tetrahydro-5H-benzo[7]annulen-7-yl)methyl]benzamide and 4-(5-cyano-7-isopropyl-1,3-benzoxazol-2-yl)-N-[(2-nitro-6,7,8,9-tetrahydro-5H-benzo[7]annulen-7-yl)methyl]benzamide The title compounds were prepared, as a mixture, from 4-(5-cyano-7-isopropyl-1,3-benzoxazol-2-yl)benzoic acid (INTERMEDIATE 2), and the mixture of 1-(1-nitro-6,7,8,9-tetrahydro-5H-benzo[7]annulen-7-yl)methanamine and 1-(2-nitro-6,7,8,9-tetrahydro-5H-benzo[7]annulen-7-yl)methanamine (INTERMEDIATE 10) as described in EXAMPLE 1. Spectral data is provided for the mixture of compounds. Mass spectrum (ESI) 509.1 (M+1). $^1$H NMR (500 MHz, CDCl$_3$):

INTERMEDIATES 11 and 12

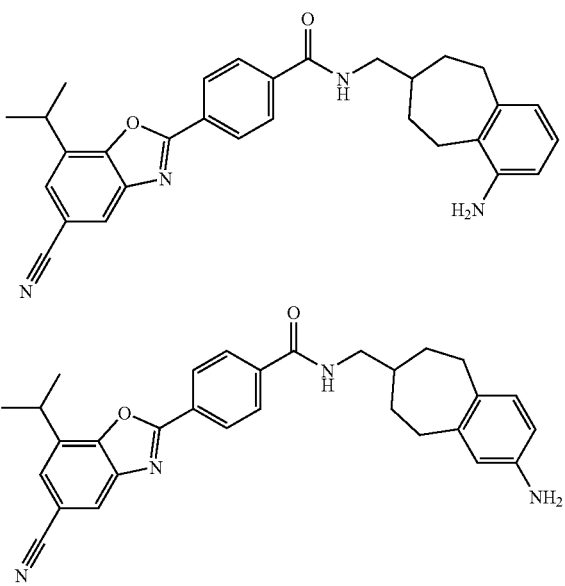

N-[(1-Amino-6,7,8,9-tetrahydro-5H-benzo[7]annulen-7-yl)methyl]-4-(5-cyano-7-isopropyl-1,3-benzoxazol-2-yl)benzamide and 1-(2-amino-6,7,8,9-tetrahydro-5H-benzo[7]annulen-7-yl)methanamine Step A. 7-(Aminomethyl)-6,7,8,9-tetrahydro-5H-benzo[7]annulen-1-amine and 7-(aminomethyl)-6,7,8,9-tetrahydro-5H-benzo[7]annulen-2-amine To a solution of a mixture of benzyl [(1-nitro-6,7,8,9-tetrahydro-5H-benzo[7]annulen-7-yl)methyl]carbamate and benzyl [(2-nitro-6,7,8,9-tetrahydro-5H-benzo[7]annulen-7-yl)methyl]carbamate (900 mg, 2.54 mmol, EXAMPLE 115, Step B) (18 mg, 0.030 mmol) in methanol (10 ml) was added palladium on carbon (90 mg, 0.846 mmol). The mixture was flushed with nitrogen, then flushed with hydrogen and stirred overnight under a hydrogen balloon. The mixture was filtered through a plug of Celite, washing liberally with methanol, and then concentrated and resubmitted to reaction conditions overnight. Another aliquot of palladium on carbon (90 mg, 0.846 mmol) was added and stirring under a hydrogen balloon was continued over the weekend. The mixture was filtered through a plug of Celite, washing liberally with methanol, and then concentrated to provide the title compounds as a mixture (501 mg, 2.63 mmol, 104% yield). Mass spectrum of the mixture (ESI) 191.0 (M+1).

Step B. N-[(1-Amino-6,7,8,9-tetrahydro-5H-benzo[7]annulen-7-yl)methyl]-4-(5-cyano-7-isopropyl-1,3-benzoxazol-2-yl)benzamide and 1-(2-amino-6,7,8,9-tetrahydro-5H-benzo[7]annulen-7-yl)methanamine To a suspension of a mixture of 7-(aminomethyl)-6,7,8,9-tetrahydro-5H-benzo[7]annulen-1-amine and 7-(aminomethyl)-6,7,8,9-tetrahydro-5H-benzo[7]annulen-2-amine (300 mg, 1.577 mmol) in dichloromethane (5 ml) were added o-benzotriazol-1-yl-tetramethyluronium hexafluorophosphate (1315 mg, 3.47 mmol), 1-hydroxybenzotriazole (320 mg, 2.365 mmol), diisopropylethylamine (0.67 ml, 3.84 mmol), and 4-(5-cyano-7-isopropyl-1,3-benzoxazol-2-yl)benzoic acid (435 mg, 1.419 mmol, INTERMEDIATE 2), and the mixture was stirred overnight at 25° C. The residue was purified by flash chromatography on a Biotage Horizon, 40M column, eluting with 1 column volume of 100% dichloromethane followed by a gradient of 0 to 100% ethyl acetate in dichloromethane over 10 column volumes. The resulting mixture was repurified under the same conditions to provide the two diastereomers N-[(1-amino-6,7,8,9-tetrahydro-5H-benzo[7]annulen-7-yl)methyl]-4-(5-cyano-7-isopropyl-1,3-benzoxazol-2-yl)benzamide (90 mg, 0.188 mmol, 11.93% yield) and 1-(2-amino-6,7,8,9-tetrahydro-5H-benzo[7]annulen-7-yl)methanamine (56 mg, 0.117 mmol, 7.42% yield). Mass spectrum for N-[(1-amino-6,7,8,9-tetrahydro-5H-benzo[7]annulen-7-yl)methanamine (ESI) 479.2 (M+1). Mass spectrum for 1-(2-amino-6,7,8,9-tetrahydro-5H-benzo[7]annulen-7-yl)methanamine (ESI) 479.0 (M+1). $^1$H NMR data for the mixture (500 MHz, CDCl$_3$): δ 8.32 (d, J=8.5 Hz, 2H), 7.90-8.96 (m, 4H), 7.51 (s, 1H), 7.49 (d, J=11 Hz, 1H), 7.49 (d, J=8.0 Hz, 2H), 7.32 (d, J=7.5 Hz, 2H), 7.25 (d, J=8.5 Hz, 1H), 7.20 (t, J=7.5 Hz, 1H), 6.42 (br s, 1H), 3.30-3.52 (m, 4H), 3.14 (dd, J=8.0, 14.0 Hz, 1H), 2.86-3.02 (m, 4H), 2.67 (dd, J=11.5, 14.5 Hz, 1H), 2.06-2.20 (m, 4H), 1.45 (d, J=7.5 Hz, 6H), 1.40-1.50 (m, 2H), 1.14-1.36 (m, 5H).

Example 116

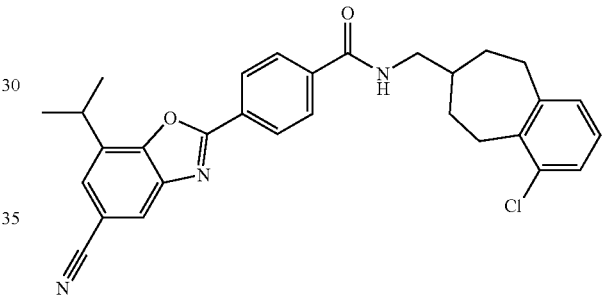

N-[(1-Chloro-6,7,8,9-tetrahydro-5H-benzo[7]annulen-7-yl)methyl]-4-(5-cyano-7-isopropyl-1,3-benzoxazol-2-yl)benzamide A suspension of N-[(1-amino-6,7,8,9-tetrahydro-5H-benzo[7]annulen-7-yl)methanamine (90 mg, 0.188 mmol) in water (2 ml) and concentrated hydrochloric acid (2 ml, 24.35 mmol) was cooled to 0° C. A solution of sodium nitrite (20 mg, 0.290 mmol) in 0.5 mL of water was added dropwise. This mixture was stirred for 30 min, and then a solution copper(I) chloride (24 mg, 0.242 mmol) in concentrated hydrochloric acid (2 ml, 24.35 mmol) was added dropwise. The resulting mixture was stirred overnight at room temperature, briefly (ca. 10 min) warmed to 75° C., and then cooled and diluted with 10 ml of water and 10 ml of ethyl acetate. The phases were separated and the organic phase was washed with 10 ml of water. The combined organics were dried (sodium sulfate) and concentrated. The residue was purified by flash chromatography on a Biotage Horizon, 25M column, eluting with 1 column volume of 100% dichloromethane followed by a gradient of 0 to 100% ethyl acetate in dichloromethane over 10 column volumes to provide the title compound (21 mg, 0.042 mmol, 22.42% yield). Mass spectrum (ESI) 498.1 (M+1). $^1$H NMR (500 MHz, CDCl$_3$): δ 8.32 (d, J=8.5 Hz, 2H), 7.95 (d, J=8.5 Hz, 2H), 7.93 (d, J=1.5 Hz, 1H), 7.51 (s, 1H), 7.21 (dd, J=3.0, 6.0 Hz, 1H), 7.01 (d, J=3.0 Hz, 1H), 6.35 (br t, J=6.0 Hz, 1H), 3.30-3.54 (m, 4H), 2.76-3.06 (m, 2H), 2.65 (dd, J=11.5, 14.5 Hz, 1H), 2.02-2.18 (m, 3H), 1.46 (d, J=7.0 Hz, 6H), 1.10-1.30 (m, 2H).

Example 117

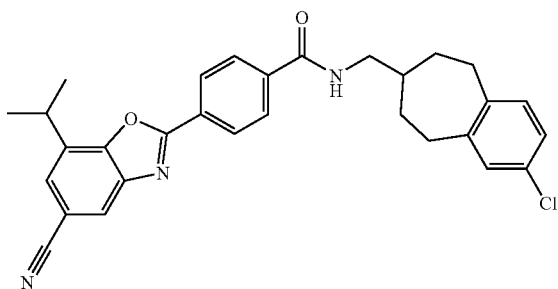 [SMILES: CC(C)c1cc(C#N)cc2nc(-c3ccc(C(=O)NCC4CCc5ccc(Cl)cc5CC4)cc3)oc12]

N-[(2-Chloro-6,7,8,9-tetrahydro-5H-benzo[7]annulen-7-yl)methyl]-4-(5-cyano-7-isopropyl-1,3-benzoxazol-2-yl)benzamide A suspension of 1-(2-amino-6,7,8,9-tetrahydro-5H-benzo[7]annulen-7-yl)methanamine (50 mg, 0.104 mmol) in water (1 ml) and concentrated hydrochloric acid (1 ml, 12.18 mmol) was cooled in an ice bath. A solution of sodium nitrite (10 mg, 0.145 mmol) in 0.5 mL of water was added dropwise. This mixture was stirred for 30 min, and then a solution of copper (I) chloride (13 mg, 0.131 mmol) in concentrated hydrochloric acid (1 ml, 12.18 mmol) was added dropwise. The resulting mixture was stirred over the weekend at room temperature, briefly (ca. 10 min) warmed to 75° C., and then cooled and diluted with 10 ml of water and 10 ml of ethyl acetate. The phases were separated and the organic phase was washed with 10 ml of water. The combined organics were dried (sodium sulfate) and concentrated. The residue was purified by flash chromatography on a Biotage Horizon, 25S column, eluting with 1 column volume of 100% dichloromethane followed by a gradient of 0 to 100% ethyl acetate in dichloromethane over 10 column volumes to provide the title compound (8.0 mg, 0.016 mmol, 15.38% yield). Mass spectrum (ESI) 498.1 (M+1). $^1$H NMR (500 MHz, CDCl$_3$): δ 8.33 (d, J=8.5 Hz, 2H), 7.94 (d, J=8.0 Hz, 2H), 7.94 (s, 1H), 7.51 (s, 1H), 7.00-7.14 (m, 2H), 6.32 (br t, J=5.5 Hz, 1H), 3.48 (septet, J=6.5 Hz, 1H), 3.39 (t, J=6.0 Hz, 2H), 2.74-2.92 (m, 4H), 1.98-2.13 (m, 3H), 1.46 (d, J=7.0 Hz, 6H), 1.12-1.30 (m, 2H).

Example 118

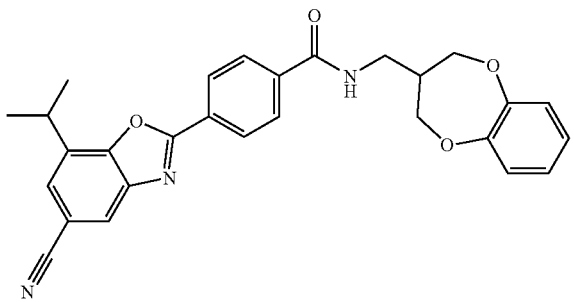 [SMILES: CC(C)c1cc(C#N)cc2nc(-c3ccc(C(=O)NCC4COc5ccccc5OC4)cc3)oc12]

4-(5-Cyano-7-isopropyl-1,3-benzoxazol-2-yl)-N-(3,4-dihydro-2H-1,5-benzodioxepin-3-ylmethyl)benzamide Step A. 2H-1,5-Benzodioxepin-3(4H)-one To a solution of 3,4-dihydro-2H-1,5-benzodioxepin-3-ol (1 g, 6.02 mmol) in dichloromethane (20 ml) was added Dess-Martin periodinane (2.8 g, 6.60 mmol). The mixture was stirred overnight at 25° C., and then purified by flash chromatography on a Biotage Horizon, 40M column, eluting with 1 column volume of 100% dichloromethane, followed by a gradient of 0 to 100% ethyl acetate in dichloromethane over 10 column volumes, to provide the title compound (964 mg, 5.87 mmol, 98% yield). $^1$H NMR (500 MHz, CDCl$_3$): δ 6.99 (m, 4H), 4.72 (s, 4H).

Step B. 1-(3,4-Dihydro-2H-1,5-benzodioxepin-3-yl)methanamine

Sodium hydride (60% in mineral oil) (143 mg, 3.56 mmol) was suspended in tetrahydrofuran (10 ml) and the mixture was cooled to 0° C. To the cold mixture was added triethylphosphonoacetate (0.598 ml, 3.02 mmol). After stirring for 10 min, a solution of 2H-1,5-benzodioxepin-3(4H)-one (450 mg, 2.74 mmol) in tetrahydrofuran (2 ml) was added dropwise. The cooling bath was removed and the mixture was warmed to room temperature and for 1 h, the quenched by addition of half-saturated sodium bicarbonate solution (20 ml). The mixture was extracted with 3×10 ml of ethyl acetate. The combined organics were dried (sodium sulfate), filtered, and concentrated to provide the desired ethyl ester, which was used without further purification. To a solution of this ester (671 mg, 2.86 mmol) and ammonium formate (903 mg, 14.32 mmol) in methanol (10 ml) was added Pd/C (70 mg, 0.658 mmol). The mixture began to reflux on completion of the addition, and then was heated in an oil bath to maintain the reflux for a total of 2 h. The mixture was the cooled, filtered through a pad of Celite, washing liberally with methanol, and concentrated. The residue was purified by flash chromatography on a Biotage Horizon, 40S column, eluting with 1 column volume of 100% hexanes followed by a gradient of 0 to 100% ethyl acetate in hexanes over 10 column volumes to provide the reduced ester, which was used without further purification. To a suspension of this ester (212 mg, 0.897 mmol) in tetrahydrofuran (4 ml), methanol (2 ml), and water (1 ml) was added lithium hydroxide (43.0 mg, 1.795 mmol). The mixture was stirred overnight at room temperature, at which point a clear solution had formed. The reaction mixture was concentrated to a small volume and then diluted with 10 ml of 1 N HCl and 10 ml of ethyl acetate. The phases were separated and the aqueous phase was extracted with 2×10 ml of ethyl acetate. The combined organics were washed with 10 ml of brine, dried (sodium sulfate), and concentrated, and then dried overnight under vacuum to provide the desired acid, which was used without further purification. This acid (200 mg, 0.961 mmol) was dissolved in toluene (2 ml), and diphenylphosphorylazide (0.25 ml, 1.158 mmol) and triethylamine (0.19 ml, 1.363 mmol) were added. The mixture was heated to 100° C. and stirred for 30 min at this temperature, and then allowed to stand overnight at room temperature, at which point LC/MS analysis showed no starting material. The reaction mixture was then concentrated and the residue was purified by flash chromatography on a Biotage Horizon, 25S column, eluting with 1 column volume of 100% dichloromethane followed by a gradient of 0 to 100% ethyl acetate in dichloromethane over 10 column volumes to provide the title compound (106 mg, 0.591 mmol, 61.6% yield). $^1$H NMR (500 MHz, CDCl$_3$): δ 6.87-7.02 (m, 4H), 5.53 (br d, 2H), 4.01 (ABq, J$_{AB}$=11.5 Hz, 2H), 3.53 (m, 2H), 2.50 (m, 1H).

Step C. 4-(5-Cyano-7-isopropyl-1,3-benzoxazol-2-yl)-N-(3,4-dihydro-2H-1,5-benzodioxepin-3-ylmethyl)benzamide The title compound was prepared, as a mixture, from 4-(5-cyano-7-isopropyl-1,3-benzoxazol-2-yl)benzoic acid (INTERMEDIATE 2), and 1-(3,4-dihydro-2H-1,5-benzodioxepin-3-yl)methanamine as described in EXAMPLE 1. Mass spectrum (ESI) 468.0 (M+1). $^1$H NMR (500 MHz, CDCl$_3$): δ 8.31 (d, J=8.5 Hz, 2H), 7.96 (d, J=8.5 Hz, 2H), 7.93 (d, J=1.5 Hz, 1H), 7.51 (d, J=1 Hz, 1H), 6.90-7.02 (m, 4H), 4.29 (m, 4H), 3.75 (t, J=6 Hz, 2H), 3.47 (septet, J=7 Hz, 1H), 2.65 (m, 1H), 1.46 (d, J=6.5 Hz, 6H).

The invention claimed is:

1. A compound having Formula I, or a pharmaceutically acceptable salt thereof, wherein

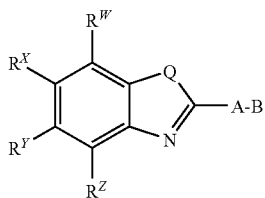

I

Q is O;

A is a difunctional cyclic group selected from 1,4-phenylene, 2,5-pyridinylene, and 2,5-pyrimidinylene, wherein A is optionally substituted with 1-3 substituent groups R$^1$;

Each R$^1$ is independently selected from the group consisting of halogen, C$_1$-C$_3$alkyl, C$_2$-C$_3$alkenyl, C$_2$-C$_3$alkynyl, and —OC$_1$-C$_3$alkyl, wherein each alkyl, alkenyl, and alkynyl substituent is optionally substituted with 1-5 halogens;

Each R$^2$ is independently selected from the group consisting of H, C$_1$-C$_3$alkyl, C$_2$-C$_3$alkenyl, and C$_2$-C$_3$alkynyl, wherein each alkyl, alkenyl, and alkynyl substituent is optionally substituted with 1-5 halogens;

R$^W$ is selected from the group consisting of (a) C$_1$-C$_5$alkyl which is optionally substituted with 1-5 halogens, (b) C$_{2-5}$ alkenyl which is optionally substituted with 1-5 halogens; (c) —OC$_1$-C$_5$ alkyl which is optionally substituted with 1-5 halogens, (d)-SC$_1$-C$_5$ alkyl which is optionally substituted with 1-5 halogens, (e) —OC$_{2-5}$ alkenyl which is optionally substituted with 1-5 halogens, (f) C$_3$-C$_6$cycloalkyl, (g) phenyl, (h) a 5-6 membered saturated or partly unsaturated heterocyclic group having 1-3 heteroatoms independently selected from N, S and O, (i) a 5-7 membered heteroaromatic group having 1-3 heteroatoms independently selected from N, S, and O, (j) —C(=O)OC$_{1-3}$alkyl which is optionally substituted with 1-5 halogens, and (k) —C(=O)OH, wherein said C$_3$-C$_6$cycloalkyl, phenyl, 5-6 membered saturated or partly unsaturated heterocyclic group, and 5-7 membered heteroaromatic group are optionally substituted with 1-3 substituents independently selected from halogen, CH$_3$, CF$_3$, —OCH$_3$, and —OCF$_3$;

R$^Y$ is selected from the group consisting of halogen, CH$_3$, CF$_3$, —OCH$_3$, —OCF$_3$, —CN, phenyl, and a 6-membered heteroaroaromatic group having 1-2 N, wherein phenyl and the 6-membered heteroaroaromatic group are optionally substituted with 1-3 substituents independently selected from halogen, CH$_3$, CF$_3$, —OCH$_3$, and —OCF$_3$;

R$^X$ and R$^Z$ are each selected from the group consisting of H, halogen, CH$_3$, CF$_3$, —OCH$_3$, and —OCF$_3$;

B is selected from the group consisting of:
(a) —C(=O)N(R$^3$)(CR$^4$R$^5$)$_x$(CR$^6$R$^7$)$_y$D$^2$, and
(b) —C(=O)N(R$^3$)(CR$^4$R$^5$)D$^5$;

R$^3$ is selected from the group consisting of H and C$_1$-C$_3$alkyl;

R$^4$ is selected from the group consisting of H, C$_1$-C$_3$alkyl, CF$_3$, —C(=O)OH, and —C(=O)OC$_1$-C$_3$alkyl;

R$^5$ is selected from the group consisting of H, C$_1$-C$_3$alkyl, and CF$_3$;

R$^6$ is selected from the group consisting of H, C$_1$-C$_3$alkyl, CF$_3$, —C(=O)OH, and —C(=O)OC$_1$-C$_3$alkyl;

R$^7$ is selected from the group consisting of H, C$_1$-C$_3$alkyl, CF$_3$, and phenyl, which is optionally substituted with 1-3 groups independently selected from halogen, CH$_3$, CF$_3$, —OCH$_3$, and —OCF$_3$;

x is 0 or 1;

y is 0, 1, or 2;

D$^2$ is a cyclic group selected from the group consisting of
(a) C$_3$-C$_8$Cycloalkyl which optionally comprises 1-2 double bonds and is optionally fused to a phenyl ring,
(b) Bicyclic C$_6$-C$_{12}$Cycloalkyl optionally comprising 1-2 double bonds,
(c) A 4-8 membered saturated or partly unsaturated heterocyclic ring comprising 1-3 ring members independently selected from —O— and —S—, optionally one carbonyl group, and optionally 1-2 double bonds, said heterocyclic ring being connected to the remainder of the structure represented by Formula I through a carbon atom of the heterocyclic ring, wherein said heterocyclic ring is optionally fused to a phenyl ring or to a C$_5$-C$_7$Cycloalkyl,
(d) A spirocyclic group having two rings joined by a spirocyclic linkage through a carbon atom wherein each ring is a 5-7-membered ring, wherein D$^2$ optionally comprises in either ring of the spirocyclic group (i) optionally 1-2 ring members independently selected from —O— and —S—, (ii) optionally one carbonyl group, and (iii) optionally 1-2 double bonds, wherein either ring of the spirocyclic group D$^2$ is optionally fused to a phenyl ring or to a C$_5$-C$_7$Cycloalkyl,
(e) An aromatic ring selected from phenyl and naphthyl, and
(f) A 5-7 membered heteroaromatic ring having 1-3 heteroatoms independently selected from N, S, and O, and optionally having one —C(=O)— group as a ring member, said heteroaromatic ring being connected to the right side of the structure represented by Formula I through a carbon atom of the heteroaromatic ring, wherein said heteroromatic ring is optionally fused to a phenyl ring;

Wherein said cyclic groups D$^2$ defined in (a)-(f), including optional fused rings, are optionally substituted with 1-5 substitutents independently selected from halogen, —CN, —NO$_2$, —OH, —N(R$^3$)$_2$—, C$_1$-C$_7$alkyl, C$_2$-C$_7$alkenyl, CF$_3$, —OC$_1$-C$_5$alkyl, —C$_1$-C$_5$alkylene-OC$_1$-C$_5$alkyl, —OCF$_3$, —C(=O)C$_1$-C$_5$alkyl, —C(=O)OC$_1$-C$_5$alkyl, —C(=O)OH, and —NR$^3$C(=O)C$_1$-C$_5$alkyl, and are optionally substituted with one substituent selected from the group consisting of 4,4,5,5-tetramethyl-1,3,2-dioxaborolan-2-yl and a cyclic group $D^4$, wherein $C_1$-$C_7$alkyl, $C_2$-$C_7$alkenyl, and $OC_1$-$C_5$alkyl in all uses are optionally substituted with 1-9 halogens, wherein $D^4$ is connected directly to $D^2$ or is connected to $D^2$ through a linking group $L^4$, Wherein $D^4$ is selected from the group consisting of (a) phenyl, (b) naphthyl, (c) $C_3$-$C_8$cycloalkyl optionally having 1-2 double bonds, (d) a saturated or partially unsaturated monocyclic or bicyclic 4-10 membered heterocycle having 1-3 heteroatoms independently selected from N, O, and S and optionally one —C(=O)— group, said heterocycle optionally having 1-2 double bonds, and (e) a monocyclic or bicyclic 5-12 membered heteroaromatic group having 1-3 heteroatoms independently selected from N, S, and O and optionally having one —C(=O)— group, and $L^4$ is selected from the group consisting of —C(=O)—, —S—, —S(O)$_2$—, —O—, —N(R$^3$)C(=O)—, —CH$_2$N(R$^3$)C(=O)—, —CH$_2$C(=O)N(R$^3$)—, —N(R$^3$)S(O)$_2$—, —CH$_2$N(R$^3$)S(O)$_2$—, —CH$_2$S(O)$_2$N(R$^3$)—, —C$_2$-C$_5$alkenylene-, and —C$_1$-C$_5$alkylene- which optionally comprises one heteroatom or a difunctional group selected from O, S, —S(O)$_2$—, —NR$^3$—, —N(R$^3$)C(=O)—, and —N(R$^3$)S(O)$_2$— between 2 adjacent carbons of the —C$_1$-C$_5$alkylene-group, wherein $D^4$ is optionally substituted with 1-3 substituents independently selected from halogen, —CN, —NO$_2$, —N(R$^3$)$_2$—, —OH, C$_1$-C$_7$alkyl, C$_2$-C$_7$alkenyl, CF$_3$, —OC$_1$-C$_5$alkyl, —C$_1$-C$_5$alkylene-OC$_1$-C$_5$alkyl, CO$_2$H, CO$_2$C$_1$-C$_5$alkyl, and —OCF$_3$, and is optionally substituted with one cyclic group $D^6$ bonded directly to $D^4$ or connected to $D^4$ through a linking group $L^6$, wherein $D^6$ has the same selections as $D^4$, and $L^6$ has the same selections as $L^4$, and $D^6$ is optionally substituted with 1-3 substituents independently selected from halogen, —CN, —NO$_2$, —N(R$^3$)$_2$—, —OH, C$_1$-C$_7$alkyl, C$_2$-C$_7$alkenyl, CF$_3$, —OC$_1$-C$_5$alkyl, —C$_1$-C$_5$alkylene-OC$_1$-C$_5$alkyl, and —OCF$_3$, wherein the C$_1$-C$_7$alkyl, C$_2$-C$_7$alkenyl, and —OC$_1$-C$_5$alkyl groups in all uses in substituents on D4 and D6 are optionally substituted with 1-5 halogens; and $D^5$ is selected from the group consisting of –OC$_1$-C$_7$alkyl, —CH$_2$S(O)$_2$C$_1$-C$_7$alkyl, C$_1$-C$_{15}$alkyl, C$_2$-C$_{15}$alkenyl, C$_2$-C$_{15}$alkynyl, —NR$^3$C$_1$-C$_7$alkyl, —NR$^3$C(=O)OC$_1$-C$_7$alkyl, and —OC(=O)OC$_1$-C$_7$alkyl, wherein the C$_1$-C$_{15}$alkyl, C$_2$-C$_{15}$alkenyl, C$_2$-C$_{15}$alkynyl, and C$_1$-C$_7$alkyl groups of $D^5$ are optionally substituted with 1-9 halogens and are optionally substituted with one group selected from —N(R$^3$)$_2$, —N(R$^3$)C(=O)OC$_1$-C$_7$alkyl, —N(R$^3$)C(=O)C$_1$-C$_7$alkyl, and —OH, wherein the C$_1$-C$_7$alkyl groups of the —N(R$^3$)C(=O)OC$_1$-C$_7$alkyl and —N(R$^3$)C(=O)C$_1$-C$_7$alkyl substituents on $D^5$ are optionally substituted with 1-9 halogens.

2. The compound of claim 1, or a pharmaceutically acceptable salt thereof, wherein Q is O;

A is a difunctional cyclic group selected from 1,4-phenylene, 2,5-pyridinylene, and 2,5-pyrimidinylene, wherein A is optionally substituted with 1-3 substituent groups R$^1$;

Each R$^1$ is independently selected from the group consisting of halogen, CH$_3$, CF$_3$, —OCH$_3$, and —OCF$_3$;

R$^W$ is selected from the group consisting of (a) C$_1$C$_5$alkyl which is optionally substituted with 1-5 F, (b) C$_{2-3}$ alkenyl which is optionally substituted with 1-3 F, (c) —OC$_1$-C$_3$ alkyl which is optionally substituted with 1-3 F, (d)-SC$_1$-C$_3$ alkyl which is optionally substituted with 1-3 F, (e) —OC$_{2-3}$ alkenyl which is optionally substituted with 1-3 F, (f) C$_3$-C$_6$cycloalkyl, (g) phenyl, (h) pyridyl, (i) —C(=O)OC$_{1-3}$ alkyl which is optionally substituted with 1-3 F, and (k) —C(=O)OH, wherein said C$_3$-C$_6$cycloalkyl, phenyl, and pyridinyl substituents are optionally substituted with 1-3 substituents independently selected from halogen, CH$_3$, CF$_3$, —OCH$_3$, and —OCF$_3$;

R$^Y$ is selected from the group consisting of halogen, CH$_3$, CF$_3$, —OCH$_3$, —OCF$_3$, and —CN; and R$^X$ and R$^Z$ are each selected from the group consisting of H, halogen, CH$_3$, CF$_3$, —OCH$_3$, and —OCF$_3$.

3. The compound of claim 1 having Formula Ia, or a pharmaceutically acceptable salt thereof:

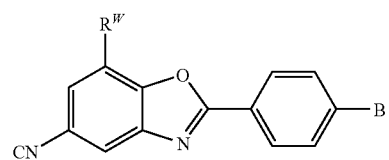

wherein R$^W$ is selected from the group consisting of C$_1$-C$_4$alkyl which is optionally substituted with 1-3 F, C$_{2-3}$ alkenyl, —OCH$_3$, —OCF$_3$, —SCH$_3$, —SCF$_3$, cyclopropyl, —C(=O)OC$_{1-3}$alkyl, and phenyl which is optionally substituted with 1-3 substituents independently selected from halogen, CH$_3$, CF$_3$, —OCH$_3$, and —OCF$_3$;

R$^3$ is selected from the group consisting of H and CH$_3$;

R$^4$ is selected from the group consisting of H, —C(=O)OH, and —C(=O)OC$_1$-C$_3$alkyl;

R$^5$ is selected from the group consisting of H and CH$_3$;

R$^6$ and R$^7$ are H;

x is 0 or 1; and y is 0, 1, or 2.

4. The compound of claim 3, wherein:

R$^W$ is —CH(CH$_3$)$_2$; and

R$^3$ is H.

5. The compound of claim 3, wherein:

R$^W$ is —CH(CH$_3$)$_2$;

R$^3$ is H;

$D^2$ is a cyclic group selected from phenyl, indolyl, imidazolyl, cyclopropyl, C$_4$-C$_7$ cycloalkyl which is optionally fused to a phenyl, C$_5$-C$_6$ cycloalkenyl, and a 6-7-membered cyclic monoether or diether fused to a phenyl, wherein $D^2$ is optionally substituted with 1-3 substitutents independently selected from halogen, C$_1$-C$_3$ alkyl, CF$_3$, —OCH$_3$, —OCF$_3$, —CO$_2$H, —CO$_2$CH$_3$, —NO$_2$, —OH, and C$_1$-C$_2$alkylene-O—C$_1$-C$_4$alkyl optionally substituted with 1-9 F, and is optionally substituted with one substituent selected from 4,4,5,5-tetramethyl -1,3,2-dioxaborolan-2-yl and $D^4$, wherein $D^4$ is connected directly to $D^2$ or is connected to $D^2$ through a linking group $L^4$;

$D^4$ is a cyclic group selected from phenyl, $C_5$-$C_6$ cycloalkyl, $C_5$-$C_6$ cycloalkenyl, pyrrolidinyl, piperidinyl, piperazinyl, thiazolyl, pyrazolyl, furanyl, pyridyl, indolyl, benzothiophenyl, benzofuranyl, and naphthyl, wherein $D^4$ is optionally substituted with 1-3 substituents independently selected from $C_1$-$C_5$ alkyl, $CF_3$, $C_2$-$C_6$ alkenyl, —$OC_1$-$C_4$alkyl, —$OCF_3$, halogen, —$CO_2H$, —$CO_2C_1$-$C_5$alkyl, —CN, and —OH, and is optionally substituted with one group $D^6$, which is optionally connected directly to $D^4$ or is connected to $D^4$ through a linking group $L^6$;

$D^6$ is selected from the group consisting of phenyl, $C_3$-$C_6$ cycloalkyl, pyridyl, morpholinyl, pyrrolidinyl, furanyl, 2-oxazolidinonyl and 2-azetidinonyl, wherein $D^6$ is optionally substituted with 1-2 substitutents independently selected from $C_1$-$C_3$alkyl, $CF_3$, —$OC_1$-$C_3$alkyl, —$OCF_3$, Cl, and F;

$L^4$ is selected from the group consisting of —$CH_2$—, —O—, —C(=O)—, —$CH_2CH_2NHCH_2$—, —$CH_2C(=O)NH$— and $C_2$-$C_3$ alkenylene;

$L^6$ is selected from —$S(O)_2$— and $C_2$-$C_3$ alkenylene; and $D^5$ is selected from the group consisting of $C_2$-$C_3$ alkynyl and $C_1$-$C_{12}$ alkyl, wherein $C_1$-$C_{12}$alkyl is optionally substituted with 1-3F.

6. The compound of claim 1, wherein $D^2$ is a cyclic group selected from phenyl, indolyl, imidazolyl, cyclopropyl, $C_4$-$C_7$ cycloalkyl which is optionally fused to a phenyl, $C_5$-$C_6$ cycloalkenyl, and a 6-7-membered cyclic monoether or diether fused to a phenyl, wherein $D^2$ is optionally substituted with 1-3 substitutents independently selected from halogen, $C_1$-$C_3$ alkyl, $CF_3$, —$OCH_3$, —$OCF_3$, —$CO_2H$, —$CO_2CH_3$, —$NO_2$, —OH, and $C_1$-$C_2$alkylene-O—$C_1$-$C_4$alkyl optionally substituted with 1-9 F, and is optionally substituted with one substituent selected from 4,4,5,5-tetramethyl -1,3,2-dioxaborolan-2-yl and $D^4$, wherein $D^4$ is connected directly to $D^2$ or is connected to $D^2$ through a linking group $L^4$.

7. The compound of claim 1, wherein $D^4$ is a cyclic group selected from phenyl, $C_5$-$C_6$ cycloalkyl, $C_5$-$C_6$ cycloalkenyl, pyrrolidinyl, piperidinyl, piperazinyl, thiazolyl, pyrazolyl, furanyl, pyridyl, indolyl, benzothiophenyl, benzofuranyl, and naphthyl, wherein $D^4$ is optionally substituted with 1-3 substituents independently selected from $C_1$-$C_5$ alkyl, $CF_3$, $C_2$-$C_6$ alkenyl, —$OC_1$-$C_4$alkyl, —$OCF_3$, halogen, —$CO_2H$, —$CO_2C_1$-$C_5$alkyl, —CN, and —OH, and is optionally substituted with one group $D^6$, which is optionally connected directly to $D^4$ or is connected to $D^4$ through a linking group $L^6$.

8. The compound of claim 1, wherein $D^6$ is selected from the group consisting of phenyl, $C_3$-$C_6$ cycloalkyl, pyridyl, morpholinyl, pyrrolidinyl, furanyl, 2-oxazolidinonyl and 2-azetidinonyl, wherein $D^6$ is optionally substituted with 1-2 substitutents independently selected from $C_1$-$C_3$alkyl, $CF_3$, —$OC_1$-$C_3$alkyl, —$OCF_3$, Cl, and F.

9. The compound of claim 1, wherein linking group $L^4$ is selected from the group consisting of —$CH_2$—, —O—, —C(=O)—, —$CH_2CH_2NHCH_2$—, —$CH_2C(=O)NH$— and $C_2$-$C_3$ alkenylene.

10. The compound of claim 1, wherein linking group $L^6$ is selected from —$S(O)_2$— and $C_2$-$C_3$ alkenylene.

11. The compound of claim 1, wherein $D^5$ is selected from the group consisting of $C_2$-$C_3$ alkynyl and $C_1$-$C_{12}$ alkyl, wherein $C_1$-$C_{12}$alkyl is optionally substituted with 1-3F.

12. The compound of claim 1, which is selected from the group consisting of the following compounds, or a pharmaceutically acceptable salt thereof:

| Ex. | Structure |
| --- | --- |
| 1 | 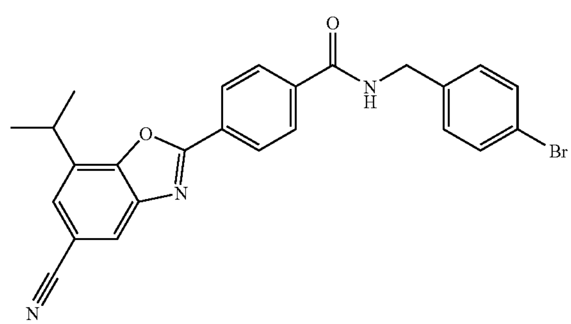 [SMILES: CC(C)c1cc(C#N)cc2nc(-c3ccc(C(=O)NCc4ccc(Br)cc4)cc3)oc12] |
| 2 | 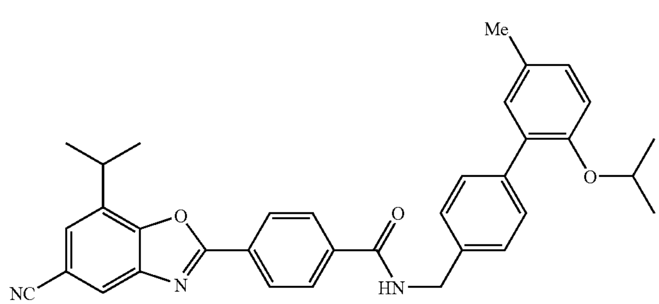 |

-continued

| Ex. | Structure |
|---|---|
| 3 | 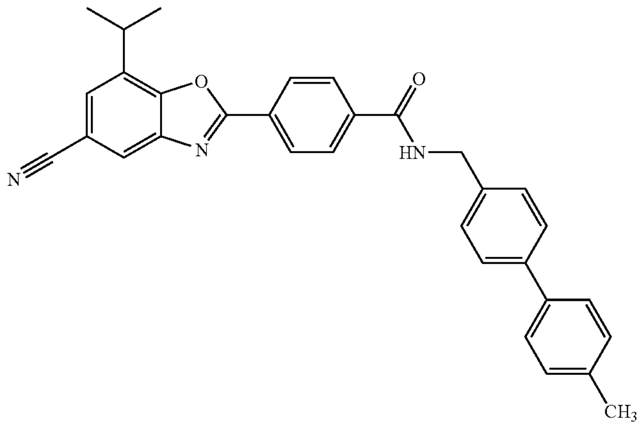 [SMILES: Cc1ccc(-c2ccc(CNC(=O)c3ccc(-c4nc5cc(C#N)cc(C(C)C)c5o4)cc3)cc2)cc1] |
| 4 | 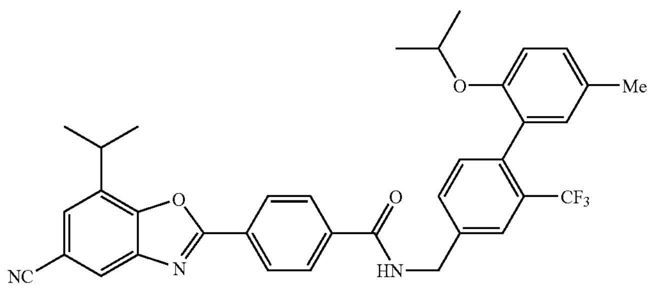 |
| 5 | 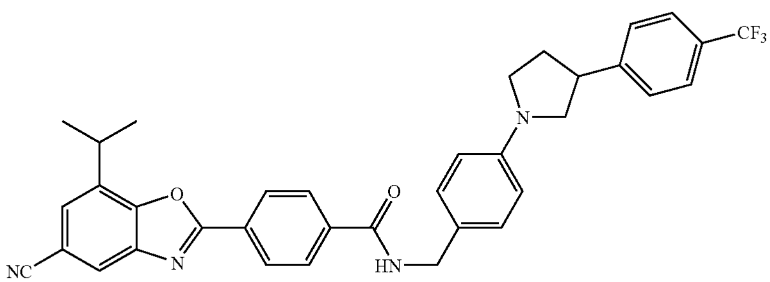 |
| 6 | 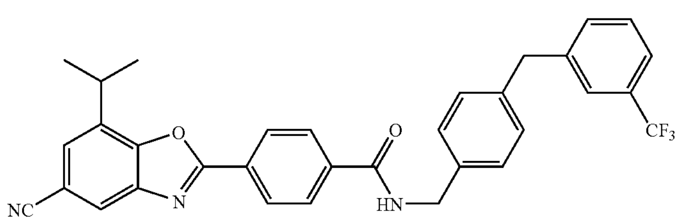 |
| 26 | 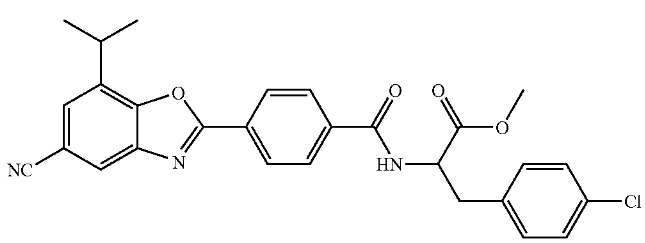 |

-continued
| Ex. | Structure |
|---|---|
| 34 | 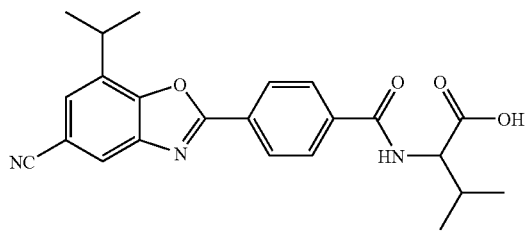 |
| 35 | 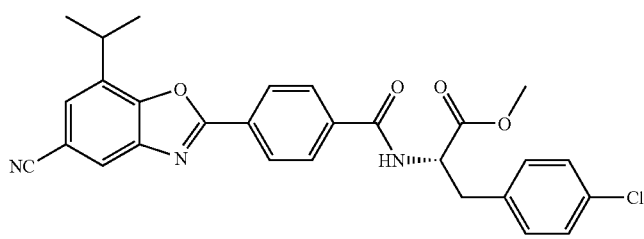 |
| 36 | 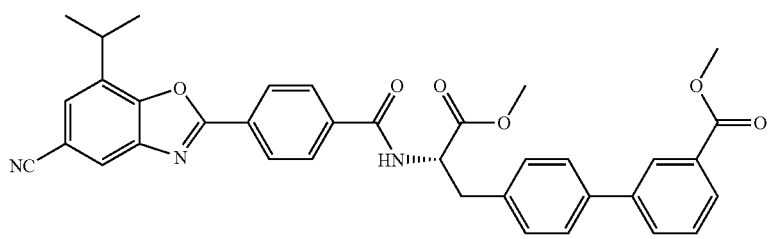 |
| 41 | 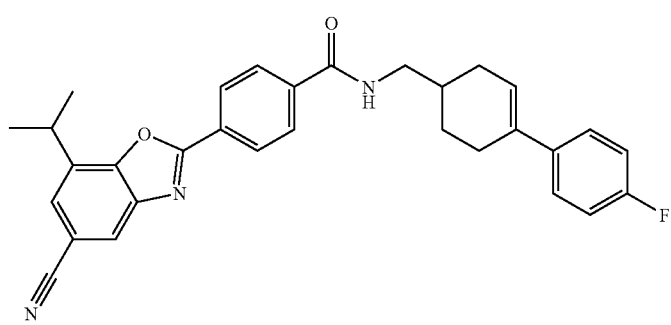 [SMILES: CC(C)c1cc(C#N)cc2nc(-c3ccc(C(=O)NCC4CC=C(c5ccc(F)cc5)CC4)cc3)oc12] |
| 42 | 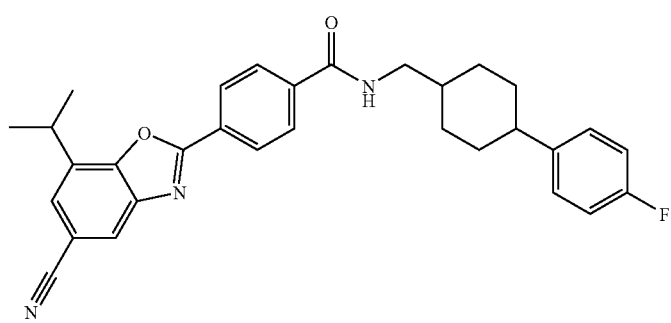 [SMILES: CC(C)c1cc(C#N)cc2nc(-c3ccc(C(=O)NCC4CCC(c5ccc(F)cc5)CC4)cc3)oc12] |

-continued
| Ex. | Structure |
|---|---|
| 43 | 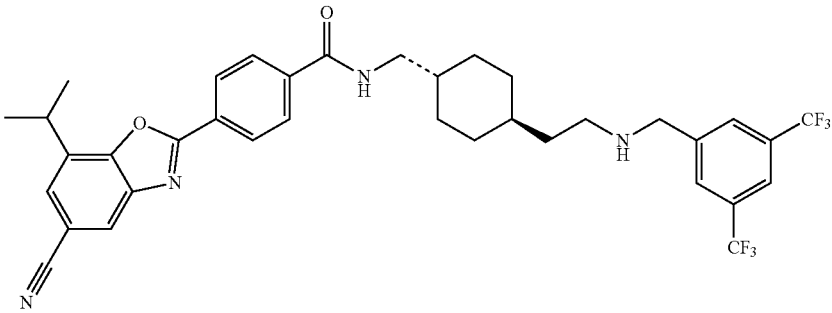 |
| 44 | 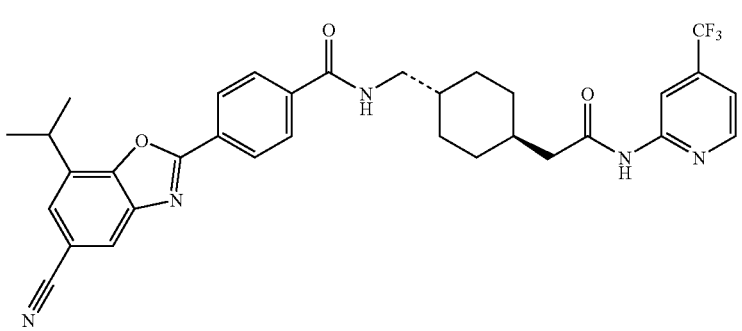 |
| 45 | 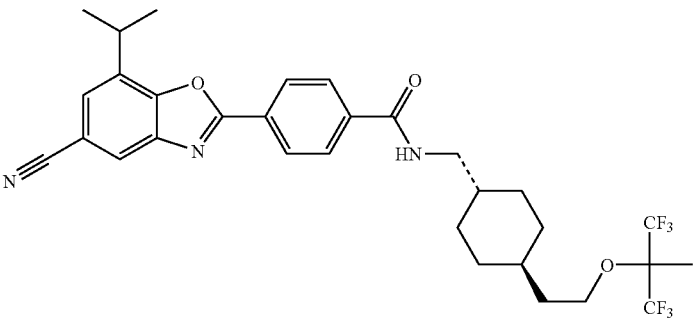 |
| 46 | 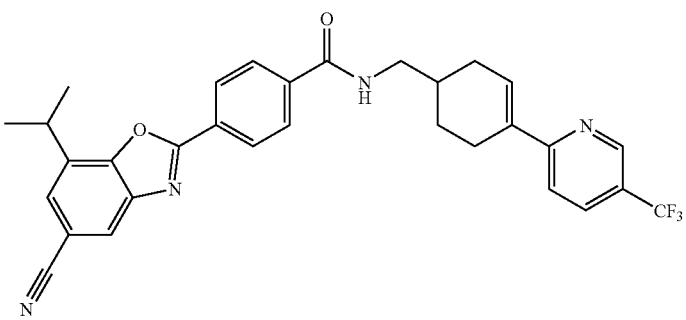 [SMILES: CC(C)c1cc(C#N)cc2nc(-c3ccc(C(=O)NCC4CC=C(c5ccc(C(F)(F)F)cn5)CC4)cc3)oc12] |
| 47 | 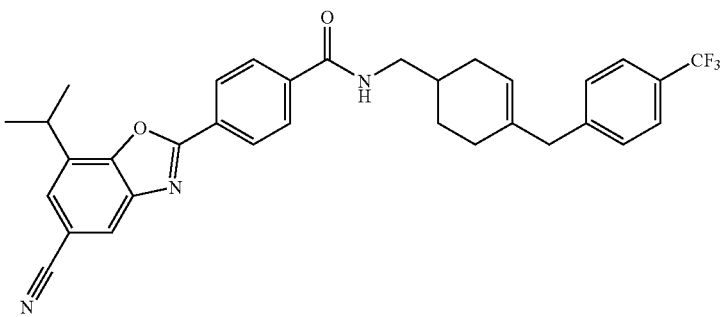 [SMILES: CC(C)c1cc(C#N)cc2nc(-c3ccc(C(=O)NCC4CC=C(Cc5ccc(C(F)(F)F)cc5)CC4)cc3)oc12] |

-continued
| Ex. | Structure |
|---|---|
| 86 | 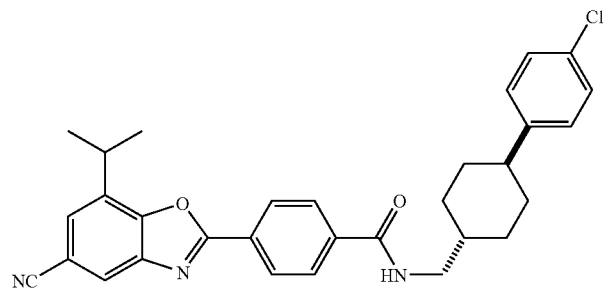 |
| 87 | 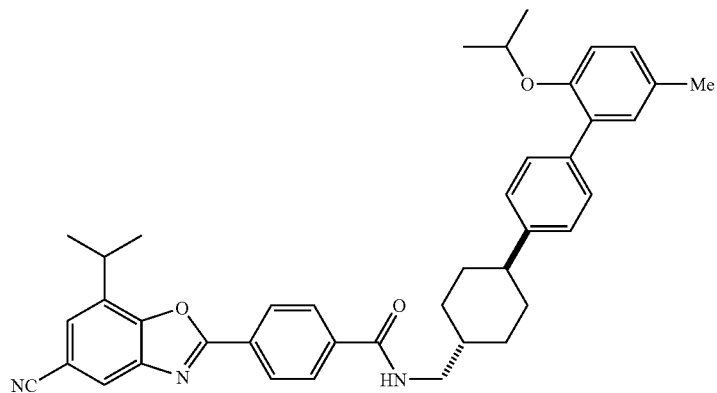 |
| 88 | 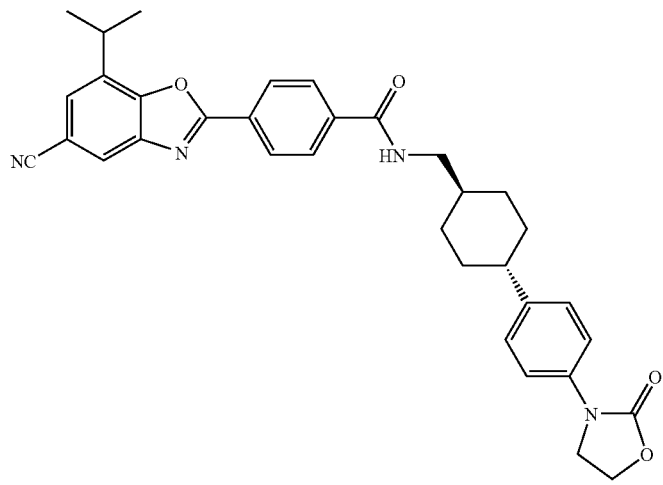 |

| Ex. | Structure |
|---|---|
| 89 | 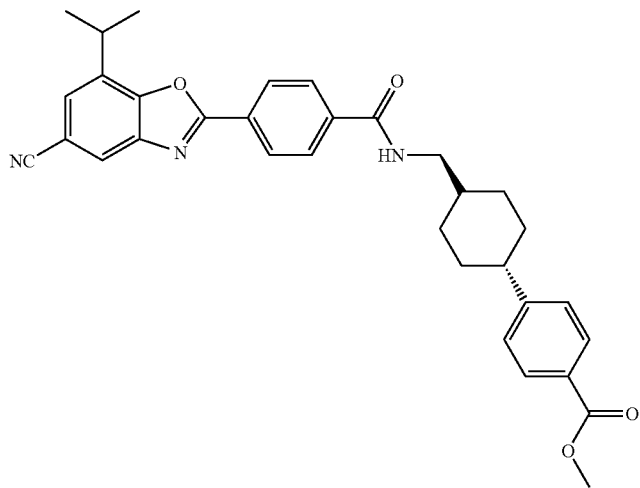 |
| 115 (a) | 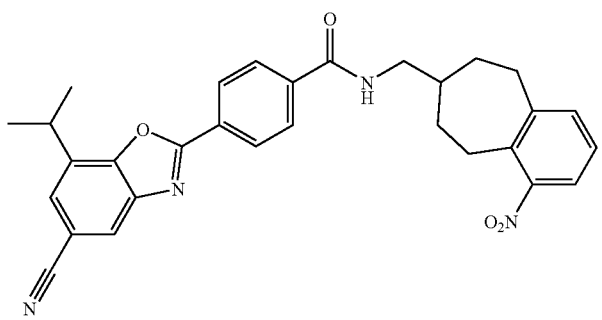 [SMILES: CC(C)c1cc(C#N)cc2nc(-c3ccc(C(=O)NCC4CCc5cccc([N+](=O)[O-])c5CC4)cc3)oc12] |
| 115 (b) | 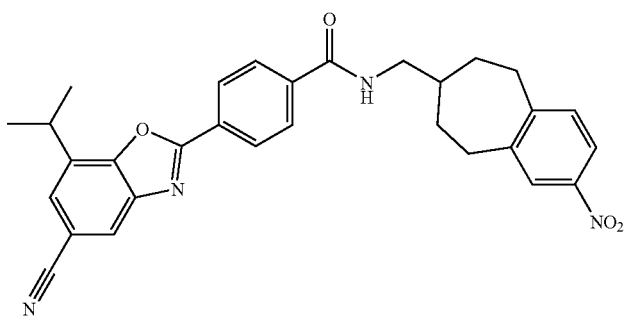 [SMILES: CC(C)c1cc(C#N)cc2nc(-c3ccc(C(=O)NCC4CCc5ccc([N+](=O)[O-])cc5CC4)cc3)oc12] |
| 116 | 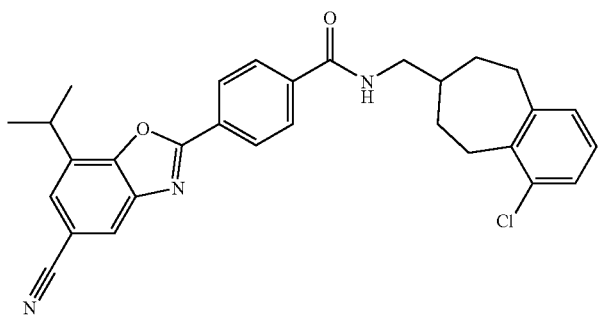 [SMILES: CC(C)c1cc(C#N)cc2nc(-c3ccc(C(=O)NCC4CCc5cccc(Cl)c5CC4)cc3)oc12] |

| Ex. | Structure |
|---|---|
| 117 | 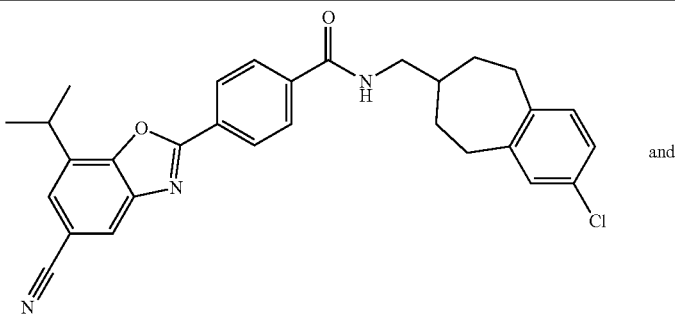 and |
| 118 | 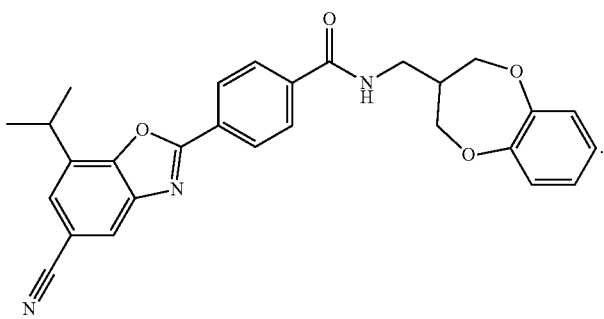 [SMILES: CC(C)c1cc(C#N)cc2nc(-c3ccc(C(=O)NCC4COc5ccccc5OC4)cc3)oc12] . |
13. The compound of claim 1, which is selected from the group consisting of the following compounds, or a pharmaceutically acceptable salt thereof:
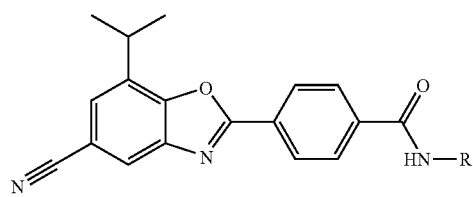
| Example | wherein R is |
|---|---|
| 7 | 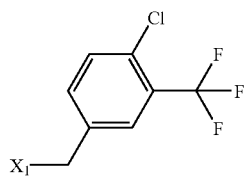 |
| 8 | 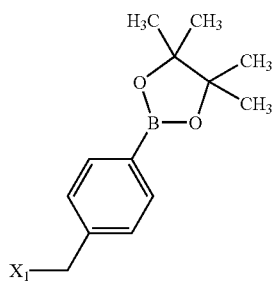 |
(a)
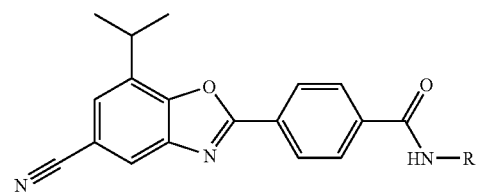
| Example | wherein R is |
|---|---|
| 9 | 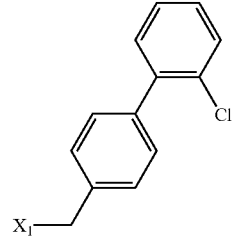 |
| 10 | 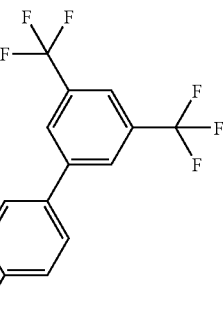 |

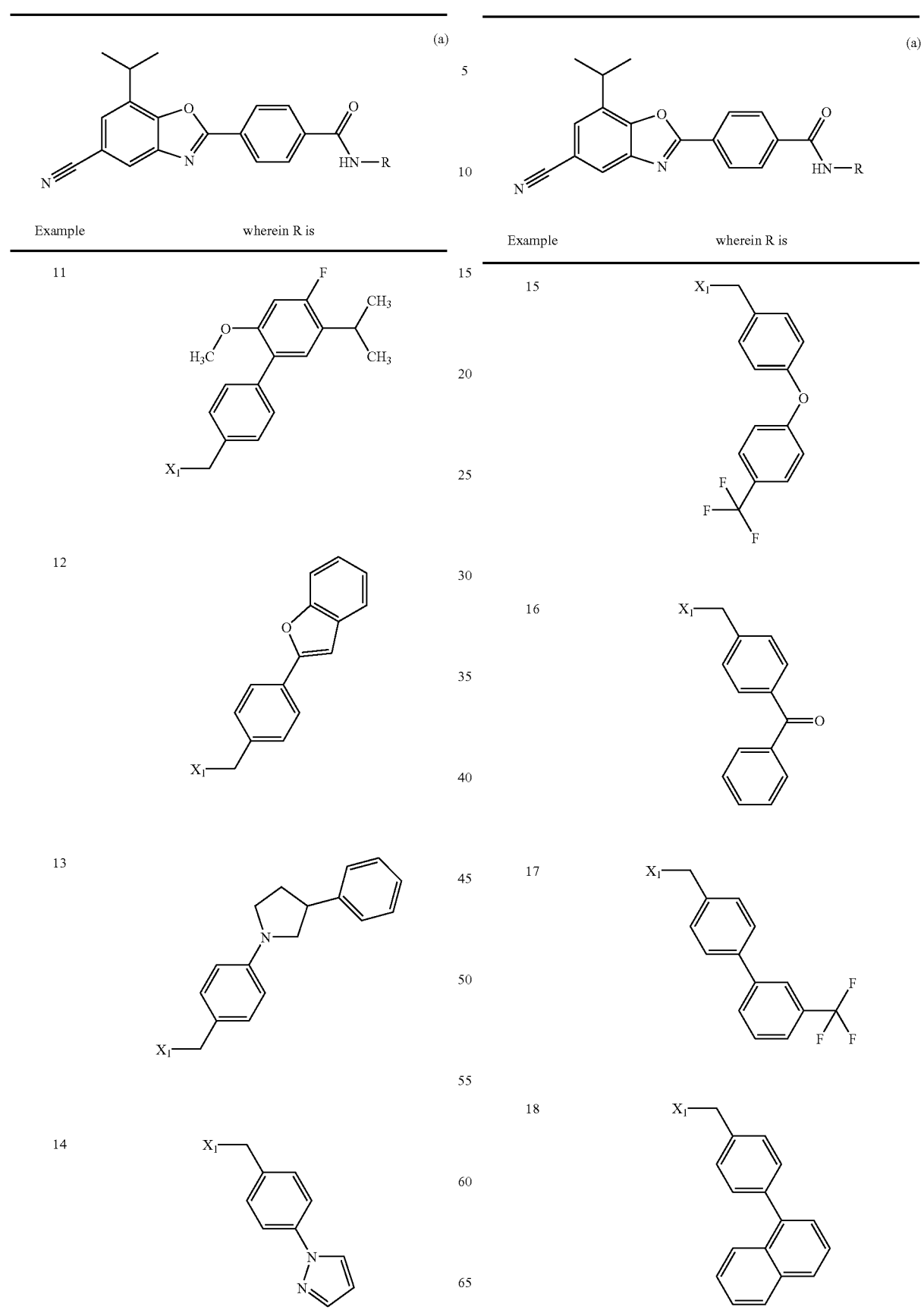

-continued
(a)
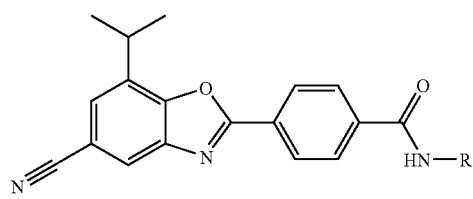
| Example | wherein R is |
|---|---|
| 19 | 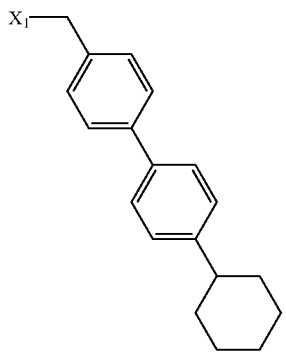 |
| 20 | 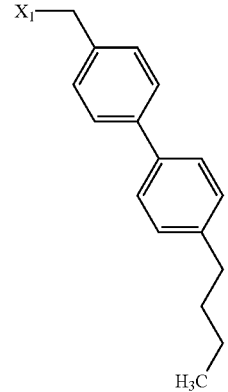 |
| 21 | 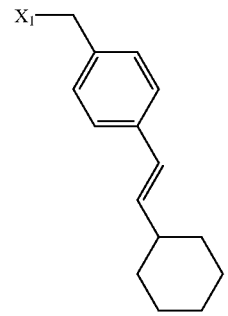 |
| 22 | 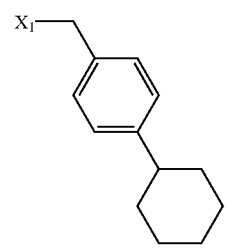 |
-continued
(a)
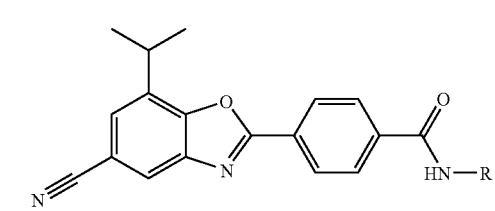
| Example | wherein R is |
|---|---|
| 23 | 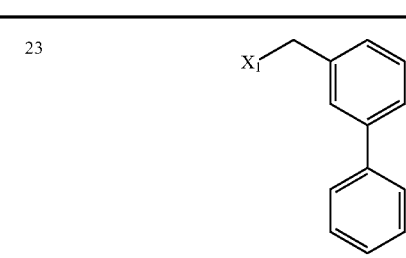 |
| 24 | 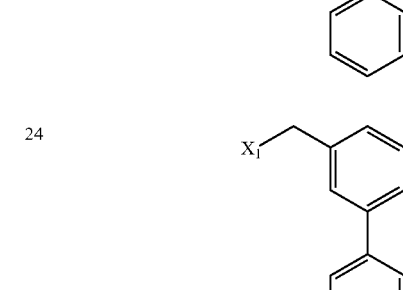 |
| 25 | 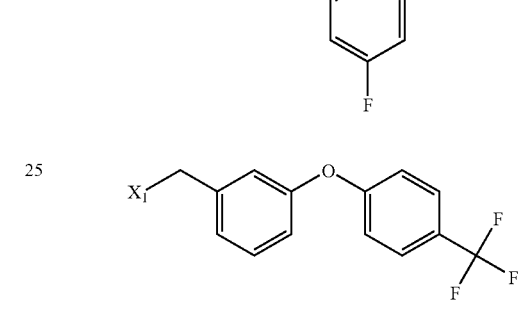 |
(b)
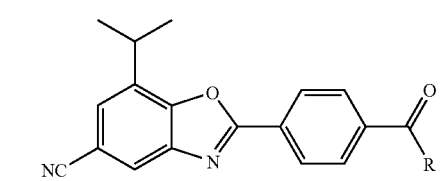
| Example | wherein R is |
|---|---|
| 27 | 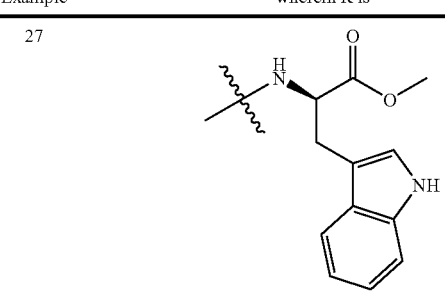 |

(b)
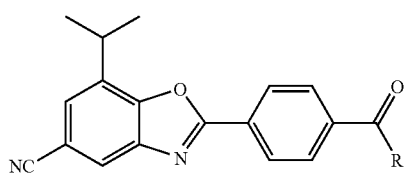
| Example | wherein R is |
|---|---|
| 28 | 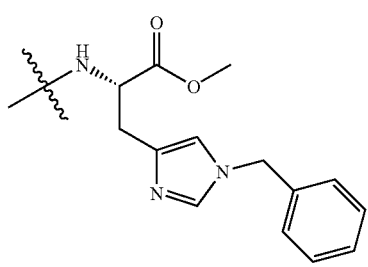 [SMILES: *N[C@@H](Cc1cn(Cc2ccccc2)cn1)C(=O)OC] |
| 29 | 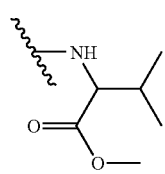 |
| 30 | 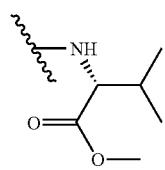 |
| 31 | 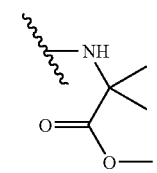 [SMILES: *NC(C)(C)C(=O)OC] |
| 32 | 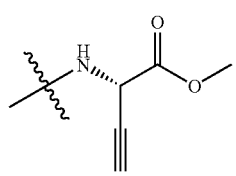 [SMILES: *N[C@@H](C#C)C(=O)OC] |
| 33 | 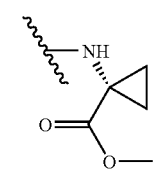 |
(c)
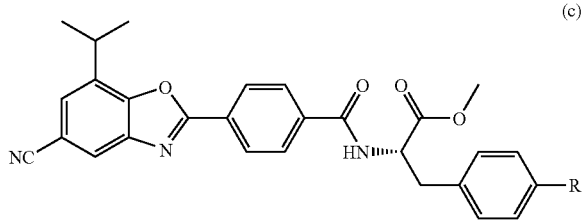
| Example | wherein R is |
|---|---|
| 37 |  |
| 38 |  |
| 39 |  |
| 40 |  |
(d)
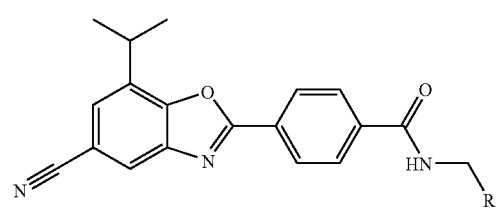
| Example | wherein R is |
|---|---|
| 48 | 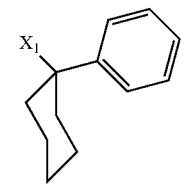 |

TABLE -continued (d)
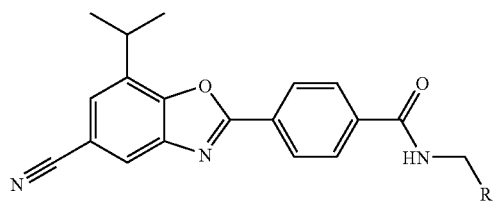
| Example | wherein R is |
|---|---|
| 49 | 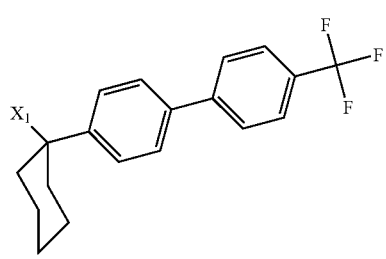 |
| 50 | 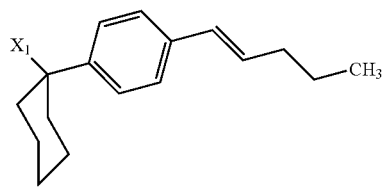 |
| 51 | 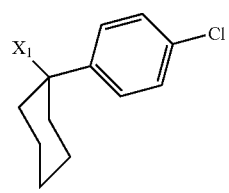 |
| 52 | 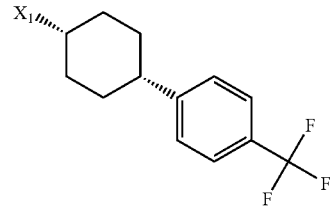 |
| 53 | 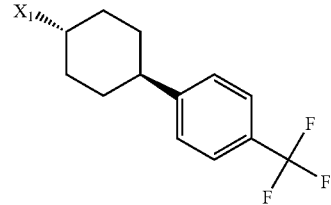 |
| 54 | 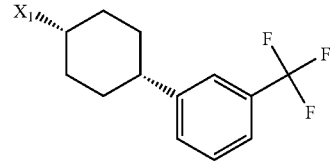 |
TABLE -continued (d)
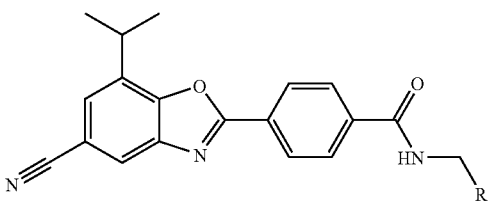
| Example | wherein R is |
|---|---|
| 55 | 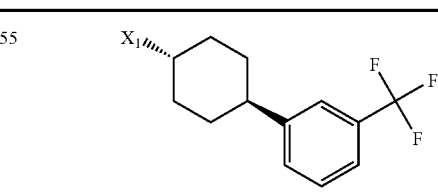 |
| 56 | 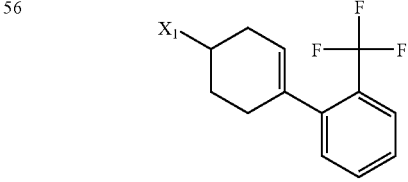 |
| 57 | 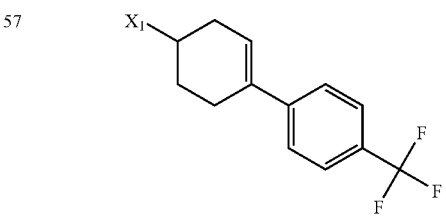 |
| 58 | 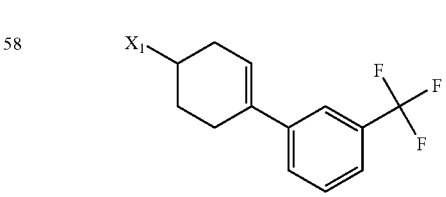 |
| 59 | 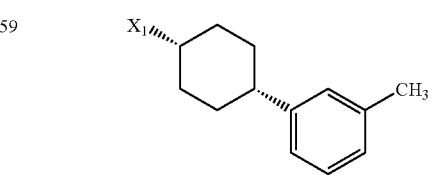 |
| 60 | 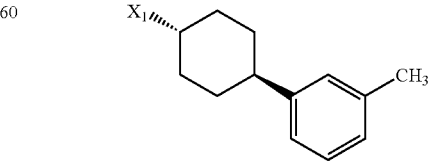 |

-continued (d)

| Example | wherein R is |
|---|---|
| 61 | 3,5-bis(trifluoromethyl)phenyl-cyclohexyl (trans, X₁ attached) |
| 62 | 3,5-bis(trifluoromethyl)phenyl-cyclohexyl (trans, X₁) |
| 63 | 4-tert-butylphenyl-cyclohexenyl |
| 64 | 4-tert-butylphenyl-cyclohexyl (trans) |
| 65 | 4-tert-butylphenyl-cyclohexyl (trans, X₁) |

-continued (d)

| Example | wherein R is |
|---|---|
| 66 | 3,5-dichlorophenyl-cyclohexenyl |
| 67 | 3-cyanophenyl-cyclohexyl (trans, X₁) |
| 68 | 3-cyanophenyl-cyclohexyl (trans, X₁) |
| 69 | 6-chloropyridin-3-yl-cyclohexenyl |
| 70 | 5-(trifluoromethyl)pyridin-2-yl-cyclohexyl (trans, X₁) |
| 71 | 5-(trifluoromethyl)pyridin-2-yl-cyclohexyl (trans, X₁) |

-continued
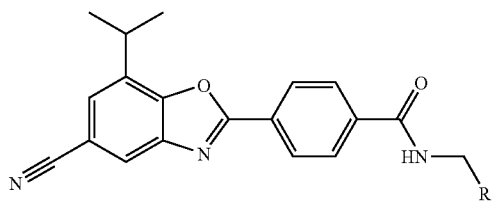
(d)
| Example | wherein R is |
|---|---|
| 72 | 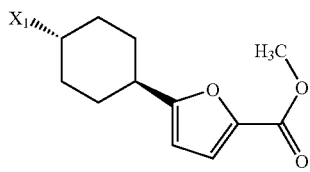 |
| 73 | 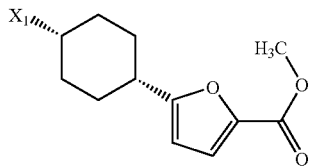 |
| 74 | |
| 75 | 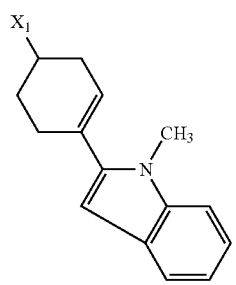 |
| 76 | 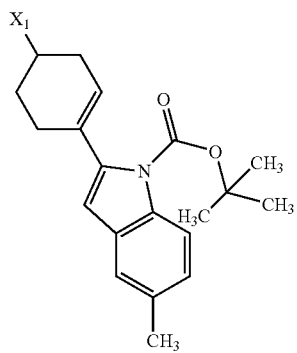 |
-continued
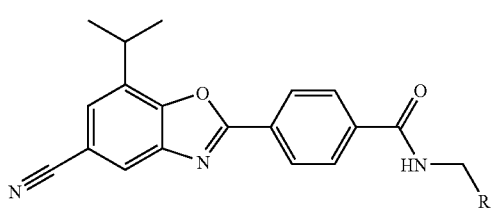
(d)
| Example | wherein R is |
|---|---|
| 77 | 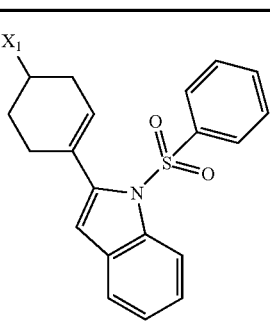 |
| 78 | 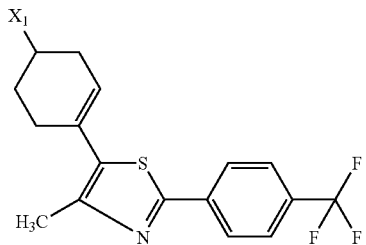 |
| 79 | 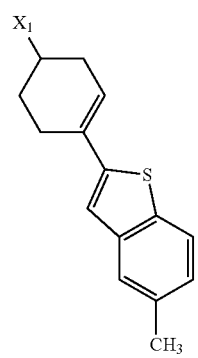 |
| 80 | 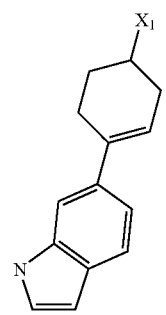 |

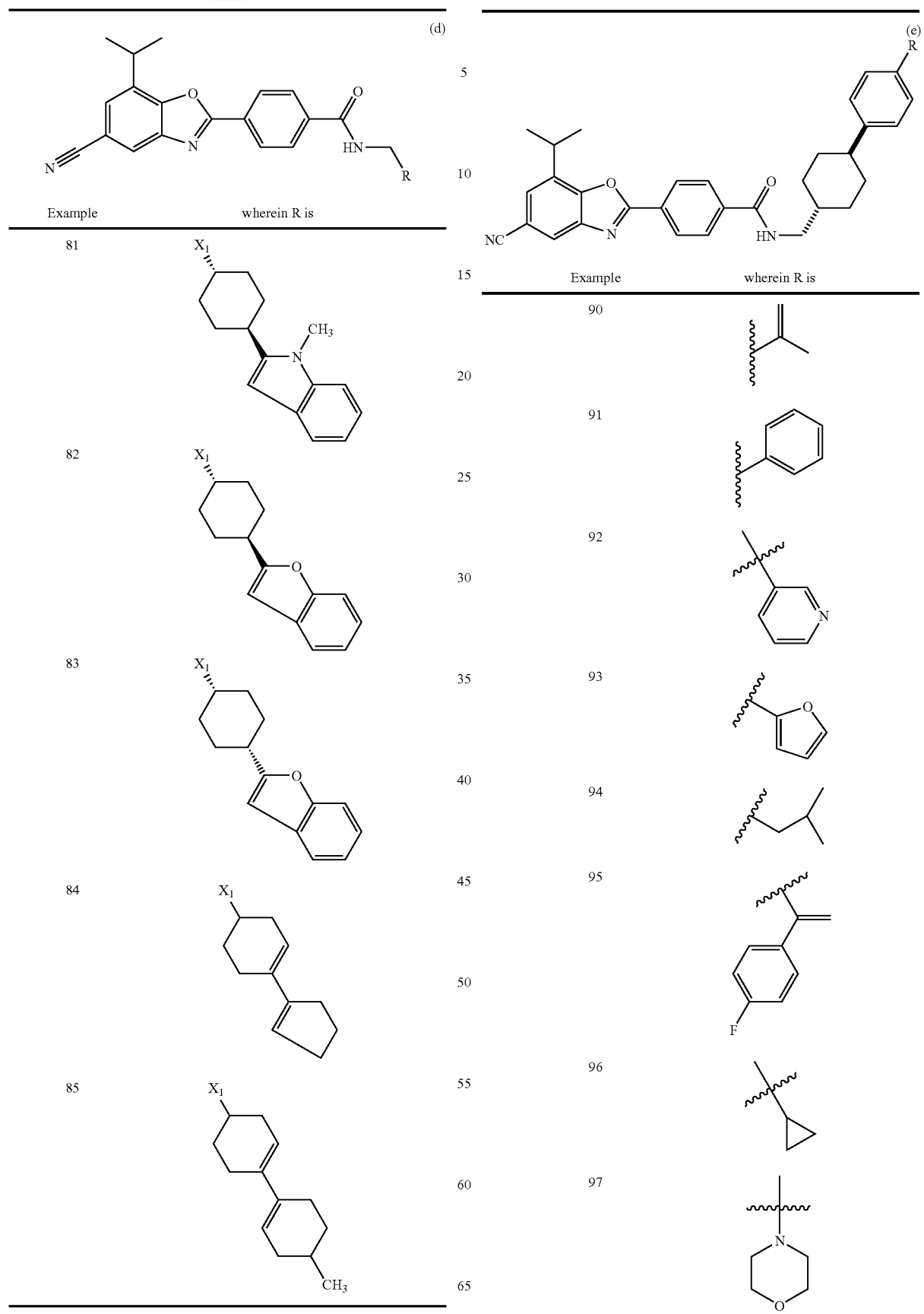

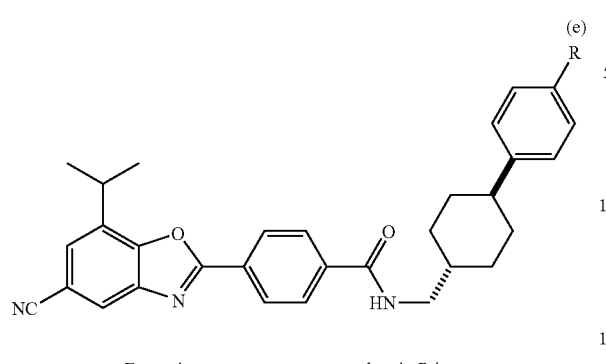
| Example | wherein R is |
|---|---|
| 98 | 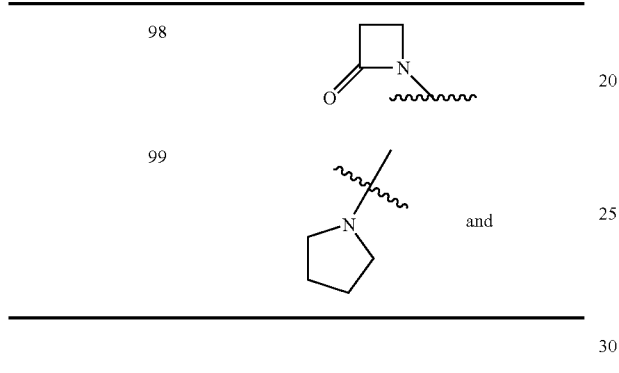 |
| 99 | and |
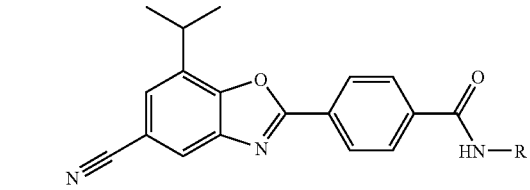
| Example | wherein R is |
|---|---|
| 100 | 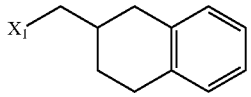 |
| 101 | 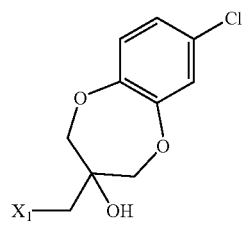 |
| 102 | |
| Example | wherein R is |
|---|---|
| 103 | 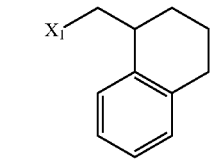 |
| 104 | 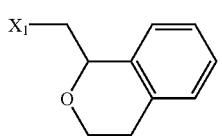 |
| 105 | 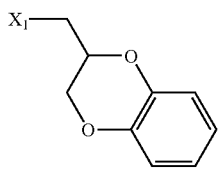 |
| 106 | |
| 107 | 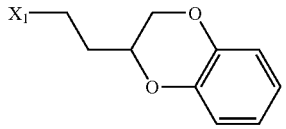 |
| 108 | 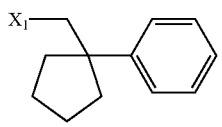 |
| 109 | |
| 110 | 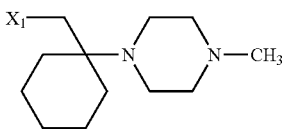 |
| 111 | 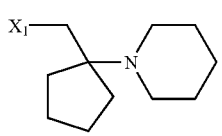 |

-continued

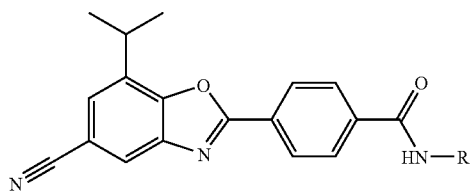
(f)

| Example | wherein R is |
|---|---|
| 112 | 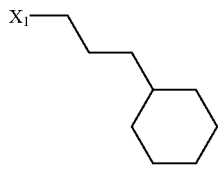 |
| 113 | 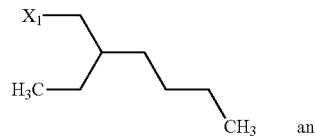 and |
| 114 | 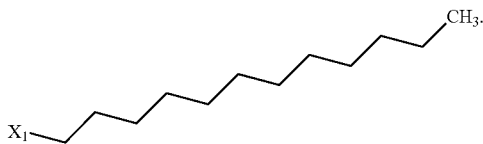 |

14. A pharmaceutical composition comprising the compound of claim 1 or a pharmaceutically acceptable salt thereof, a pharmaceutically acceptable carrier, and one or more active ingredients selected from the group consisting of:
(i) HMG-CoA reductase inhibitors;
(ii) bile acid sequestrants;
(iii) niacin and related compounds;
(iv) PPARα agonists;
(v) cholesterol absorption inhibitors;
(vi) acyl CoA:cholesterol acyltransferase (ACAT) inhibitors;
(vii) phenolic anti-oxidants;
(viii) microsomal triglyceride transfer protein (MTP)/ApoB secretion inhibitors;
(ix) anti-oxidant vitamins;
(x) thyromimetics;
(xi) LDL (low density lipoprotein) receptor inducers;
(xii) platelet aggregation inhibitors;
(xiii) vitamin B12 (also known as cyanocobalamin);
(xiv) folic acid or a pharmaceutically acceptable salt or ester thereof;
(xv) FXR and LXR ligands;
(xvi) agents that enhance ABCA1 gene expression; and
(xvii) ileal bile acid transporters.

15. A pharmaceutical composition comprising the compound of claim 1, or a pharmaceutically acceptable salt thereof, and a pharmaceutically acceptable carrier.

16. A method of treating atherosclerosis in a patient in need of treatment comprising the administration of a therapeutically effective amount of the compound of claim 1 to said patient, or a pharmaceutically acceptable salt thereof.

17. A method of raising HDL-C in a patient in need of treatment comprising the administration of a therapeutically effective amount of the compound of claim 1 to said patient, or a pharmaceutically acceptable salt thereof.

18. A method of lowering LDL-C in a patient in need of treatment comprising the administration of a therapeutically effective amount of the compound of claim 1 to said patient, or a pharmaceutically acceptable salt thereof.

* * * * *